US010653693B2

(12) United States Patent
Duncan et al.

(10) Patent No.: US 10,653,693 B2
(45) Date of Patent: May 19, 2020

(54) PRMT5 INHIBITORS AND USES THEREOF

(71) Applicants: Epizyme, Inc., Cambridge, MA (US); Glaxosmithkline Intellectual Property Development Limited, Brentford (GB)

(72) Inventors: Kenneth W. Duncan, Westwood, MA (US); Richard Chesworth, Concord, MA (US); Paula Ann Boriack-Sjodin, Lexington, MA (US); Michael John Munchhof, Salem, CT (US); Lei Jin, Wellesley, MA (US); Elayne Penebre, Auburndale, MA (US); Olena I. Barbash, Collegeville, PA (US)

(73) Assignees: Epizyme, Inc., Cambridge, MA (US); Glaxosmithkline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/501,550

(22) PCT Filed: Aug. 4, 2015

(86) PCT No.: PCT/US2015/043679
§ 371 (c)(1),
(2) Date: Feb. 3, 2017

(87) PCT Pub. No.: WO2016/022605
PCT Pub. Date: Feb. 11, 2016

(65) Prior Publication Data
US 2017/0224685 A1    Aug. 10, 2017

Related U.S. Application Data

(60) Provisional application No. 62/194,459, filed on Jul. 20, 2015, provisional application No. 62/148,713, filed on Apr. 16, 2015, provisional application No. 62/033,095, filed on Aug. 4, 2014.

(51) Int. Cl.
| | | |
|---|---|---|
| *A61K 31/506* | (2006.01) | |
| *A61K 31/4725* | (2006.01) | |
| *A61K 31/513* | (2006.01) | |
| *A61P 35/00* | (2006.01) | |
| *A61K 45/06* | (2006.01) | |
| *G01N 33/574* | (2006.01) | |

(52) U.S. Cl.
CPC ........ *A61K 31/506* (2013.01); *A61K 31/4725* (2013.01); *A61K 31/513* (2013.01); *A61K 45/06* (2013.01); *A61P 35/00* (2018.01); *G01N 33/57496* (2013.01); *G01N 2333/4748* (2013.01)

(58) Field of Classification Search
CPC .............. A61K 31/4725; A61K 31/506; A61K 31/513; A61K 45/06; G01N 2333/4748; G01N 33/57496; A61P 35/00

USPC ...................................................... 514/1, 210
See application file for complete search history.

(56) References Cited

U.S. PATENT DOCUMENTS

| | | | |
|---|---|---|---|
| 4,022,776 A | 5/1977 | Nakagawa et al. | |
| 4,059,621 A | 11/1977 | Vincent et al. | |
| 4,113,463 A | 9/1978 | Oshio et al. | |
| 4,365,064 A | 12/1982 | Takacs et al. | |
| 4,604,400 A | 8/1986 | Collins et al. | |
| 4,684,459 A | 8/1987 | Klimpel et al. | |
| 4,746,655 A | 5/1988 | Cale, Jr. | |
| 4,912,115 A | 3/1990 | Bomhard et al. | |
| 5,204,357 A | 4/1993 | Henning et al. | |
| 5,294,621 A | 3/1994 | Russell | |
| 5,514,694 A | 5/1996 | Powers et al. | |
| 5,693,847 A | 12/1997 | Tung et al. | |
| 6,034,097 A | 3/2000 | DiMaio et al. | |
| 6,130,217 A | 10/2000 | Arnold et al. | |
| 6,218,393 B1 | 4/2001 | Ryder et al. | |
| 7,176,242 B2 | 2/2007 | John et al. | |
| 7,253,165 B2 | 8/2007 | Shutske et al. | |
| 7,265,122 B2 | 9/2007 | Wu et al. | |
| 7,335,779 B2 | 2/2008 | Ammendola et al. | |
| 7,338,969 B2 | 3/2008 | Ammendola et al. | |
| 7,423,067 B2 | 9/2008 | Hagmann et al. | |
| 7,727,997 B2 | 6/2010 | John et al. | |
| 7,829,713 B2 | 11/2010 | Keenan et al. | |
| 8,071,624 B2 | 12/2011 | Yao et al. | |

(Continued)

FOREIGN PATENT DOCUMENTS

| | | |
|---|---|---|
| AU | 616071 B2 | 10/1991 |
| CA | 2383340 | 3/2001 |

(Continued)

OTHER PUBLICATIONS

Nigro et al., "Mutations in the p53 gene occur in diverse human tumour types", 1989, Nature, 342, pp. 705-708. (Year: 1989).*

(Continued)

*Primary Examiner* — My-Chau T. Tran
(74) *Attorney, Agent, or Firm* — Wolf, Greenfield & Sacks, P.C.

(57) ABSTRACT

Described herein are methods of treating cancer using one or more PRMT5 inhibitors, for example using one or more compounds of Formulae (1-5) or (A-F), pharmaceutically acceptable salts thereof, and/or pharmaceutical compositions thereof. Described herein are methods of treating cancer using one or more PRMT5 inhibitors, for example using one or more compounds of Formulae (1-5) or (A-F), pharmaceutically acceptable salts thereof, and/or pharmaceutical compositions thereof.

17 Claims, 31 Drawing Sheets

Specification includes a Sequence Listing.

(56) References Cited

U.S. PATENT DOCUMENTS

| | | |
|---|---|---|
| 8,076,516 B2 | 12/2011 | Scott et al. |
| 8,084,621 B2 | 12/2011 | Tang et al. |
| 8,119,633 B2 | 2/2012 | Merla et al. |
| 8,247,436 B2 | 8/2012 | Baettig et al. |
| 8,309,547 B2 | 11/2012 | Bodhuri et al. |
| 8,450,527 B2 | 5/2013 | Scott et al. |
| 8,546,579 B2 | 10/2013 | Kelly |
| 8,642,660 B2 | 2/2014 | Goldfarb |
| 8,722,851 B2 | 5/2014 | Wang et al. |
| 8,906,900 B2 | 12/2014 | Duncan et al. |
| 8,940,726 B2 | 1/2015 | Duncan et al. |
| 8,952,026 B2 | 2/2015 | Mitchell et al. |
| 8,993,555 B2 | 3/2015 | Duncan et al. |
| 9,023,883 B2 | 5/2015 | Kuntz et al. |
| 9,045,455 B2 | 6/2015 | Mitchell et al. |
| 9,120,757 B2 | 9/2015 | Chesworth et al. |
| 9,133,189 B2 | 9/2015 | Chesworth et al. |
| 9,221,794 B2 | 12/2015 | Duncan et al. |
| 9,266,836 B2 | 2/2016 | Duncan et al. |
| 9,346,761 B2 | 5/2016 | Chesworth et al. |
| 9,346,802 B2 | 5/2016 | Chesworth et al. |
| 9,354,223 B2 | 5/2016 | Wang et al. |
| 9,365,519 B2 | 6/2016 | Duncan et al. |
| 9,365,527 B2 | 6/2016 | Chesworth et al. |
| 9,365,555 B2 | 6/2016 | Duncan et al. |
| 9,388,173 B2 | 7/2016 | Duncan et al. |
| 9,394,258 B2 | 7/2016 | Chesworth et al. |
| 9,440,950 B2 | 9/2016 | Mitchell et al. |
| 9,447,079 B2 | 9/2016 | Mitchell et al. |
| 9,475,776 B2 | 10/2016 | Kuntz et al. |
| 9,598,374 B2 | 3/2017 | Chesworth et al. |
| 9,604,930 B2 | 3/2017 | Duncan et al. |
| 9,611,257 B2 | 4/2017 | Duncan et al. |
| 9,630,961 B2 | 4/2017 | Chesworth et al. |
| 9,675,614 B2 | 6/2017 | Duncan et al. |
| 9,718,816 B2 | 8/2017 | Chesworth et al. |
| 9,724,332 B2 | 8/2017 | Chesworth et al. |
| 9,732,041 B2 | 8/2017 | Chesworth et al. |
| 9,732,072 B2 | 8/2017 | Duncan et al. |
| 9,745,291 B2 | 8/2017 | Duncan et al. |
| 9,765,035 B2 | 9/2017 | Chesworth et al. |
| 9,765,068 B2 | 9/2017 | Duncan et al. |
| 9,776,972 B2 | 10/2017 | Chesworth et al. |
| 9,777,008 B2 | 10/2017 | Duncan et al. |
| 9,856,267 B2 | 1/2018 | Chesworth et al. |
| 9,868,703 B2 | 1/2018 | Kuntz et al. |
| 9,884,846 B2 * | 2/2018 | Clark .................. C07D 401/14 |
| 9,908,887 B2 | 3/2018 | Duncan et al. |
| 9,943,504 B2 | 4/2018 | Chesworth et al. |
| 9,981,948 B2 * | 5/2018 | Clark .................. C07D 401/14 |
| 10,039,748 B2 | 8/2018 | Mitchell et al. |
| 10,118,918 B2 | 11/2018 | Duncan et al. |
| 10,150,758 B2 | 12/2018 | Duncan et al. |
| 10,307,413 B2 | 6/2019 | Duncan et al. |
| 10,391,089 B2 * | 8/2019 | Duncan .................... A61P 3/04 |
| 2002/0169101 A1 | 11/2002 | Gonzalez et al. |
| 2003/0130280 A1 | 7/2003 | O'Farrell et al. |
| 2005/0124001 A1 | 6/2005 | Coats et al. |
| 2005/0154202 A1 | 7/2005 | Hagmann et al. |
| 2005/0239790 A1 | 10/2005 | John et al. |
| 2006/0009510 A1 | 1/2006 | Havens et al. |
| 2007/0004695 A1 | 1/2007 | Fink et al. |
| 2007/0010526 A1 | 1/2007 | Haeberlein et al. |
| 2007/0185152 A1 | 8/2007 | Yamashita et al. |
| 2007/0203124 A1 | 8/2007 | Keenan et al. |
| 2009/0093493 A1 | 4/2009 | Berardi et al. |
| 2009/0176776 A1 | 7/2009 | Prevelige |
| 2010/0048590 A1 | 2/2010 | Gailunas et al. |
| 2010/0093865 A1 | 4/2010 | Scott et al. |
| 2010/0113539 A1 | 5/2010 | Scott et al. |
| 2010/0222304 A1 | 9/2010 | Chiang et al. |
| 2011/0009420 A1 | 1/2011 | Andersen |
| 2011/0178123 A1 | 7/2011 | Ghosh |
| 2012/0014968 A1 | 1/2012 | Walsh et al. |
| 2012/0277232 A1 | 11/2012 | Baettig et al. |
| 2013/0158019 A1 | 6/2013 | Bryan et al. |
| 2014/0213582 A1 | 7/2014 | Duncan et al. |
| 2014/0221345 A1 | 8/2014 | Duncan et al. |
| 2014/0228343 A1 | 8/2014 | Duncan et al. |
| 2014/0228360 A1 | 8/2014 | Duncan et al. |
| 2014/0329794 A1 | 11/2014 | Duncan et al. |
| 2015/0133427 A1 | 5/2015 | Duncan et al. |
| 2015/0191432 A1 | 7/2015 | Duncan et al. |
| 2015/0252031 A1 | 9/2015 | Duncan et al. |
| 2015/0344433 A1 | 12/2015 | Duncan et al. |
| 2015/0344434 A1 | 12/2015 | Duncan et al. |
| 2015/0344457 A1 | 12/2015 | Duncan et al. |
| 2015/0344463 A1 | 12/2015 | Duncan et al. |
| 2015/0361042 A1 | 12/2015 | Duncan et al. |
| 2016/0031839 A1 | 2/2016 | Chesworth et al. |
| 2016/0039767 A1 | 2/2016 | Mitchell et al. |
| 2016/0039834 A1 | 2/2016 | Chesworth et al. |
| 2016/0137609 A1 | 5/2016 | Chesworth et al. |
| 2016/0137631 A1 | 5/2016 | Duncan et al. |
| 2016/0214985 A1 | 7/2016 | Duncan et al. |
| 2016/0368907 A1 | 12/2016 | Duncan et al. |
| 2017/0027935 A1 | 2/2017 | Duncan et al. |
| 2017/0056409 A1 | 3/2017 | Chesworth et al. |
| 2017/0057926 A1 | 3/2017 | Chesworth et al. |
| 2017/0088529 A1 | 3/2017 | Chesworth et al. |
| 2017/0088541 A1 | 3/2017 | Duncan et al. |
| 2017/0114061 A1 | 4/2017 | Duncan et al. |
| 2017/0119735 A1 | 5/2017 | Chesworth et al. |
| 2017/0182005 A1 | 6/2017 | Mitchell et al. |
| 2017/0198006 A1 * | 7/2017 | Duncan .................. C07D 401/14 |
| 2017/0210751 A1 | 7/2017 | Duncan et al. |
| 2017/0224685 A1 | 8/2017 | Duncan et al. |
| 2017/0233347 A1 | 8/2017 | Kuntz et al. |
| 2017/0240537 A1 | 8/2017 | Duncan et al. |
| 2017/0267642 A1 | 9/2017 | Chesworth et al. |
| 2017/0280720 A1 | 10/2017 | Chesworth et al. |
| 2017/0283400 A1 | 10/2017 | Mitchell et al. |
| 2017/0283440 A1 | 10/2017 | Chesworth et al. |
| 2017/0291905 A1 | 10/2017 | Chesworth et al. |
| 2017/0298073 A1 | 10/2017 | Olhava et al. |
| 2017/0334861 A1 | 11/2017 | Duncan et al. |
| 2018/0098987 A1 | 4/2018 | Duncan et al. |
| 2018/0105497 A1 | 4/2018 | Chesworth et al. |
| 2018/0162847 A1 | 6/2018 | Duncan et al. |
| 2018/0186798 A1 | 7/2018 | Duncan et al. |
| 2018/0237397 A1 | 8/2018 | Chesworth et al. |
| 2018/0298010 A1 | 10/2018 | Duncan et al. |
| 2018/0303822 A1 | 10/2018 | Duncan et al. |
| 2019/0083482 A1 | 3/2019 | Duncan et al. |

FOREIGN PATENT DOCUMENTS

| | | |
|---|---|---|
| CN | 101 012 223 A | 8/2007 |
| DE | 63776 A | 9/1968 |
| DE | 68906 A | 9/1969 |
| EP | 2 409 977 A1 | 1/2012 |
| WO | WO 91/13865 A1 | 9/1991 |
| WO | WO 93/01174 A1 | 1/1993 |
| WO | WO 94/01408 A1 | 1/1994 |
| WO | WO 95/11680 A1 | 5/1995 |
| WO | WO 01/19821 A1 | 3/2001 |
| WO | WO 01/19833 A1 | 3/2001 |
| WO | WO 02/14277 A1 | 2/2002 |
| WO | WO 2004/022558 A2 | 3/2004 |
| WO | WO 2004/060882 A1 | 7/2004 |
| WO | WO 2004/078114 A2 | 9/2004 |
| WO | WO 2005/118543 A1 | 12/2005 |
| WO | WO 2007/015805 A1 | 2/2007 |
| WO | WO 2007/087572 A2 | 8/2007 |
| WO | WO 2008/100621 A2 | 8/2008 |
| WO | WO 2008/104077 A1 | 9/2008 |
| WO | WO 2008/145398 A1 | 12/2008 |
| WO | WO 2010/057101 A2 | 5/2010 |
| WO | WO 2011/077133 A2 | 6/2011 |
| WO | WO 2011/079236 A1 | 6/2011 |
| WO | WO 2012/051692 A1 | 4/2012 |
| WO | WO 2013/038378 A1 | 3/2013 |
| WO | WO 2013/038381 A1 | 3/2013 |
| WO | WO 2013/071697 A1 | 5/2013 |

(56) References Cited

FOREIGN PATENT DOCUMENTS

| WO | WO 2013/098416 A2 | 7/2013 |
|---|---|---|
| WO | WO 2014/048547 A1 | 4/2014 |
| WO | WO 2014/100695 A1 | 6/2014 |
| WO | WO 2014/100716 A1 | 6/2014 |
| WO | WO 2014/100719 A1 | 6/2014 |
| WO | WO 2014/100730 A1 | 6/2014 |
| WO | WO 2014/100734 A1 | 6/2014 |
| WO | WO 2014/100764 A1 | 6/2014 |
| WO | WO 2014/144169 A1 | 9/2014 |
| WO | WO 2014/144455 A1 | 9/2014 |
| WO | WO 2014/144659 A1 | 9/2014 |
| WO | WO 2014/153090 A1 | 9/2014 |
| WO | WO 2014/153100 A1 | 9/2014 |
| WO | WO 2014/153172 A1 | 9/2014 |
| WO | WO 2014/153208 A1 | 9/2014 |
| WO | WO 2014/153214 A1 | 9/2014 |
| WO | WO 2014/153226 A1 | 9/2014 |
| WO | WO 2014/153235 A1 | 9/2014 |
| WO | WO 2014/178954 A1 | 11/2014 |
| WO | WO 2015/200677 A1 | 12/2015 |
| WO | WO 2015/200680 A1 | 12/2015 |
| WO | WO 2016/022605 A1 | 2/2016 |
| WO | WO 2016/044556 A2 | 3/2016 |
| WO | WO 2016/044569 A1 | 3/2016 |
| WO | WO 2016/044576 A1 | 3/2016 |
| WO | WO 2016/044585 A1 | 3/2016 |
| WO | WO 2016/044604 A1 | 3/2016 |
| WO | WO 2016/044626 A1 | 3/2016 |
| WO | WO 2016/044641 A2 | 3/2016 |
| WO | WO 2016/044650 A1 | 3/2016 |
| WO | WO 2017/136699 A1 | 8/2017 |

OTHER PUBLICATIONS

Mu et al., "p53 protein expression and CA19.9 values in differential cytological diagnosis of pancreatic cancer complicated with chronic pancreatitis and chronic pancreatitis", 2003, World J Gastroenterol., 9(8), pp. 1815-1818. (Year: 2003).*
Ando et al., "Discrimination of p53 immunohistochemistry-positive tumors by its staining pattern in gastric cancer", 2015, Cancer Medicine, 4(1), pp. 75-83. (Year: 2015).*
Havelek et al., "The effect of Amaryllidaceae alkaloids haemanthamine and haemanthidine on cell cycle progression and apoptosis in p53-negative human leukemic Jurkat cells", Mar. 2014, Phytomedicine, 21(4), pp. 479-490. (Available online Oct. 29, 2013.) (Year: 2014).*
Extended European Search Report for International Application No. EP 15830530.0 dated Mar. 2, 2018.
Jansson et al., Arginine methylation regulates the p53 response. Nat Cell Biol. Dec. 2008;10(12):1431-9. doi: 10.1038/ncb1802. Epub Nov. 16, 2008.
International Search Report and Written Opinion for International Application No. PCT/US2013/077151 dated Jun. 2, 2014.
International Search Report and Written Opinion for International Application No. PCT/US2013/077221 dated Apr. 30, 2014.
International Search Report and Written Opinion for International Application No. PCT/US2013/077235 dated Jun. 16, 2014.
International Search Report and Written Opinion for International Application No. PCT/US2013/077250 dated May 16, 2014.
International Search Report and Written Opinion for International Application No. PCT/US2013/077308 dated Aug. 7, 2014.
International Search Report and Written Opinion for International Application No. PCT/US2013/077256 dated Apr. 14, 2014.
International Search Report and Written Opinion for International Application No. PCT/US2015/037759 dated Jan. 11, 2016.
International Search Report and Written Opinion for International Application No. PCT/US2015/037768 dated Jan. 11, 2016.
International Search Report and Written Opinion for International Application No. PCT/US2015/043679 dated Nov. 24, 2015.
[No Author Listed], Cancer [online], [retrieved on Jul. 6, 2007]. Medline Plus. Retrieved from the internet, URL www.nlm.nih.gov/medlineplus/cancer.html. 10 pages.

[No Author Listed], Cancer [online], [retrieved on Jul. 6, 2007]. Wikipedia. Retrieved from the internet, URL http://en.wikipedia.org/wiki/Cancer. 2 pages.
[No Author Listed], EnamineStore, 1 page retrieved from the Internet athttp://www.enamine.net/index.php?option=com_content&task=view&id=22. Accessed Apr. 13, 2015.
Abate et al., Arylamides hybrids of two high-affinity σ2 receptor ligands as tools for the development of PET radiotracers. Eur J Med Chem. Sep. 2011;46(9):4733-41. doi: 10.1016/j.ejmech.2011.05.057.
Aggarwal et al., Nuclear cyclin D1/CDK4 kinase regulates CUL4 expression and triggers neoplastic growth via activation of the PRMT5 methyltransferase. Cancer Cell. Oct. 19, 2010;18(4):329-40. doi: 10.1016/j.ccr.2010.08.012.
Andreu-Pérez et al., Protein arginine methyltransferase 5 regulates ERK1/2 signal transduction amplitude and cell fate through Craf. Sci Signal. Sep. 13, 2011;4(190):ra58. doi: 10.1126/scisignal.2001936.
Antonysamy et al., Crystal structure of the human PRMT5:MEP50 complex. Proc Natl Acad Sci USA. Oct. 30, 2012;109(44):17960-5. doi: 10.1073/pnas.1209814109. Epub Oct. 15, 2012.
Bandyopadhyay et al., HOXA9 methylation by PRMT5 is essential for endothelial cell expression of leukocyte adhesion molecules. Mol Cell Biol. Apr. 2012;32(7):1202-13. doi: 10.1128/MCB.05977-11. Epub Jan. 23, 2012.
Bao et al., Overexpression of PRMT5 Promotes Tumor Growth and is Associated with Poor Disease Prognosis in Epithelial Ovarian Cancer. J Histochem Cytochem. Mar. 2013;61(3):206-17. doi: 10.1369/0022155413475452. Epub Jan. 4, 2013.
Bergmann et al., Synthesis and structure-activity relationship of some new β-blocking agents with possible α-adrenoreceptor activity. Arch Pharm. 1990;323:387-91.
Bezzi et al., Regulation of constitutive and alternative splicing by PRMT5 reveals a role for Mdm4 pre-mRNA in sensing defects in the spliceosomal machinery. Genes Dev. Sep. 1, 2013;27(17):1903-16. doi: 10.1101/gad.219899.113.
Brown et al., Receptor binding sites of hypoglycemic sulfonylureas and related [(acylamino)alkyl]benzoic acids. J Med Chem. Jan. 1984;27(1):79-81.
CA Registry No. 1301253-27-9, entered into CA Registry File on May 26, 2011, supplied by FCH Group.
Camp et al., Adipogenesis and fat-cell function in obesity and diabetes. Trends Mol Med. Sep. 2002;8(9):442-7.
CAPLUS Accesion No. 2000:487675. 4 pages.
CAPLUS Accesion No. 2009:1302026. 1 page. Korotkii et al., Synthesis and antimicrobial activity of 1-[4-(1-adamantyl)phenoxy]-3-amino-2-propanol. Pharma Chem J. 2009;43(6):301-4. Abstract.
CAPLUS Accesion No. 2010:485537. Prytula et al., Synthesis and spasmolytic activity of (di)hydrochlorides and quaternary salts of some adamantyl-containing derivatives of 1-alkoxy-3-dialkylamino-2-propanol. Zhurnal Organichnoi to Farmatsevtichnoi Khimii. 2010;8(1):25-9. Abstract.
Carey, Organic Chemisry. NY McGraw-Hill 2000 p. G-2.
CAS Registry No. 923141-67-7. Feb. 26, 2007. 1 page.
CAS Registry No. 1008707-00-3. Mar. 18, 2008. 1 page.
CAS Registry No. 1022648-78-7. May 26, 2008. 1 page.
CAS Registry No. 1023185-95-6. May 28, 2008. 1 page.
CAS Registry No. 1119379-87-1. Mar. 12, 2009. 1 page.
CAS Registry No. 1181543-32-7. Sep. 9, 2009. 1 page.
CAS Registry No. 1208850-42-3. Mar. 11, 2010. 1 page.
CAS Registry No. 1211677-43-8. Mar. 19, 2010. 1 page.
CAS Registry No. 1222970-06-0. May 13, 2010. 1 page.
CAS Registry No. 1240952-30-0. Sep. 14, 2010. 1 page.
CAS Registry No. 1252266-42-4. Nov. 10, 2010. 1 page.
CAS Registry No. 1277113-61-7. Apr. 8, 2011. 1 page.
CAS Registry No. 1278970-87-8. Apr. 12, 2011. 1 page.
CAS Registry No. 1284717-34-5. Apr. 24, 2011. 1 page.
CAS Registry No. 1288518-05-7. May 1, 2011. 1 page.
CAS Registry No. 1299664-19-9. May 24, 2011. 1 page.
CAS Registry No. 1302193-68-5. May 29, 2011. 1 page.
CAS Registry No. 1316197-59-7. Aug. 11, 2011. 1 page.
CAS Registry No. 1316369-94-4. Aug. 12, 2011. 1 page.
CAS Registry No. 1317245-22-9. Aug. 14, 2011. 1 page.

(56) References Cited

OTHER PUBLICATIONS

CAS Registry No. 1318219-96-3. Aug. 15, 2011. 1 page.
CAS Registry No. 1318644-07-3. Aug. 16, 2011. 1 page.
CAS Registry No. 1319342-38-5. Aug. 18, 2011. 1 page.
CAS Registry No. 1319931-54-8. Aug. 19, 2011. 1 page.
CAS Registry No. 1321571-71-4. Aug. 22, 2011. 1 page.
CAS Registry No. 1322145-39-0. Aug. 23, 2011. 1 page.
CAS Registry No. 1322579-97-4. Aug. 24, 2011. 1 page.
CAS Registry No. 1330937-75-1. Sep. 11, 2011. 1 page.
CAS Registry No. 1347256-93-2. Dec. 2, 2011. 1 page.
CAS Registry No. 1348874-66-7. Dec. 5, 2011. 1 page.
CAS Registry No. 1349512-40-8. Dec. 6, 2011. 1 page.
CAS Registry No. 1350276-64-0. Dec. 7, 2011. 1 page.
CAS Registry No. 1355706-85-2. Feb. 7, 2012. 1 page.
CAS Registry No. 1356778-99-8. Feb. 14, 2012. 1 page.
CAS Registry No. 1372312-69-0. May 2, 2012. 1 page.
CAS Registry No. 1376006-97-1. Jun. 7, 2012. 1 page.
CAS Registry No. 1410908-63-2. Dec. 4, 2012. 1 page.
CAS Registry No. 1424333-72-1. Mar. 15, 2013. 1 page. Supplied by Enamine Chemical Library.
CAS Registry No. 1424365-18-3. Mar. 15, 2013. 1 page.
CAS Registry No. 1424444-20-1. Mar. 17, 2013. 1 page.
CAS Registry No. 1424524-36-6. Mar. 17, 2013. 1 page.
CAS Registry No. 1427932-67-9. Apr. 11, 2013. 1 page.
CAS Registry No. 1428095-08-2. Apr. 11, 2013. 1 page.
CAS Registry No. 1436034-24-0. Jun. 9, 2013. 1 page.
CAS Registry No. 1444031-91-7. Jul. 15, 2013. 1 page.
CAS Registry No. 1444637-79-9. Jul. 16, 2013. 1 page.
CAS Registry No. 1444638-11-2. Jul. 16, 2013. 1 page.
CAS Registry No. 1445155-97-4. Jul. 17, 2013. 1 page.
CAS Registry No. 1445348-70-8. Jul. 18, 2013. 1 page.
CAS Registry No. 1455081-19-2. Oct. 4, 2013. 1 page.
CAS Registry No. 1455191-29-3. Oct. 4, 2013. 1 page.
CAS Registry No. 1456315-86-8. Oct. 6, 2013. 1 page.
CAS Registry No. 1479608-80-4. Nov. 24, 2013. 1 page.
CAS Registry No. 155083-65-1. May 17, 1994. 1 page.
CAS Registry No. 2002:142672. Compound 400726-94-5. Mar. 13, 2002.
CAS Registry No. 261164-91-4. Apr. 6, 2000. 1 page.
CAS Registry No. 524721-03-7. Jun. 3, 2003. 1 page.
CAS Registry No. 717121-35-2. Jul. 27, 2004. 1 page.
CAS Registry No. 737696-45-6. Sep. 2, 2004. 1 page.
CAS Registry No. 770646-48-5. Oct. 27, 2004. 1 page.
CAS Registry No. 801197-71-7. Dec. 22, 2004. 1 page.
CAS Registry No. 802313-31-1. Dec. 25, 2004. 1 page.
CAS Registry No. 802601-62-3. Dec. 26, 2004. 1 page.
CAS Registry No. 803623-34-9. Dec. 27, 2004. 1 page.
CAS Registry No. 848051-57-0. Apr. 7, 2005. 1 page.
CAS Registry No. 886136-98-7. May 31, 2006. 1 page.
CAS Registry No. 913503-11-4. Nov. 17, 2006. 1 page.
CAS Registry Nos. 1005082-40-5; 1005067-47-9. Feb. 22, 2008. 2 pages.
CAS Registry Nos. 1049761-31-0; 1049760-28-2. Sep. 17, 2008. 2 pages.
CAS Registry Nos. 1060402-35-8; 1060400-38-5; 1060393-44-3; 1060386-32-4. Oct. 13, 2008. 3 pages.
CAS Registry Nos. 1060542-64-4; 1060516-49-5; 1060507-45-0. Oct. 13, 2008. 2 pages.
CAS Registry Nos. 1061124-54-6; 1061056-39-0; 1061053-40-4. Oct. 14, 2008. 2 pages.
CAS Registry Nos. 1065507-26-7; 1065489-20-4. Oct. 24, 2008. 1 page.
CAS Registry Nos. 1066959-19-0; 1066956-31-7; 1066945-12-7; 1066929-96-1; 1066909-51-0; 1066881-34-2. Oct. 27, 2008. 3 pages.
CAS Registry Nos. 1067029-15-5; 1067022-11-0; 1067018-55-6; 1067015-90-0. Oct. 27, 2008. 2 pages.
CAS Registry Nos. 1069781-86-7; 1069771-01-2; 1069759-22-3; 1069751-87-6; 1069743-52-7. Nov. 2, 2008. 3 pages.
CAS Registry Nos. 1069895-07-3; 1069893-60-2; 1069891-30-0; 1069888-39-6. Nov. 2, 2008. 2 pages.
CAS Registry Nos. 1069906-08-6; 1069902-26-6; 1069901-02-5; 1069900-62-4; 1069899-08-6; 1069897-82-0. Nov. 2, 2008. 3 pages.
CAS Registry Nos. 1070344-15-8; 1070324-71-8; 1070322-58-5; 1070314-79-2; 1070296-71-7; 1070290-15-1; 1070285-19-6; 1070262-09-7. Nov. 3, 2008. 5 pages.
CAS Registry Nos. 1147700-86-4; 1147642-86-1. May 20, 2009. 1 page.
CAS Registry Nos. 1185407-05-09; 1185405-44-0; 1185390-39-9; 1185381-01-4. Sep. 17, 2009. 2 pages.
CAS Registry Nos. 1197943-03-5; 1197564-92-3. Dec. 16, 2009. 1 page.
CAS Registry Nos. 1203413-85-7; 1203375-38-5; 1203348-04-2; 1203233-98-0; 1203173-19-6; 1203162-75-7; 1203144-35-7. 1203022-51-8. Jan. 24, 2010. 5 pages.
CAS Registry Nos. 1212367-31-1; 1212317-85-5; 1212316-36-3; 1212282-83-1; 1212276-27-1; 1212239-64-9. Mar. 21, 2010. 3 pages.
CAS Registry Nos. 1217840-37-3; 1217668-16-0; 1217666-80-2; 1217653-64-9; 1217620-01-3. Apr. 9, 2010. 3 pages.
CAS Registry Nos. 1223357-53-6; 1223349-33-4; 1223239-90-4; 1223228-05-4; 1223214-63-8. May 14, 2010. 2 pages.
CAS Registry Nos. 1241440-76-5; 1241250-19-0; 1241247-75-5; 1241156-35-3; 1241132-96-6; 1241132-91-1; 1241070-46-1; 1241070-44-9. Sep. 15, 2010. 4 pages.
CAS Registry Nos. 1252106-10-7; 1252099-82-3. Nov. 9, 2010. 1 page.
CAS Registry Nos. 1281089-87-9; 1280921-87-0. Apr. 17, 2011. 1 page.
CAS Registry Nos. 1288640-51-6; 1288640-50-5. May 1 , 2011. 1 page.
CAS Registry Nos. 1289351-04-7; 1289351-03-6. May 3, 2011. 1 page.
CAS Registry Nos. 1317589-67-5; 1317515-43-7; 1317334-82-9. Aug. 14, 2011. 2 pages.
CAS Registry Nos. 1317982-41-4; 1317968-41-4; 1317886-59-1. Aug. 15, 2011. 2 pages.
CAS Registry Nos. 1319121-25-9; 1319002-83-9; 1318997-32-8; 1318913-98-2; 1318883-46-3. Aug. 17, 2011. 3 pages.
CAS Registry Nos. 1320022-45-4; 1320021-13-3. Aug. 19, 2011. 1 page.
CAS Registry Nos. 1347539-89-2; 1347519-58-7; 1347361-44-7. Dec. 2, 2011. 3 pages.
CAS Registry Nos. 1355607-64-5; 1355578-94-7; 1355493-36-5. Feb. 7, 2012. 2 pages.
CAS Registry Nos. 1355914-92-9; 1355898-02-0. Feb. 8, 2012. 1 page.
CAS Registry Nos. 1371104-82-3; 1370816-34-4. Apr. 29, 2012. 1 page.
CAS Registry Nos. 1371555-26-8; 1371490-72-0; 1371483-54-3; 1371446-47-7; 1371346-43-8; 1371223-53-8. Apr. 30, 2012. 3 pages.
CAS Registry Nos. 1372108-95-6; 1372054-69-7. May 1, 2012. 1 page.
CAS Registry Nos. 1385588-44-2; 1385478-31-8. Aug. 2, 2012. 1 page.
CAS Registry Nos. 1385797-51-2; 1385797-47-6; 1385614-49-2. Aug. 2, 2012. 2 pages.
CAS Registry Nos. 1386280-12-1; 1386280-07-4; 1386148-41-9; 1386010-87-2. Aug. 3, 2012. 2 pages.
CAS Registry Nos. 1386827-14-0; 1386608-97-4. Aug. 6, 2012. 1 page.
CAS Registry Nos. 1387169-01-8; 1387167-55-6. Aug. 7, 2012. 1 page.
CAS Registry Nos. 1387456-55-4; 1387169-74-5; 1387110-73-7; 1387108-14-6. Aug. 7, 2012. 2 pages.
CAS Registry Nos. 1387845-06-8; 1387782-64-0. Aug. 8, 2012. 1 page.
CAS Registry Nos. 1388292-84-9; 1388292-67-8; 1388292-58-7. Aug. 9, 2012. 1 page.

(56) References Cited

OTHER PUBLICATIONS

CAS Registry Nos. 1388701-97-0; 1388690-94-5; 1388642-81-6; 1388576-16-6; 1388555-08-5; 1388432-00-5; 1388397-52-1; 1388369-92-3; 1388367-52-9. Aug. 9, 2012. 4 pages.
CAS Registry Nos. 1389150-41-7; 1389143-93-4; 1389138-17-3; 1388976-86-0; 1388976-44-0; 1388908-64-2. Aug. 12, 2012. 3 pages.
CAS Registry Nos. 1389191-79-0; 1389186-88-2. Aug. 10, 2012. 1 page.
CAS Registry Nos. 1389775-53-4; 1389743-08-01; 1389743-01-04. Aug. 12, 2012. 2 pages.
CAS Registry Nos. 1390079-59-0; 1390053-83-4; 1390037-12-3. Aug. 12, 2012. 1 page.
CAS Registry Nos. 1390262-63-1; 1389804-10-7; 1389608-63-2; 1389477-08-0. Aug. 12, 2012. 2 pages.
CAS Registry Nos. 1390485-95-6; 1390470-75-3; 1390466-88-2; 1390428-89-3. Aug. 13, 2012. 1 page.
CAS Registry Nos. 1390524-87-4,; 1390490-16-0; 1390364-38-1. Aug. 13, 2012. 2 pages.
CAS Registry Nos. 1394703-31-1; 1394698-39-5. Sep. 18, 2012. 1 page.
CAS Registry Nos. 1445163-85-8; 1444874-40-1; 1444830-50-5; 1444828-93-6; 1444693-38-2. Jul. 17, 2013. 3 pages.
CAS Registry Nos. 1445676-20-9; 1445676-11-8. Jul. 19, 2013. 1 page.
CAS Registry Nos. 958982-78-0; 958964-27-7. Dec. 20, 2007. 1 page.
CAS Registry Nos. 958563-68-3. Dec. 18, 2007.
Chimenti et al., Sintesi di Isoindoline N-Sostituite. Il Farmaco, Elsevier France. Scientifiques et Medicales, IT. Jan. 1974;30:884-90. French.
Cho et al., Arginine methylation controls growth regulation by E2F-1. EMBO J. Apr. 4, 2012;31(7):1785-97. doi: 10.1038/emboj.2012.17. Epub Feb. 10, 2012.
FCH Group Product Guide, 1 page, retrieved from the Internet at http://fchgroup.net/products.php on Apr. 5, 2014.
Fontan et al., Novel symmetrical ureas as modulators of protein arginine methyl transferases. Bioorg Med Chem. Apr. 1, 2013;21(7):2056-67. doi: 10.1016/j.bmc.2013.01.017. Epub Jan. 22, 2013.
Golub et al., Molecular classification of cancer: class discovery and class prediction by gene expression monitoring. Science. Oct. 15, 1999;286(5439):531-7.
Gu et al., Protein arginine methyltransferase 5 functions in opposite ways in the cytoplasm and nucleus of prostate cancer cells. PLoS One. 2012;7(8):e44033. doi: 10.1371/journal.pone.0044033. Epub Aug. 27, 2012.
Gu et al., Protein arginine methyltransferase 5 is essential for growth of lung cancer cells. Biochem J. Sep. 1, 2012;446(2):235-41. doi: 10.1042/BJ20120768.
Gunawan et al., Synthesis of Tetrazolo-Fused Benzodiazepines and Benzodiazepinones by a Two-Step Protocol Using an Ugi-Azide Reaction for Initial Diversity Generation. Tetrahedron. Jul. 8, 2012;68(27-28):5606-11. Epub Apr. 26, 2012.
Hawley's Condensed Chemical Dictionary. Excerpt "aliphatic". Online pub Mar. 2007.
Heidenbluth et al., Document No. 70:87572, retrieved from CAPLUS; Jan. 1, 1969.
Heidenbluth et al., Document No. 72:90279, retrieved from CAPLUS; Sep. 20, 1969.
Labaff, EZH2 T416 Phosphorylation Enhances Breast Cancer Tumorigenesis. Abstract. Dec. 2013.
Labrie et al., In vitro activity of novel dual action MDR anthranilamide modulators with inhibitory activity at CYP-450. Bioorg Med Chem. Dec. 1, 2006;14(23):7972-87. Epub Aug. 10, 2006.
Lala et al., Role of nitric oxide in tumor progression: lessons from experimental tumors. Cancer Metastasis Rev. Mar. 1998;17(1):91-106.
Leblanc et al., Protein arginine methyltransferase 5 (Prmt5) promotes gene expression of peroxisome proliferator-activated receptor γ2 (PPARγ2) and its target genes during adipogenesis. Mol Endocrinol. Apr. 2012;26(4):583-97. doi: 10.1210/me.2011-1162. Epub Feb. 23, 2012.
Maeda et al., Mechanism of the chemiluminescence of biisoquinolinium salts. J Chem Soc. Perkin 2. 1996;1:121-6.
Pal et al., Low levels of miR-92b/96 induce PRMT5 translation and H3R8/H4R3 methylation in mantle cell lymphoma. EMBO J. Aug. 8, 2007;26(15):3558-69. Epub Jul. 12, 2007.
Pubchem Submission; NIH/NCBI, Substance Identifier 103937775. BindingDB. Jan. 19, 2011. 5 pages.
Pubchem Submission; NIH/NCBI, Substance Identifier 107215563. AKos Consulting & Solutions. Feb. 22, 2011. 6 pages.
Pubchem Submission; NIH/NCBI, Substance Identifier 112367837. ABI Chem. Mar. 10, 2011. 6 pages.
Pubchem Submission; NIH/NCBI, Substance Identifier 136894295. Tetrahedron Scientific, Inc. Jul. 18, 2012. 6 pages.
Pubchem Submission; NIH/NCBI, Substance Identifier 144940718. AKos Consulting & Solutions. Oct. 18, 2012. 6 pages.
Rank et al., Identification of a PRMT5-dependent repressor complex linked to silencing of human fetal globin gene expression. Blood. Sep. 2, 2010;116(9):1585-92. doi: 10.1182/blood-2009-10-251116. Epub May 21, 2010.
Scoumanne et al., PRMT5 Is Required for Cell-Cycle Progression and P53 Tumor Suppressor Function. Nucleic Acids Res. Aug. 2009;37(15):4965-76. doi: 10.1093/nar/gkp516. Epub Jun. 15, 2009.
Seshadri, Attempts to find new anti-malarials. Part II. Aminoalkylquinolinium salts and some related substances. J Chem Soc. 1929:2952-9.
Smith et al., Epigenomic regulation of bile acid metabolism: emerging role of transcriptional cofactors. Mol Cell Endocrinol. Apr. 10, 2013;368(1-2):59-70. doi: 10.1016/j.mce.2012.04.008. Epub May 9, 2012. Review.
Spannhoff et al., Cancer treatment of the future: inhibitors of histone methyltransferases. Int J Biochem Cell Biol. Jan. 2009;41(1):4-11. doi: 10.1016/j.biocel.2008.07.024. Epub Aug. 14, 2008.
Stopa et al., The PRMT5 arginine methyltransferase: many roles in development, cancer and beyond. Cell Mol Life Sci. Jun. 2015;72(11):2041-59. doi: 10.1007/s00018-015-1847-9. Epub Feb. 7, 2015. Review.
Sun et al., Structural insights into protein arginine symmetric dimethylation by PRMT5. Proc Natl Acad Sci U S A. Dec. 20, 2011;108(51):20538-43. doi: 10.1073/pnas.1106946108. Epub Dec. 5, 2011.
Sunko et al., On the Reaction of alpha-Phthalimidoacid Chlorides with Substituted Sodiomalonates. A Method for the Preparation of alpha-Amino Ketones and Related Compounds. Arhiv Za Kemiju. 1954;26:7-14.
Tae et al., Bromodomain protein 7 interacts with PRMT5 and PRC2, and is involved in transcriptional repression of their target genes. Nucleic Acids Res. Jul. 2011;39(13):5424-38. doi: 10.1093/nar/gkr170. Epub Mar. 29, 2011.
Tanaka et al., PRMT5, a novel TRAIL receptor-binding protein, inhibits TRAIL-induced apoptosis via nuclear factor-kappaB activation. Mol Cancer Res. Apr. 2009;7(4):557-69. doi: 10.1158/1541-7786.MCR-08-0197.
Teng et al., Mutations in the Epidermal Growth Factor Receptor (EGFR) Gene in Triple Negative Breast Cancer: Possible Implications for Targeted Therapy. Abstract. Breast Cancer Research. 2011.
Tsutsui et al., Mediator complex recruits epigenetic regulators via its two cyclin-dependent kinase subunits to repress transcription of immune response genes. J Biol Chem. Jul. 19, 2013;288(29):20955-65. doi: 10.1074/jbc.M113.486746. Epub Jun. 9, 2013.
Wang et al., Protein arginine methyltransferase 5 suppresses the transcription of the RB family of tumor suppressors in leukemia and lymphoma cells. Mol Cell Biol. Oct. 2008;28(20):6262-77. doi: 10.1128/MCB.00923-08. Epub Aug. 11, 2008.
Wei et al., PRMT5 dimethylates R30 of the p65 subunit to activate NF-κB. Proc Natl Acad Sci U S A. Aug. 13, 2013;110(33):13516-21. doi: 10.1073/pnas.1311784110. Epub Jul. 31, 2013.
Wei et al., Protein arginine methyltransferase 5 is a potential oncoprotein that upregulates G1 cyclins/cyclin-dependent kinases

(56) References Cited

OTHER PUBLICATIONS and the phosphoinositide 3-kinase/AKT signaling cascade. Cancer Sci. Sep. 2012;103(9):1640-50. doi: 10.1111/j.1349-7006.2012.02367.x. Epub Aug. 8, 2012.
Xu et al., The role of WDR5 in silencing human fetal globin gene expression. Haematologica. Nov. 2012;97(11):1632-40. doi: 10.3324/haematol.2012.061937. Epub Jun. 11, 2012.
Zheng et al., Arginine methylation-dependent reader-writer interplay governs growth control by E2F-1. Mol Cell. Oct. 10, 2013;52(1):37-51. doi: 10.1016/j.molcel.2013.08.039. Epub Sep. 26, 2013.
Feki et al., Mutational spectrum of p53 mutations in primary breast and ovarian tumors. Crit Rev Oncol Hematol. Nov. 2004;52(2):103-16.
Rödicker et al., p73 is effective in p53-null pancreatic cancer cells resistant to wild-type TP53 gene replacement. Cancer Res. Jun. 1, 2003;63(11):2737-41.
Silverman, The Organic Chemistry of Drug Design and Drug Action. Elsevier. 2004;29-32.
Extended European Search Report for Application No. EP 18161573.3 dated Oct. 5, 2018.
CAS Registry Nos. 1390524-87-4, 1390490-16-0, 1390364-38-1, 1390262-63-1, 1389804-10-7, 1389608-63-2, 1389477-08-0, 1389191-79-0, 1389186-88-2, 1389150-41-7, 1389143-93-4, 1389138-17-3, 1388976-86-0, 1388976-44-0, 1388908-64-2, 1388701-97-0, 1388690-94-5, 1388642-81-6, 1388576-16-6, 1388555-08-5, 1388432-00-5, 1388397-52-1, 1388369-92-3, 1388367-52-9, 1387845-06-8, 1387782-64-0, 1387456-55-4, 1387169-74-5, 1387110-73-7, 1387108-14-6, 1386827-14-0, 1386608-97-4, 1386280-12-1, 1386280-07-4, 1386148-41-9, 1386010-87-2, 1322579-97-4, 1322145-39-0, 1321571-71-4, 1320022-45-4, 1320021-13-3, 1319342-38-5, 1319121-25-9, 1319002-83-9, 1318997-32-8, 1318913-98-2, 1318883-46-3, 1318644-07-3, 1317982-41-4, 1317968-41-4, 1317886-59-1, 1317589-67-5, 1317515-43-7, 1317334-82-9, 1316369-94-4, 1316197-59-7, 1302193-68-5, 1288518-05-7, 1281089-87-9, 1280921-87-0, 1223357-53-6, 1223349-33-4, 1223239-90-4, 1223228-05-4, 1223214-63-8, 1222970-06-0, 1211677-43-8, 1208850-42-3, 1197943-03-5, 1197564-92-3, 1181543-32-7, 1147700-86-4, 1147642-86-1, 1445676-20-9, 1445676-11-8, 1445163-85-8, 1444874-40-1, 1444830-50-5, 1444828-93-6, 1444693-38-2, 1444637-79-9, 1436034-24-0, 1427932-67-9, 1385797-51-2, 1385797-47-6, and 1385614-49-2. 53 pages.
Collins et al., Macrocyclizations for medicinal chemistry: synthesis of druglike macrocycles by high-concentration Ullmann coupling. J Org Chem. Dec. 21, 2012;77(24):11079-90. doi: 10.1021/jo302089f. Epub Dec. 6, 2012. PubMed PMID: 23167628.
Guo et al., Development of benzophenone-alkyne bifunctional sigma receptor ligands. Chembiochem. Oct. 15, 2012;13(15):2277-89. doi: 10.1002/cbic.201200427. Epub Sep. 23, 2012.
Iida et al., 1.Total synthesis of .+-.-isocyclocelabenzene. J Org Chem. 1986;51(24):4701-4703. DOI: 10.1021/jo00374a035.
Li et al., Novel peptidyl alpha-keto amide inhibitors of calpains and other cysteine proteases. J Med Chem. Sep. 27, 1996;39(20):4089-98. PubMed PMID: 8831774.
Mokrosz et al., 1,2,3,4-tetrahydroisoquinoline derivatives: a new class of 5-HT1A receptor ligands. Bioorg Med Chem. Feb. 1999;7(2):287-95. PubMed PMID: 10218820.
Schultz et al., Total Synthesis of the Spermidine Alkaloid (+)-(9S,13S)-Isocyclocelabenzine. Tetrahedron. Nov. 1996;52(45):14189-14198. doi:10.1016/0040-4020(96)00872-1.
Vooturi et al., Solution-phase parallel synthesis of novel membrane-targeted antibiotics. Supporting Information. 63 pages.
Zajdel et al., Solid-phase synthesis of aryl-alkylamine derivatives using protected aminoalcohol building blocks on SynPhase lanterns. QSAR Comb Sci. 2007;26(2):215-9.

\* cited by examiner

Maver-1: SDMA ICW IC50

SEQUENCE LISTING

<160> NUMBER OF SEQ ID NOS: 2

<210> SEQ ID NO 1

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
tgtggtggag atcttttggg                                           20

<210> SEQ ID NO 2
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 2
gcagtgtggg gatatcgt                                             18
```

PRMT5 INHIBITORS AND USES THEREOF

RELATED APPLICATIONS

This application is a national stage filing under 35 U.S.C. § 371 of international PCT application, PCT/US2015/043679, filed Aug. 4, 2015, which claims the benefit under 35 U.S.C. § 119(e) of U.S. provisional applications, U.S. Ser. No. 62/194,459, filed Jul. 20, 2015, U.S. Ser. No. 62/148,713, filed Apr. 16, 2015, and U.S. Ser. No. 62/033,095, filed Aug. 4, 2014, the entire contents of each of which are incorporated herein by reference.

BACKGROUND

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., PRMT5), many of which are associated with specific genetic alterations that can cause human disease.

SUMMARY

Aspects of the disclosure relate to methods of treating cancer using one or more PRMT5 inhibitors. Disease-associated chromatin-modifying enzymes (e.g., PRMT5) play a role in diseases such as proliferative disorders, including cancer.

In some embodiments, aspects of the disclosure provide methods for treating cancer by administering a PRMT5 inhibitor (e.g., a composition comprising a PRMT5 inhibitor) to a subject having cancer. In some embodiments, the cancer is lymphoma (e.g., mantle cell lymphoma). In some embodiments, the cancer is breast cancer (e.g., triple-negative breast cancer). In some embodiments, the cancer is pancreatic cancer. In some embodiments, the cancer is multiple myeloma (MM). In some embodiments, the cancer is acute myeloid lymphoma (AML). In some embodiments, the cancer is colon cancer. In some embodiments, the cancer is not characterized by a p53 deficiency (e.g., the cancer is a p53 positive cancer).

Non-limiting examples of PRMT5 inhibitors that are useful as described herein include compounds of Formula A-F as described below.

In some embodiments, the disclosure provides a compound of Formula A:

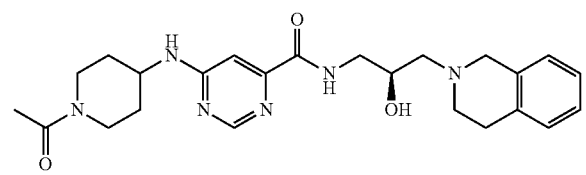

Formula A
or a pharmaceutically acceptable salt thereof. In some embodiments the disclosure provides a succinate salt of Formula A. In some embodiments, the disclosure provides a benzoate salt of Formula A.

In some embodiments, the disclosure provides a compound of Formula B:

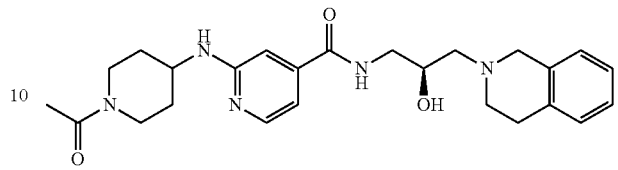

Formula B
or a pharmaceutically acceptable salt thereof. In some embodiments the disclosure provides a succinate salt of Formula B. In some embodiments, the disclosure provides a benzoate salt of Formula B.

In some embodiments, the disclosure provides a compound of Formula C:

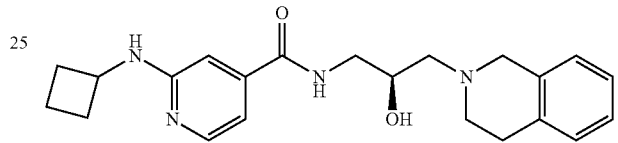

Formula C
or a pharmaceutically acceptable salt thereof. In some embodiments the disclosure provides a succinate salt of Formula C. In some embodiments, the disclosure provides a benzoate salt of Formula C.

In some embodiments, the disclosure provides a compound of Formula D:

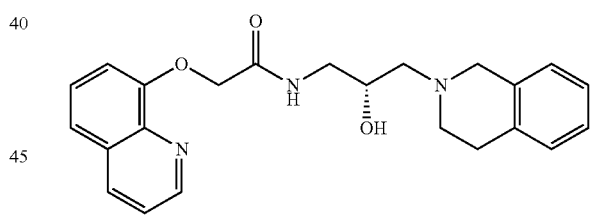

Formula D
or a pharmaceutically acceptable salt thereof. In some embodiments the disclosure provides a succinate salt of Formula D. In some embodiments, the disclosure provides a benzoate salt of Formula D.

In some embodiments, the disclosure provides a compound of Formula E:

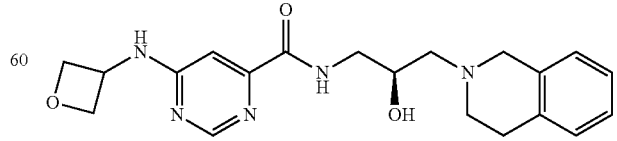

Formula E
or a pharmaceutically acceptable salt thereof. In some embodiments the disclosure provides a succinate salt of Formula E. In some embodiments, the disclosure provides a benzoate salt of Formula E.

In some embodiments, the disclosure provides a compound of Formula F:

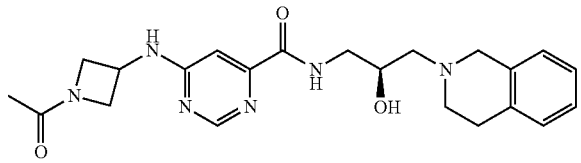

Formula F or a pharmaceutically acceptable salt thereof. In some embodiments the disclosure provides a succinate salt of Formula F. In some embodiments, the disclosure provides a benzoate salt of Formula F.

Other non-limiting examples of PRMT5 inhibitors are disclosed in the following published patent applications WO2011/079236, WO2014/100695, WO2014/100716, WO2014/100719, WO2014/100730, WO2014/100764, and WO2014/100734, and U.S. Provisional Application Nos. 62/017,097 and 62/017,055, the disclosures of each of which are incorporated herein by reference (e.g., the generic and specific compounds described in these patent applications are incorporated herein by reference and can be used to treat cancer as described herein). In some embodiments, the PRMT5 inhibitor is a nucleic acid (e.g., a siRNA). siRNAs against PRMT5 are described for instance in Mol Cancer Res. 2009 April; 7(4): 557-69, and Biochem J. 2012 Sep. 1; 446(2):235-41.

In some embodiments, the method of treating cancer in a subject comprises administering a composition comprising a PRMT5 inhibitor to the subject, wherein treatment with the PRMT5 inhibitor inhibits tumor growth of the cancer by more than about 25%, more than about 50%, more than about 75%, more than about 90% (e.g., 25%-50%, 50%-75%, 75%-90%, or 90%-100% for example). In some embodiments, the PRMT5 inhibitor is administered in an amount sufficient to inhibit tumor growth of the cancer by about 50% or more.

In some embodiments, the method of treating cancer in a subject comprises administering a composition comprising a PRMT5 inhibitor to the subject, wherein methyl mark of the cancer is reduced more than about 50%, more than about 75%, more than about 80% (e.g., 50%-75%, 50%-80%, 80%-90%, 80%-100%, or 90%-100% for example). In some embodiments, the PRMT5 inhibitor is administered in an amount sufficient to reduce the methyl mark of the cancer by about 80% or more.

In some embodiments, the method of treating cancer in a subject comprises administering a composition comprising a PRMT5 inhibitor to the subject, wherein body weight loss of the subject is less than about 20%, less than about 15%, less than about 10%, less than about 8%, or less than about 5% (e.g., 20%-10%, 10%-5%, about 8%, about 6%, about 5%, about 4%, or 5%-0%, for example). Accordingly, in some embodiments, the method of treating cancer in a subject comprises administering a composition comprising a PRMT5 inhibitor to the subject in an amount wherein body weight loss of the subject is about 8% or less. In some embodiments, the method of treating cancer in a subject comprises administering a composition comprising a PRMT5 inhibitor to the subject in an amount wherein body weight loss of the subject is about 6% or less. In some embodiments, the method of treating cancer in a subject comprises administering a composition comprising a PRMT5 inhibitor to the subject in an amount wherein body weight loss of the subject is about 4% or less.

In some aspects, the disclosure relates to a method of identifying a subject having a cancer that is sensitive to treatment with a PRMT5 inhibitor, the method comprising obtaining a biological sample from the subject; detecting the presence or absence of p53 (e.g., performing an assay to detect the presence or absence of p53); and, identifying the subject as having a cancer that is sensitive to treatment with a PRMT5 inhibitor if p53 is present (e.g., is present at a normal level) in the sample. In some embodiments, the method further comprises administering to the subject a composition comprising a PRMT5 inhibitor.

In some aspects, the disclosure relates to a method of identifying a subject having a cancer that is not sensitive to treatment with a PRMT5 inhibitor, the method comprising obtaining a biological sample from the subject; detecting the presence or absence of p53 (e.g., performing an assay to detect the presence or absence of p53); and, identifying the subject as having a cancer that is not sensitive to treatment with a PRMT5 inhibitor if p53 is absent from the sample. In some embodiments, the method further comprises administering to the subject a treatment regimen that does not include a PRMT5 inhibitor.

In some embodiments, the composition comprises a PRMT5 inhibitor having one of the following formulas: Formula A, Formula B, Formula C, Formula D, Formula E, or Formula F.

In some embodiments, two or more PRMT5 inhibitors are administered to the subject.

In some embodiments, the subject also is being treated with an additional therapeutic agent.

In some embodiments, the subject is diagnosed as having cancer prior to the initiation of treatment. In some embodiments, the subject has previously been treated for cancer.

Other features and advantages of the invention will be apparent from the following detailed description and claims.

DETAILED DESCRIPTION

Figure 1:
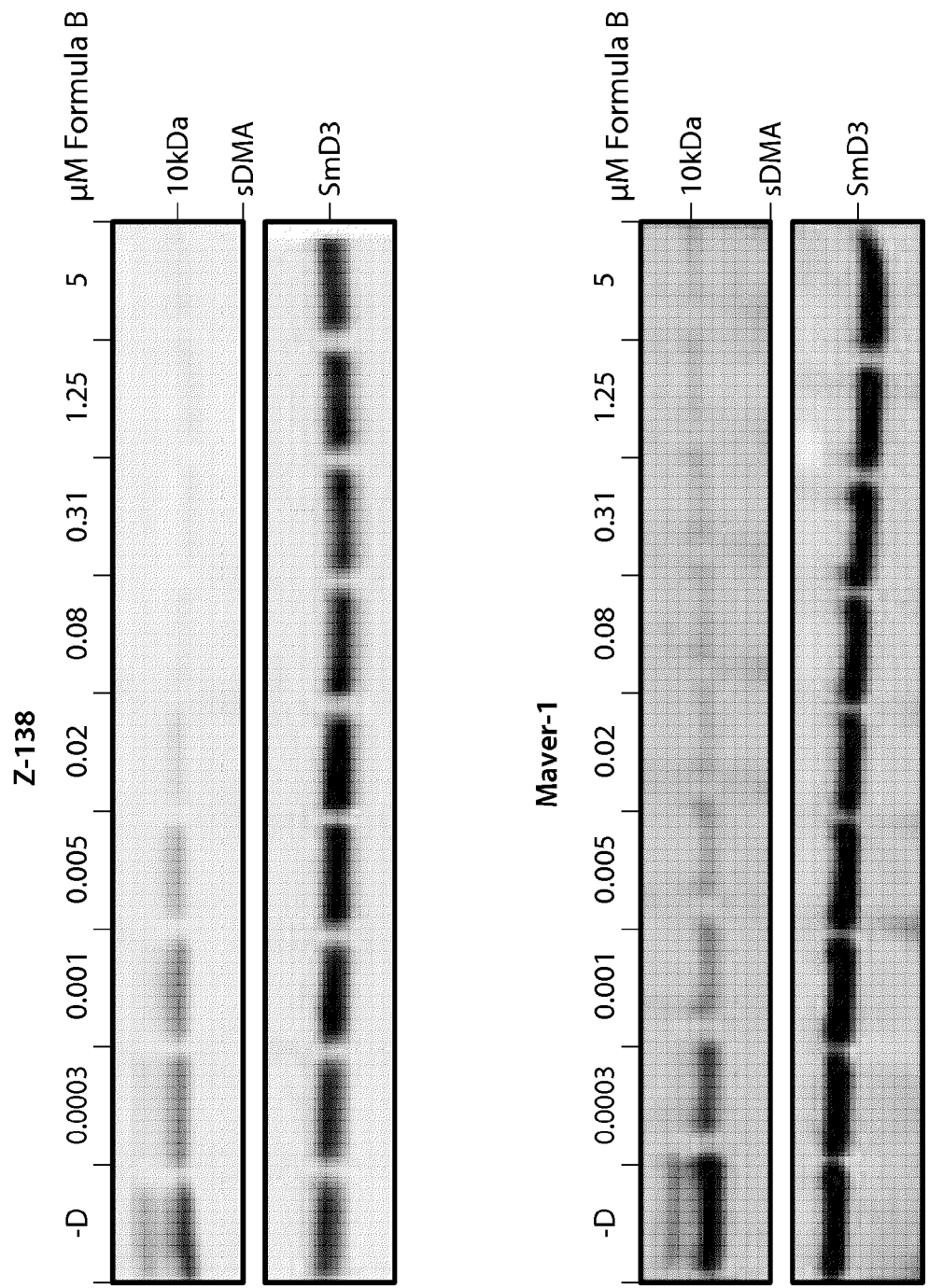
FIG. 1 shows sDMA western blots of Formula B-treated Z-138 and Maver-1 cells on day 4.

Aspects of the disclosure provide methods for treating cancer using one or more PRMT5 inhibitors. In some embodiments, one or more PRMT5 inhibitors are administered to a subject having cancer. In some embodiments, the subject is diagnosed as having cancer prior to treatment with a PRMT5 inhibitor. In some embodiments, the subject has lymphoma, breast cancer, or pancreatic cancer. In some embodiments, the subject is diagnosed as having lymphoma, breast cancer, or pancreatic cancer prior to treatment with a PRMT5 inhibitor. However, it should be appreciated that a subject having (e.g., diagnosed as having) one or more other cancers also can be treated with a PRMT5 inhibitor.

In some embodiments, one or more PRMT5 inhibitors are administered alone to treat or prevent cancer (e.g., to prevent or reduce the risk of cancer recurrence). In some embodiments, one or more PRMT5 inhibitors are provided in addition to one or more additional therapeutic agents (e.g., chemotherapeutic agents and/or hormonal treatments) and/or additional therapeutic treatment (e.g., radiation and/or surgery).

It should be appreciated that a PRMT5 inhibitor can be provided in a pharmaceutical composition along with one or more pharmaceutically acceptable solvents and/or buffers and/or salts. In some embodiments, a PRMT5 inhibitor is provided in a dry form (e.g., powder, solid, or crystalline form). In some embodiments, a PRMT5 inhibitor is provided in a liquid form (e.g., solution or suspension). However, it should be appreciated that a PRMT5 inhibitor can be provided in other forms as described herein.

Protein arginine methyltransferase 5 (PRMT5) catalyzes the addition of two methyl groups to the two ω-guanidino nitrogen atoms of arginine, resulting in ω-NG, N'G symmetric dimethylation of arginine (sDMA) of the target protein. PRMT5 functions in the nucleus as well as in the cytoplasm, and its substrates include histones, spliceosomal proteins, transcription factors (See e.g., Sun et al., 2011, PNAS 108: 20538-20543). PRMT5 generally functions as part of a protein complex. While the protein complexes of PRMT5 can have a variety of components, they generally include the protein MEP50 (methylosome protein 50). In addition, PRMT5 acts in conjunction with cofactor SAM (S-adenosyl methionine).

PRMT5 is an attractive target for modulation given its role in the regulation of diverse biological processes. As described herein, PRMT5 is involved in processes associated with cancer cell growth and the inhibition of PRMT5 can slow or stop cancer cell growth and/or lead to cancer cell death, e.g., apoptosis. It has been found that compounds described herein, and pharmaceutically acceptable salts and compositions thereof, are effective inhibitors of PRMT5 that are useful for treating cancer.

Non-limiting examples of PRMT5 inhibitors that are useful as described herein include compounds of Formulae 1-5 and A-F as described below.

As generally described above, provided herein are compounds useful as PRMT5 inhibitors. In some embodiments, the present disclosure provides a compound of Formula (1):

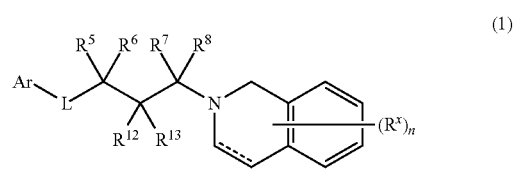

or a pharmaceutically acceptable salt thereof, wherein:

===== represents a single or double bond;

$R^{12}$ is hydrogen, halogen, or optionally substituted $C_{1-3}$alkyl;

R$^{13}$ is hydrogen, halogen, optionally substituted C$_{1-3}$alkyl, —NR$^{A1}$R$^{A2}$, or —OR$^1$;

R$^{A1}$ and R$^{A2}$ are each independently hydrogen, optionally substituted C$_{1-3}$ alkyl, optionally substituted acyl, or a nitrogen protecting group, or R$^{A1}$ and R$^{A2}$ are taken together with the intervening nitrogen atom to form an optionally substituted 3-6 membered heterocyclic ring;

R$^1$ is hydrogen, R$^z$, or —C(O)R$^z$, wherein R$^z$ is optionally substituted C$_{1-6}$ alkyl;

L is —N(R)C(O)—, —C(O)N(R)—, —N(R)C(O)N(R)—, —N(R)C(O)O—, or —OC(O)N(R)—;

each R is independently hydrogen or optionally substituted C$_{1-6}$ aliphatic;

Ar is a monocyclic or bicyclic aromatic ring having 0-4 heteroatoms independently selected from nitrogen, oxygen, and sulfur, wherein Ar is substituted with 0, 1, 2, 3, 4, or 5 R$^y$ groups, as valency permits; or Ar is a monocyclic or bicyclic heterocyclic ring having 1-4 heteroatoms independently selected from nitrogen, oxygen, and sulfur, wherein Ar is substituted with 0, 1, 2, 3, 4, or 5 R$^y$ groups, as valency permits;

each R$^y$ is independently selected from the group consisting of halo, —CN, —NO$_2$, optionally substituted aliphatic, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$;

each R$^A$ is independently selected from the group consisting of hydrogen, optionally substituted aliphatic, optionally substituted carbocyclyl, optionally substituted heterocyclyl, optionally substituted aryl, and optionally substituted heteroaryl;

each R$^B$ is independently selected from the group consisting of hydrogen, optionally substituted aliphatic, optionally substituted carbocyclyl, optionally substituted heterocyclyl, optionally substituted aryl, and optionally substituted heteroaryl, or two R$^B$ groups are taken together with their intervening atoms to form an optionally substituted heterocyclic ring;

R$^5$, R$^6$, R$^7$, and R$^8$ are each independently hydrogen, halo, or optionally substituted aliphatic;

each R$^x$ is independently selected from the group consisting of halo, —CN, optionally substituted aliphatic, —OR', and —N(R")$_2$;

R' is hydrogen or optionally substituted aliphatic;

each R" is independently hydrogen or optionally substituted aliphatic, or two R" are taken together with their intervening atoms to form a heterocyclic ring; and n is 0, 1, 2, 3, 4, 5, 6, 7, 8, 9, or 10, as valency permits.

In certain embodiments, provided is a compound of Formula (2):

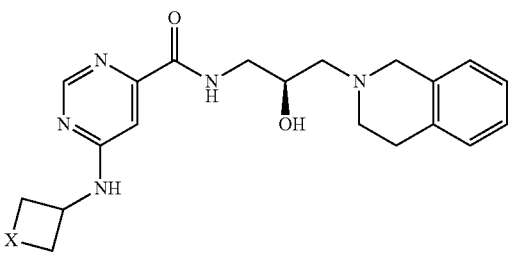

(2)

or a pharmaceutically acceptable salt thereof, wherein X is —C(R$^{XC}$)$_2$—, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl.

In certain embodiments, provided is a compound of Formula (3):

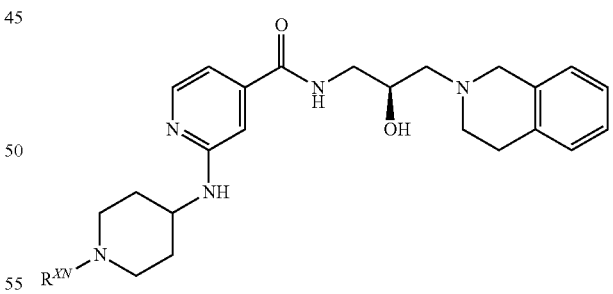

(3)

or a pharmaceutically acceptable salt thereof, wherein R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl.

In certain embodiments, provided is a compound of Formula (4):

(4)

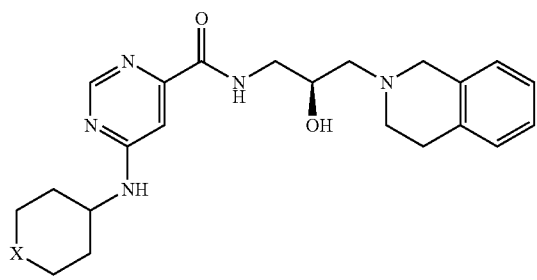

or a pharmaceutically acceptable salt thereof, wherein X is —C(R$^{XC}$)$_2$—, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl.

In certain embodiments, provided is a compound of Formula (5):

(5)

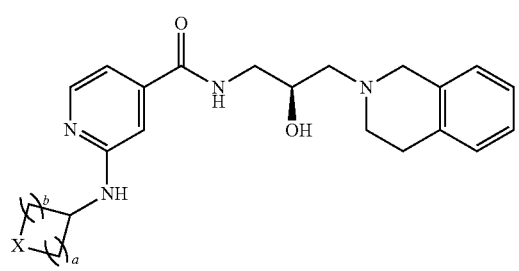

or a pharmaceutically acceptable salt thereof, wherein each instance of a and b is independently 1 or 2, and X is —C(R$^{XC}$)$_2$—, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl.

In some embodiments, the disclosure provides a compound of Formula A:

Formula A

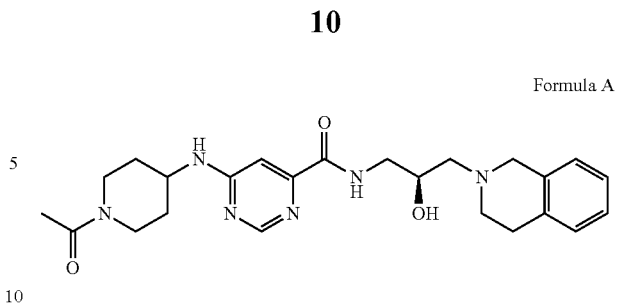

or a pharmaceutically acceptable salt thereof. In some embodiments the disclosure provides a succinate salt of Formula A. In some embodiments, the disclosure provides a benzoate salt of Formula A.

In some embodiments, the disclosure provides a compound of Formula B:

Formula B

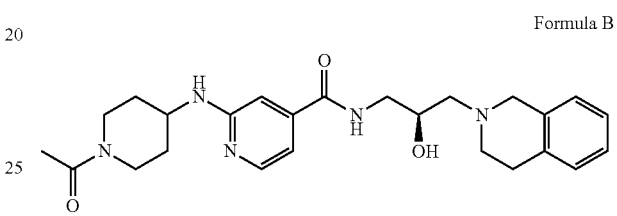

or a pharmaceutically acceptable salt thereof. In some embodiments the disclosure provides a succinate salt of Formula B. In some embodiments, the disclosure provides a benzoate salt of Formula B.

In some embodiments, the disclosure provides a compound of Formula C:

Formula C

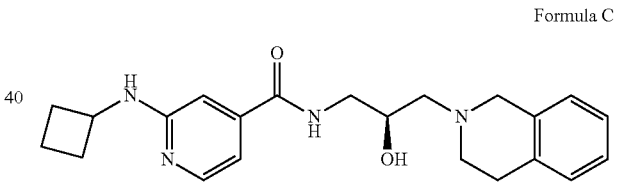

or a pharmaceutically acceptable salt thereof. In some embodiments the disclosure provides a succinate salt of Formula C. In some embodiments, the disclosure provides a benzoate salt of Formula C.

In some embodiments, the disclosure provides a compound of Formula D:

Formula D

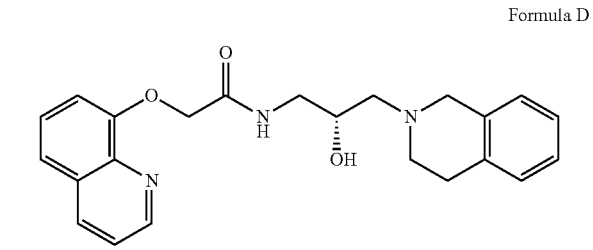

or a pharmaceutically acceptable salt thereof. In some embodiments the disclosure provides a succinate salt of Formula D. In some embodiments, the disclosure provides a benzoate salt of Formula D.

In some embodiments, the disclosure provides a compound of Formula E:

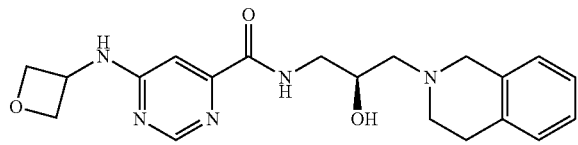

Formula E or a pharmaceutically acceptable salt thereof. In some embodiments the disclosure provides a succinate salt of Formula E. In some embodiments, the disclosure provides a benzoate salt of Formula E.

In some embodiments, the disclosure provides a compound of Formula F:

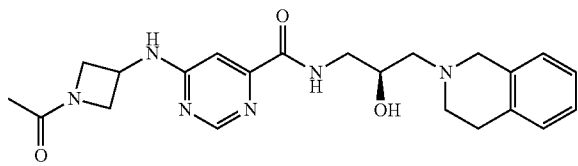

Formula F or a pharmaceutically acceptable salt thereof. In some embodiments the disclosure provides a succinate salt of Formula F. In some embodiments, the disclosure provides a benzoate salt of Formula F.

Other non-limiting examples of PRMT5 inhibitors are disclosed in the following published patent applications WO2011/079236, WO2014/100695, WO2014/100716, WO2014/100719, WO2014/100730, WO2014/100764, and WO2014/100734, and U.S. Provisional Application Nos. 62/017,097 and 62/017,055, the disclosures of each of which are incorporated herein by reference (e.g., the generic and specific compounds described in these patent applications are incorporated herein by reference and can be used to treat cancer as described herein). In some embodiments, the PRMT5 inhibitor is a nucleic acid (e.g., a siRNA). siRNAs against PRMT5 are described for instance in Mol Cancer Res. 2009 April; 7(4): 557-69, and Biochem J. 2012 Sep. 1; 446(2):235-41.

In some embodiments, methods of treating a proliferative disorder such as cancer (e.g., a lymphoma, for example a mantle cell lymphoma, breast cancer, for example triple negative breast cancer, or pancreatic cancer) are provided which comprise administering to a subject suffering from the cancer an effective amount of a PRMT5 inhibitor compound described herein (e.g., a compound of Formulae (1-5) or (A-F)), or a pharmaceutically acceptable salt thereof, or a pharmaceutical composition thereof. In certain embodiments, one or more compounds described herein are useful for treating lymphoma. In some embodiments, the lymphoma is mantle cell lymphoma (MCL). In some embodiments, the lymphoma is acute myeloid lymphoma (AML). In some embodiments, one or more compounds described herein are useful for treating pancreatic cancer. In some embodiments, one or more compounds described herein are useful for treating breast cancer. In some embodiments, the breast cancer is estrogen receptor negative (ER−). In some embodiments, the breast cancer is progesterone receptor negative (PR−). In some embodiments, the breast cancer is HER2 negative. In some embodiments, the breast cancer is ER− and PR−. In some embodiments, the breast cancer is ER− and HER2 negative. In some embodiments, the breast cancer is PR− and HER2 negative. In some embodiments, the breast cancer is estrogen receptor negative, progesterone receptor negative and HER2 negative, also referred to herein as "triple negative breast cancer". In some embodiments, the breast cancer is HER2 positive, estrogen receptor positive, and/or progesterone receptor positive. For example, in some embodiments, the breast cancer is HER2 and estrogen receptor positive. In some embodiments, the breast cancer is HER2 and progesterone receptor positive. In some embodiments, the breast cancer is estrogen and progesterone receptor positive. In some embodiments, a breast cancer can be a lobular carcinoma in situ (LCIS), a ductal carcinoma in situ (DCIS), an invasive ductal carcinoma (IDC), inflammatory breast cancer, Paget disease of the nipple, Phyllodes tumor, Angiosarcoma, adenoid cystic carcinoma, low-grade adenosquamous carcinoma, medullary carcinoma, mucinous carcinoma, papillary carcinoma, tubular carcinoma, metaplastic carcinoma, micropapillary carcinoma, mixed carcinoma, or another breast cancer type. In some embodiments, one or more compounds described herein are useful for treating multiple myeloma (MM). In some embodiments, one or more compounds described herein are useful for treating cancer that is not characterized by a p53 deficiency (e.g., the cancer is a p53 positive cancer).

A "subject" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), rodents (e.g., rats and/or mice), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutically effective and prophylactically effective amounts for therapeutic and prophylactic treatments.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "methyltransferase" represents transferase class enzymes that are able to transfer a methyl group from a donor molecule to an acceptor molecule, e.g., an amino acid residue of a protein or a nucleic base of a DNA molecule. Methyltransferases typically use a reactive methyl group bound to sulfur in S-adenosyl methionine (SAM) as the methyl donor. In some embodiments, a methyltransferase described herein is a protein methyltransferase. In some embodiments, a methyltransferase described herein is a histone methyltransferase. Histone methyltransferases (HMT) are histone-modifying enzymes, (including histone-lysine N-methyltransferase and histone-arginine N-methyltransferase), that catalyze the transfer of one or more methyl groups to lysine and arginine residues of histone proteins. In certain embodiments, a methyltransferase described herein is a histone-arginine N-methyltransferase.

In certain embodiments, a provided compound inhibits PRMT5. In certain embodiments, a provided compound inhibits wild-type PRMT5. In certain embodiments, a provided compound inhibits a mutant PRMT5. In certain embodiments, a provided compound inhibits PRMT5, e.g., as measured in an assay described herein. In certain embodiments, the PRMT5 is from a human. In certain embodiments, a provided compound inhibits PRMT5 at an $IC_{50}$ less than or equal to 10 µM. In certain embodiments, a provided compound inhibits PRMT5 at an $IC_{50}$ less than or equal to 1 µM. In certain embodiments, a provided compound inhibits PRMT5 at an $IC_{50}$ less than or equal to 0.1 µM. In certain embodiments, a provided compound inhibits PRMT5 in a cell at an $EC_{50}$ less than or equal to 10 µM. In certain embodiments, a provided compound inhibits PRMT5 in a cell at an $EC_{50}$ less than or equal to 1 µM. In certain embodiments, a provided compound inhibits PRMT5 in a cell at an $EC_{50}$ less than or equal to 0.1 µM. In certain embodiments, a provided compound inhibits cell proliferation at an $EC_{50}$ less than or equal to 10 µM. In certain embodiments, a provided compound inhibits cell proliferation at an $EC_{50}$ less than or equal to 1 µM. In certain embodiments, a provided compound inhibits cell proliferation at an $EC_{50}$ less than or equal to 0.1 µM. In some embodiments, a provided compound is selective for PRMT5 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective for PRMT5 relative to one or more other methyltransferases.

The present disclosure provides pharmaceutical compositions comprising a compound described herein, e.g., a compound of Formulae (1-5) or (A-F), or a pharmaceutically acceptable salt thereof, as described herein, and optionally a pharmaceutically acceptable excipient. It will be understood by one of ordinary skill in the art that the compounds described herein, or salts thereof, may be present in various forms, such as hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting PRMT5. In certain embodiments, the effective amount is an amount effective for treating a PRMT5-mediated disorder (e.g., a PRMT-5 mediated cancer). In certain embodiments, the effective amount is a prophylactically effective amount. In certain embodiments, the effective amount is an amount effective to prevent a PRMT5-mediated disorder (e.g., a PRMT-5 mediated cancer). In certain embodiments, the effective amount is an amount sufficient to treat cancer (e.g., lymphoma, for example mantle cell lymphoma, breast cancer, for example triple negative breast cancer, or pancreatic cancer).

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, quaternary salts.

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

In some embodiments, two or more PRMT5 inhibitors described herein (e.g., two or more compounds of Formulae (1-5) or (A-F)) can be used to treat a subject. For example, a first PRMT5 inhibitor compound or composition can be administered concurrently with, prior to, or subsequent to, one or more additional PRMT5 inhibitor compounds or compositions. In some embodiments, a composition comprises a mixture of two or more PRMT5 inhibitors described herein.

In certain embodiments, one or more PRMT5 inhibitor compounds or compositions described herein can be administered concurrently with, prior to, or subsequent to, one or more additional therapeutically active agents (e.g., a therapeutically active agent that is not a compound of Formulae (1-5) or (A-F), or a therapeutically active agent that is not a PRMT5 inhibitor).

In general, each PRMT5 inhibitor and/or other agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

For example, the treatment methods described herein can be administered in conjunction with chemotherapy, radiation therapy, and/or a cytostatic agent. The treatment methods described herein are administered in conjunction with anti-VEGF or anti-angiogenic factor, and/or p53 reactivation agent. Examples of cancer chemotherapeutic agents include, but are not limited to, irinotecan (CPT-11); erlotinib; gefitinib (Iressa®); imatinib mesylate (Gleevec®); oxalipatin; anthracyclins-idarubicin and daunorubicin; doxorubicin; alkylating agents such as melphalan and chlorambucil; cis-platinum, methotrexate, and alkaloids such as vindesine and vinblastine. A cytostatic agent is any agent capable of inhibiting or suppressing cellular growth and multiplication. Examples of cytostatic agents used in the treatment of cancer are paclitaxel, 5-fluorouracil, 5-fluorouridine, mitomycin-C, doxorubicin, and zotarolimus. Other cancer therapeutics includes inhibitors of matrix metalloproteinases such as marimastat, growth factor antagonists, signal transduction inhibitors and protein kinase C inhibitors.

In another embodiment, the pharmaceutical compositions described herein are administered in conjunction with an anti-VEGF agent. Some examples of anti-VEGF agents include bevacizumab (Avastin®), VEGF Trap, CP-547,632, AG13736, AG28262, SU5416, SU11248, SU6668, ZD-6474, ZD4190, CEP-7055, PKC 412, AEE788, AZD-2171, sorafenib, vatalanib, pegaptanib octasodium, IM862, DC101, angiozyme, Sirna-027, caplostatin, neovastat, ranibizumab, thalidomide, and AGA-1470, a synthetic analog of fumagillin (alternate names: Amebacilin, Fugillin, Fumadil B, Fumadil) (A. G. Scientific, catalog #F1028), an angio-inhibitory compound secreted by *Aspergillus* fumigates.

As used herein the term "anti-VEGF agent" refers to any compound or agent that produces a direct effect on the signaling pathways that promote growth, proliferation and survival of a cell by inhibiting the function of the VEGF protein, including inhibiting the function of VEGF receptor proteins. The term "agent" or "compound" as used herein means any organic or inorganic molecule, including modified and unmodified nucleic acids such as antisense nucleic acids, RNAi agents such as siRNA or shRNA, peptides, peptidomimetics, receptors, ligands, and antibodies. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and —R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (IEterna Zentaris Inc; Quebec City, Calif.) and combinations thereof.

In some embodiments, one or more PRMT5 inhibitor compounds or compositions described herein can be administered concurrently with, prior to, or subsequent to, one or more additional therapeutically active agents (e.g., a therapeutically active agent that is not a compound of Formulae (1-5) or (A-F), or a therapeutically active agent that is not a PRMT5 inhibitor) that are effective in treating breast cancer. Exemplary compounds include but are not limited to: Abitrexate (Methotrexate), Abraxane® (Paclitaxel Albumin-stabilized Nanoparticle Formulation), Ado-Trastuzumab Emtansine, Adriamycin PFS® (Doxorubicin Hydrochloride), Adriamycin RDF® (Doxorubicin Hydrochloride), Adrucil® (Fluorouracil), Afinitor® (Everolimus), Anastrozole, Aredia® (Pamidronate Disodium), Arimidex® (Anastrozole), Aromasin (Exemestane), Capecitabine, Clafen® (Cyclophosphamide), Cyclophosphamide, Cytoxan® (Cyclophosphamide), Docetaxel, Doxorubicin Hydrochloride, Efudex® (Fluorouracil), Ellence® (Epirubicin Hydrochloride), Epirubicin Hydrochloride, Everolimus, Exemestane, Fareston® (Toremifene), Faslodex® (Fulvestrant), Femara® (Letrozole), Fluoroplex® (Fluorouracil), Fluorouracil, Folex® (Methotrexate), Folex PFS® (Methotrexate), Fulvestrant, Gemcitabine Hydrochloride, Gemzar® (Gemcitabine Hydrochloride), Goserelin Acetate, Herceptin® (Trastuzumab), Ixabepilone, Ixempra® (Ixabepilone), Kadcyla® (Ado-Trastuzumab Emtansine), Lapatinib Ditosylate, Letrozole, Megace® (Megestrol Acetate), Megestrol Acetate, Methotrexate, Methotrexate LPF® (Methotrexate), Mexate® (Methotrexate), Mexate-AQ® (Methotrexate), Neosar® (Cyclophosphamide), Nolvadex® (Tamoxifen Citrate), Paclitaxel, Paclitaxel Albumin-stabilized Nanoparticle Formulation, Pamidronate Disodium, Perjeta® (Pertuzumab), Pertuzumab, Tamoxifen Citrate, Taxol® (Paclitaxel), Taxotere® (Docetaxel), Trastuzumab, Toremifene, Tykerb® (Lapatinib Ditosylate), Xeloda® (Capecitabine), and Zoladex® (Goserelin Acetate).

In some embodiments, one or more PRMT5 inhibitor compounds or compositions described herein can be administered concurrently with, prior to, or subsequent to, one or more additional therapeutically active agents (e.g., a therapeutically active agent that is not a compound of Formulae (1-5) or (A-F), or a therapeutically active agent that is not a PRMT5 inhibitor) that are effective in treating lymphoma, Non-Hodgkin lymphoma and/or mantle cell lymphoma. Exemplary compounds include but are not limited to: Abitrexate® (Methotrexate), Adcetris® (Brentuximab Vedotin), Adriamycin PFS® (Doxorubicin Hydrochloride), Adriamycin RDF® (Doxorubicin Hydrochloride), Ambochlorin® (Chlorambucil), Amboclorin® (Chlorambucil), Arranon® (Nelarabine), Becenum® (Carmustine), Beleodaq® (Belinostat), Belinostat, Bendamustine Hydrochloride, Bexxar® (Tositumomab and Iodine I 131 Tositumomab), BiCNU® (Carmustine), Blenoxane® (Bleomycin), Bleomycin, Bortezomib, Brentuximab Vedotin, Carmubris® (Carmustine), Carmustine, Chlorambucil, Clafen® (Cyclophosphamide), Cyclophosphamide, Cytoxan® (Cyclophosphamide), Denileukin Diftitox, DepoCyt® (Liposomal Cytarabine), Doxorubicin Hydrochloride, DTIC-Dome® (Dacarbazine), Folex® (Methotrexate), Folex PFS® (Methotrexate), Folotyn® (Pralatrexate), Ibritumomab Tiuxetan, Ibrutinib, Imbruvica® (Ibrutinib), Intron A® (Recombinant Interferon Alfa-2b), Istodax® (Romidepsin), Lenalidomide, Leukeran® (Chlorambucil), Linfolizin® (Chlorambucil), Liposomal Cytarabine, Matulane® (Procarbazine Hydrochloride), Mechlorethamine Hydrochloride, Methotrexate, Methotrexate LPF® (Methotrexate), Mexate® (Methotrexate), Mexate-AQ® (Methotrexate), Mozobil® (Plerixafor), Mustargen® (Mechlorethamine Hydrochloride), Nelarabine, Neosar® (Cyclophosphamide), Ontak® (Denileukin Diftitox), Plerixafor, Pralatrexate, Recombinant Interferon Alfa-2b, Revlimid® (Lenalidomide), Rituxan® (Rituximab), Rituximab, Romidepsin, Tositumomab and Iodine I 131 Tositumomab, Treand® (Bendamustine Hydrochloride), Velban® (Vinblastine Sulfate), Velcade® (Bortezomib), Velsar® (Vinblastine Sulfate), Vinblastine Sulfate, Vincasar PFS® (Vincristine Sulfate), Vincristine Sulfate, Vorinostat, Zevalin® (Ibritumomab Tiuxetan), and Zolinza® (Vorinostat).

In some embodiments, one or more PRMT5 inhibitor compounds or compositions described herein can be administered concurrently with, prior to, or subsequent to, one or more additional therapeutically active agents (e.g., a therapeutically active agent that is not a compound of Formulae (1-5) or (A-F), or a therapeutically active agent that is not a PRMT5 inhibitor) that are effective in treating pancreatic cancer. Exemplary compounds include but are not limited to: Abraxane® (Paclitaxel Albumin-stabilized Nanoparticle Formulation), Adrucil® (Fluorouracil), Afinitor® (Everolimus), Efudex® (Fluorouracil), Erlotinib Hydrochloride, Everolimus, Fluoroplex® (Fluorouracil), Fluorouracil, Gemcitabine Hydrochloride, Gemzar® (Gemcitabine Hydrochloride), Mitomycin C, Mitozytrex® (Mitomycin C), Mutamycin® (Mitomycin C), Paclitaxel Albumin-stabilized Nanoparticle Formulation, Sunitinib Malate, Sutent® (Sunitinib Malate), and Tarceva® (Erlotinib Hydrochloride).

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of PRMT5. In some embodiments, methods of treating PRMT5-mediated disorder in a subject are provided which comprise administering an effective amount of a compound described herein (e.g., a compound of Formulae (1-5) or (A-F)), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from a PRMT5-mediated disorder (e.g., a cancer, for example a lymphoma, breast cancer, or pancreatic cancer). In certain embodiments, the subject is susceptible to a PRMT5-mediated disorder (e.g., a cancer, for example a lymphoma, breast cancer, or pancreatic cancer).

As used herein, the term "PRMT5-mediated disorder" means any disease, disorder, or other pathological condition in which PRMT5 is known to play a role. Accordingly, in some embodiments, the present disclosure relates to treating or lessening the severity of one or more diseases in which PRMT5 is known to play a role.

In some embodiments, provided is a method of inhibiting PRMT5 activity in a subject in need thereof comprising administering to the subject an effective amount of a compound described herein (e.g., a compound of Formulae (1-5) or (A-F)), or a pharmaceutically acceptable salt thereof, or a pharmaceutical composition thereof.

In some embodiments, a provided compound is useful in treating a proliferative disorder, such as cancer. In certain embodiments, the cancer compounds described herein are useful for treating lymphoma. In some embodiments, the lymphoma is mantle cell lymphoma (MCL). In some embodiments, the lymphoma is acute myeloid lymphoma (AML). In some embodiments, the cancer compounds described herein are useful for treating pancreatic cancer. In some embodiments, the cancer compounds described herein are useful for treating multiple myeloma (MM). In some embodiments, the cancer compounds described herein are useful for treating breast cancer. In some embodiments, the breast cancer is estrogen receptor negative (ER−). In some embodiments, the breast cancer is progesterone receptor negative (PR−). In some embodiments, the breast cancer is HER2 negative. In some embodiments, the breast cancer is estrogen receptor negative, progesterone receptor negative and HER2 negative, also referred to herein as "triple negative breast cancer".

In some embodiments, one or more compounds described herein are useful for treating breast cancer. In some embodiments, the breast cancer is estrogen receptor negative (ER–). In some embodiments, the breast cancer is progesterone receptor negative (PR–). In some embodiments, the breast cancer is HER2 negative. In some embodiments, the breast cancer is estrogen receptor negative, progesterone receptor negative and HER2 negative, also referred to herein as "triple negative breast cancer". In some embodiments, a breast cancer can be a lobular carcinoma in situ (LCIS), a ductal carcinoma in situ (DCIS), an invasive ductal carcinoma (IDC), inflammatory breast cancer, Paget disease of the nipple, Phyllodes tumor, Angiosarcoma, adenoid cystic carcinoma, low-grade adenosquamous carcinoma, medullary carcinoma, mucinous carcinoma, papillary carcinoma, tubular carcinoma, metaplastic carcinoma, micropapillary carcinoma, mixed carcinoma, or another breast cancer, including but not limited to triple negative, HER positive, estrogen receptor positive, progesterone receptor positive, HER and estrogen receptor positive, HER and progesterone receptor positive, estrogen and progesterone receptor positive, and HER and estrogen and progesterone receptor positive.

Accordingly, in some embodiments, the method of treating cancer in a subject comprises administering a composition comprising a PRMT5 inhibitor to the subject. In some embodiments, the cancer is lymphoma. In some embodiments, the lymphoma is mantle cell lymphoma. In some embodiments, the cancer is breast cancer. In some embodiments, the breast cancer is triple-negative breast cancer. In some embodiments, the cancer is pancreatic cancer.

In some embodiments, one or more compounds described herein are useful for treating any PRMT5-mediated or PRMT5-responsive proliferative cell disorder, for example a cancer that is PRMT5 responsive.

In some embodiments, a cancer that lacks p53 (e.g., a p53 null cancer) is less sensitive to PRMT5 inhibition than a cancer that is p53 positive. Accordingly, a cancer that is PRMT5 responsive can be a p53 positive cancer. The term "p53 positive" refers to a cancer that does not lack p53 expression and/or activity. In some embodiments, one or more compounds described herein are useful for treating a p53 positive cancer. In some embodiments, a greater amount of one or more compounds described herein may be required to treat a p53 negative cancer (e.g., a p53 null cancer) than a p53 positive cancer.

In some embodiments, the disclosure provides a method for identifying subjects having a cancer that is sensitive to treatment with a PRMT5 inhibitor. In some embodiments, the method comprises obtaining a sample from the subject; detecting the presence or absence of p53; and, identifying the subject as having a cancer that is sensitive to treatment with a PRMT5 inhibitor if p53 is present in the sample. Accordingly, in some embodiments, a subject having a p53 positive cancer is identified as a subject for treatment with a PRMT5 inhibitor. In some embodiments, the method further comprises administering to the subject a composition comprising a PRMT5 inhibitor.

In some embodiments, aspects of the disclosure relate to a method for identifying subjects having a cancer that is insensitive (or that has low sensitivity) to treatment with a PRMT5 inhibitor. In some embodiments, the method comprises obtaining a sample from the subject; detecting the presence or absence of p53; and, identifying the subject as having a cancer that is not sensitive (for example, a cancer that is less sensitive than a p53 positive cancer) to treatment with a PRMT5 inhibitor if p53 is absent from the sample (e.g., if the cancer is a p53 null cancer). In some embodiments, a p53 negative cancer (e.g., a p53 null cancer) is treated with a PRMT5 inhibitor, but a greater amount of PRMT5 inhibitor may be required to treat the p53 negative cancer than a p53 positive cancer. However, in some embodiments, a subject having a p53 negative cancer (e.g., a p53 null cancer) is treated with a therapeutic agent that is not a PRMT5 inhibitor.

By "sample" is meant any biological sample derived from the subject, includes but is not limited to, cells, tissues samples, body fluids (including, but not limited to, mucus, blood, plasma, serum, urine, saliva, and semen), cancer cells, and cancer tissues. Detection of the presence or absence of p53 in the sample may be achieved by any suitable method for detecting p53 nucleic acid or protein, for example, nucleic acid sequencing (e.g., DNA or RNA sequencing), quantitative PCR, Western blotting, etc., or any combination of thereof.

It should be appreciated that in some embodiments, one or more of the compounds described herein may be useful for treating other types of cancer, including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL), follicular lymphoma, chronic lymphocytic leukemia/small lymphocytic lymphoma (CLL/SLL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (e.g., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/ leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, the method of treating cancer in a subject comprises administering a composition comprising a PRMT5 inhibitor to the subject, wherein treatment with the PRMT5 inhibitor inhibits tumor growth of the cancer by more than about 25%, more than about 50%, more than about 75%, more than about 90% (e.g., 25%-50%, 50%-75%, 75%-90%, or 90%-100% for example). In some embodiments, the method of treating cancer in a subject comprises administering a composition comprising a PRMT5 inhibitor to the subject, wherein methyl mark of the cancer is reduced more than about 50%, more than about 75%, more than about 80% (e.g., 50%-75%, 50%-80%, 80%-90%, 80%-100%, or 90%-100% for example). A methyl mark refers to protein methylation, for example a histone methylation (e.g., methylation of one or more lysines and/or arginines of a histone protein), or DNA methylation (e.g., epigenetic DNA methylation, for example methylated CpG sites). In some embodiments, the methyl mark level of a cell is a measure of the extent to which histones are methylated in the cell (e.g., at one or more particular lysine and/or arginine positions).

In some embodiments, the method of treating cancer in a subject comprises administering a composition comprising a PRMT5 inhibitor to the subject, wherein body weight loss of the subject is less than about 20%, less than about 15%, less than about 10%, less than about 8%, or less than about 5% (e.g., 20%-10%, 10%-5%, about 8%, about 6%, about 5%, about 4%, or 5%-0%, for example). Accordingly, in some embodiments, the method of treating cancer in a subject comprises administering a composition comprising a PRMT5 inhibitor to the subject, wherein body weight loss of the subject is about 8% or less. In some embodiments, the method of treating cancer in a subject comprises administering a composition comprising a PRMT5 inhibitor to the subject, wherein body weight loss of the subject is about 6% or less. In some embodiments, the method of treating cancer in a subject comprises administering a composition comprising a PRMT5 inhibitor to the subject, wherein body weight loss of the subject is about 4% or less.

In some aspects, the disclosure relates to the surprising discovery that MDM4 (also known as MDMX) overexpression can attenuate the activity of a PRMT5 inhibitor in a subject. For example, MDM4 overexpression can partially rescue growth/death phenotype induced by a PRMT5 inhibitor in cancer cells (e.g., lymphoma cells). Accordingly, in some embodiments, a method of treating cancer comprises inhibiting MDM4 activity or MDM4 expression concurrently with (e.g., prior to, or simultaneously with, and/or after), the administration of a composition comprising a PRMT5 inhibitor to the subject. MDM4 activity can be inhibited directly (e.g., by administration of a MDM4 inhibitor) or indirectly (e.g., silencing MDM4 expression). Examples of MDM4 inhibitors include SJ-172550 and NSC-207895. In some embodiments silencing of MDM4 expression is achieved by post-transcriptional gene silencing (e.g., RNA interference) or by interfering with an MDM4 transcription factor binding site in the MDM4 gene promoter (e.g., PPAR-alpha, MZF-1, NRF-2, c-Ets-1, TPB, Elk-1, HEN1).

Without wishing to be bound by any theory, it is believed that inhibiting MDM4 activity or MDM4 expression activates tumor-suppressor protein, p53. In some aspects, p53 may also be activated by inhibiting MDM2 activity or MDM2 expression. Accordingly, in some embodiments, a method of treating cancer comprises inhibiting MDM2 activity or MDM2 expression concurrently with (e.g., prior to, or simultaneously with, and/or after), the administration of a composition comprising a PRMT5 inhibitor to the subject. MDM2 activity can be inhibited directly (e.g., by administration of a MDM2 inhibitor) or indirectly (e.g., silencing MDM2 expression). Examples of MDM2 inhibitors include Nutlin-3a, NSC-66811, NSC-652287, and SP-141. In some embodiments, silencing of MDM2 expression is achieved by post-transcriptional gene silencing (e.g., RNA interference) or by interfering with an MDM2 transcription factor binding site in the MDM2 gene promoter (e.g., AP-1).

EXAMPLES

In order that the invention described herein may be more fully understood, the following examples are set forth. It should be understood that these examples are for illustrative purposes only and are not to be construed as limiting this invention in any manner.

Example 1: Materials and Methods

Z-138 Methylation Assay

Z-138 suspension cells were purchased from ATCC (American Type Culture Collection, Manassas, Va.). RPMI/Glutamax medium, penicillin-streptomycin, heat inactivated fetal bovine serum, and D-PBS were purchased from Life Technologies, Grand Island, N.Y., USA. Odyssey blocking buffer, 800CW goat anti-rabbit IgG (H+L) antibody, and Licor Odyssey infrared scanner were purchased from Licor Biosciences, Lincoln, Nebr., USA. Symmetric di-methyl arginine antibody was purchased from EMD Millipore, Billerica, Mass., USA. 16% Paraformaldehyde was purchased from Electron Microscopy Sciences, Hatfield, Pa., USA.

Z-138 suspension cells were maintained in growth medium (RPMI 1640 supplemented with 10% v/v heat inactivated fetal bovine serum and 100 units/mL penicillin-streptomycin) and cultured at 37° C. under 5% $CO_2$.

Cell Treatment, in Cell Western (ICW) for Detection of Symmetric Di-Methyl Arginine and DNA Content.

Z-138 cells were seeded in assay medium at a concentration of 50,000 cells per mL to a 384-well cell culture plate with 50 μL per well. Compound (100 nL) from 384 well source plates was added directly to 384 well cell plate. Plates were incubated at 37° C., 5% $CO_2$ for 96 hours. After four days of incubation, 40 μL of cells from incubated plates were added to poly-d-lysine coated 384 well culture plates (BD Biosciences 356697). Plates were incubated at room temperature for 30 minutes then incubated at 37° C., 5% $CO_2$ for 5 hours. After the incubation, 40 μL per well of 8% paraformaldehyde in PBS (16% paraformaldehyde was diluted to 8% in PBS) was added to each plate and incubated for 30 minutes. Plates were transferred to a Biotek 405 plate washer and washed 5 times with 100 μL per well of wash buffer (1×PBS with 0.1% Triton X-100 (v/v)). Next 30 μL per well of Odyssey blocking buffer were added to each plate and incubated 1 hour at room temperature. Blocking buffer was removed and 20 μL per well of primary antibody was added (symmetric di-methyl arginine diluted 1:100 in Odyssey buffer with 0.1% Tween 20 (v/v)) and plates were incubated overnight (16 hours) at 4° C. Plates were washed 5 times with 100 μL per well of wash buffer. Next 20 μL per well of secondary antibody was added (1:200 800CW goat anti-rabbit IgG (H+L) antibody, 1:1000 DRAQS (Biostatus limited) in Odyssey buffer with 0.1% Tween 20 (v/v)) and incubated for 1 hour at room temperature. The plates were washed 5 times with 100 μL per well wash buffer then 1 time with 100 μL per well of water. Plates were allowed to dry at room temperature then imaged on the Licor Odyssey machine which measures integrated intensity at 700 nm and 800 nm wavelengths. Both 700 and 800 channels were scanned.

Calculations:

First, the ratio for each well was determined by:

$$\left(\frac{\text{symmetric di-methyl Arginine 800 nm value}}{DRAQ5 \text{ 700 nm value}}\right)$$

Each plate included fourteen control wells of DMSO only treatment (minimum inhibition) as well as fourteen control wells for maximum inhibition treated with 3 μM of a reference compound (Background wells). The average of the ratio values for each control type was calculated and used to determine the percent inhibition for each test well in the plate. Reference compound was serially diluted three-fold in DMSO for a total of nine test concentrations, beginning at 3 μM. Percent inhibition was determined and $IC_{50}$ curves were generated using triplicate wells per concentration of compound.

Percent Inhibition =
$$100 - \left(\left(\frac{\text{(Individual Test Sample Ratio)} - \text{(Background Avg Ratio)}}{\text{(Minimum Inhibition Ratio)} - \text{(Background Average Ratio)}}\right) * 100\right)$$

Z-138 Proliferation Assay

Z-138 suspension cells were purchased from ATCC (American Type Culture Collection, Manassas, Va.). RPMI/Glutamax medium, penicillin-streptomycin, heat inactivated fetal bovine serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

Z-138 suspension cells were maintained in growth medium (RPMI 1640 supplemented with 10% v/v heat inactivated fetal bovine serum and cultured at 37° C. under 5% $CO_2$. Under assay conditions, cells were incubated in assay medium (RPMI 1640 supplemented with 10% v/v heat inactivated fetal bovine serum and 100 units/mL penicillin-streptomycin) at 37° C. under 5% $CO_2$.

For the assessment of the effect of compounds on the proliferation of the Z-138 cell line, exponentially growing cells were plated in 384-well white opaque plates at a density of 10,000 cells/ml in a final volume of 50 μl of assay medium. A compound source plate was prepared by performing triplicate nine-point 3-fold serial dilutions in DMSO, beginning at 10 mM (final top concentration of compound in the assay was 20 μM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 5 days at 37° C., 5% $CO_2$, relative humidity >90%.

Cell viability was measured by quantitation of ATP present in the cell cultures, adding 35 μl of Cell Titer Glo® reagent to the cell plates. Luminescence was read in the SpectraMax M5 microplate reader. The concentration of compound inhibiting cell viability by 50% was determined using a 4-parametric fit of the normalized dose response curves.

Example 2: Potency of Formula B on Inhibition of sDMA Methylation in a Panel of MCL Cell Lines MCL cell lines (Z-138, Maver-1, Mino, Granta-519, and Jeko-1) treated with Formula B were harvested on day 4 and whole cell lysates were assessed by western blot using the Pan-di-methyl symmetric arginine antibody, Symmetric Dimethyl Arginine (sDMA). The measurement of the 10 kDa band was used to calculate the methylation $IC_{50}$ values. RNAi data (ELN entry 142-39) suggests that this 10 kDa band is di-methyl symmetric SmD3 however protein ID studies on this 10 kDa band have not been done and as a result it will be labeled in western blots by its molecular weight. Concentration-dependent decreases in the 10 kDa band were observed on day 4 in all cell lines tested with representative western blots shown for Z-138 and Maver-1 cell lines (FIG. 1). Levels of the 10 kDa band from the western blots were quantified by densitometry and ratios of 10 kDa band (postulated to be SmD3me2s) to total SmD3 were calculated to determine the $IC_{50}$s (Table 2, n=1 for all samples). Methylation $IC_{50}$ values were also obtained for Formula A in MCL cell lines, as shown in Table 3.

TABLE 1

Description of Cell Lines used in Long Term Proliferation Assay and Summary of Mantle Lymphoma cell line long-term proliferation $IC_{50}$s and $IC_{90}$s after 11-day treatment with Formula B. N = 1.

| Species | Tissue | Cell Line Name | Supplier | Part Number | Formula B LTP $IC_{50}$ (nM) | Formula B LTP $IC_{90}$ (nM) |
|---|---|---|---|---|---|---|
| Human | Lymphoblast | Z-138 | ATCC | CRL-3001 | 3 | 20 |
| Human | Lymphoblast | Granta-519 | DSMZ | ACC-342 | 12 | 77 |
| Human | Lymphoblast | Jeko-1 | ATCC | CRL-3006 | 14 | 149 |
| Human | Lymphoblast | Maver-1 | ATCC | CRL-3008 | 26 | 73 |
| Human | Lymphoblast | Mino | ATCC | CRL-3000 | 119 | 611 |

TABLE 2

Summary of sDMA western blots of Formula B-treated mantle cell lymphoma cells on day 4. N = 1.

| Cell Line | sDMA Western blot $IC_{50}$ 10 kDa Band (nM) |
|---|---|
| Z-138 | 1 |
| Granta-519 | 0.3 |
| Maver-1 | 0.1 |
| Mino | 2 |
| Jeko-1 | 9.5 |

TABLE 3

Methylation $IC_{50}$s for Formula A and Formula B in MCL cell lines.

| | Formula A | | Formula B | |
|---|---|---|---|---|
| Cell Line | LTP $IC_{50}$ (nM) | sDMA Western $IC_{50}$ (nM) | LTP $IC_{50}$ (nM) | sDMA Western $IC_{50}$ (nM) |
| Z-138 | 5.7 | 14 | 2 | 1 |
| Granta-519 | 4.7 | 2 | 6 | 0.3 |
| Jeko-1 | 11.3 | 8.7 | 5.2 | 9.5 |
| Maver-1 | 32 | 0.3 | 15.3 | 0.1 |
| Mino | 106 | 7 | 64.6 | 2 |

Example 3: ICW Results for Formula B-Treated Z-138 and Maver-1 Cells

Figure 2:
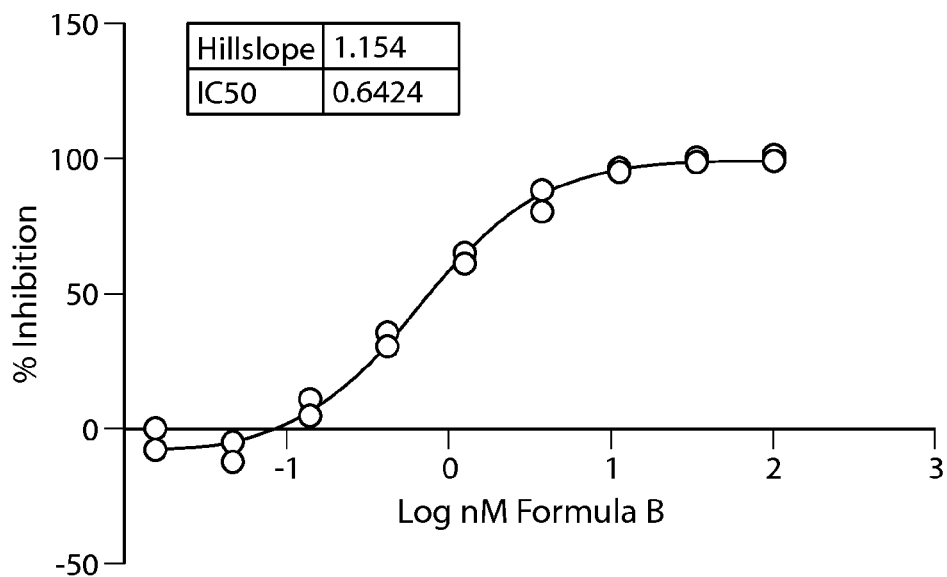
FIG. 2 shows $IC_{50}$ (nM) results from the ICW assay performed in Z-138 cells treated with Formula B. N=1. Percent inhibition was determined and $IC_{50}$ curves were generated using triplicate wells per concentration of compound. $IC_{50}$ values were calculated using GraphPad Prism using a 4-parametric fit of the normalized dose response curves with the top fixed to 100%.

Formula B was tested in the ICW assay with Z-138 cells to determine the $IC_{50}$ of cellular methylation using the SYM11 antibody. An $IC_{50}$ of 0.64 nM was obtained after 4 days of treatment with compound (FIG. 2, n=1).

Figure 3:
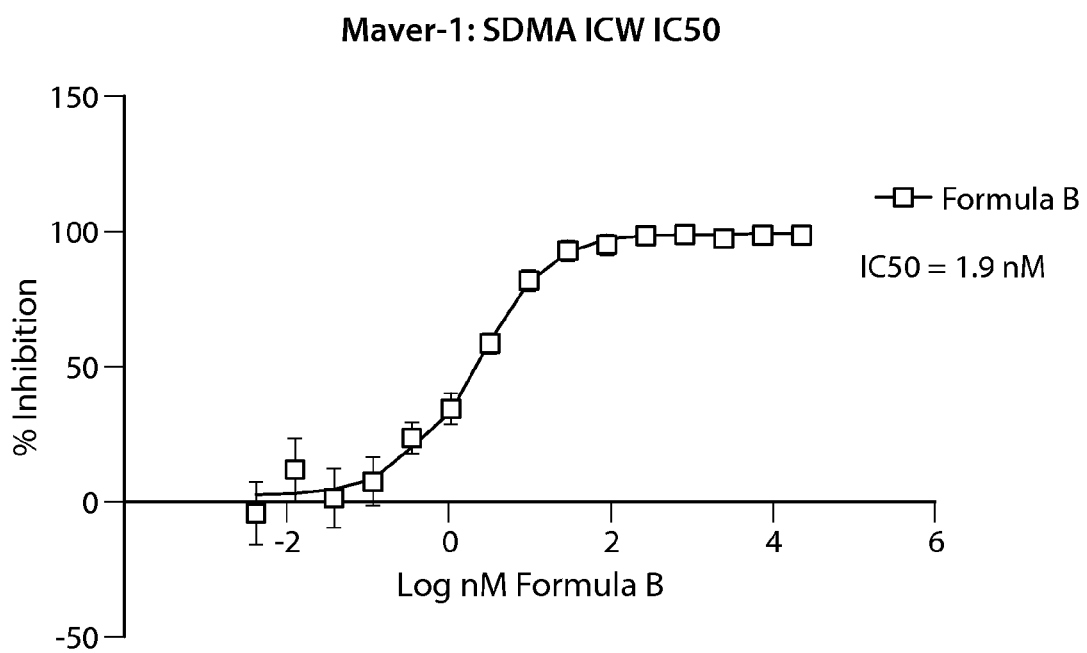
FIG. 3 shows $IC_{50}$ (nM) results from the ICW assay performed in Maver-1 cells treated with Formula B. N=1. Percent inhibition was determined and $IC_{50}$ curves were generated using triplicate wells per concentration of compound. $IC_{50}$ values were calculated using GraphPad Prism using a 4-parametric fit of the normalized dose response curves with the top fixed to 100%.
Figure 4:
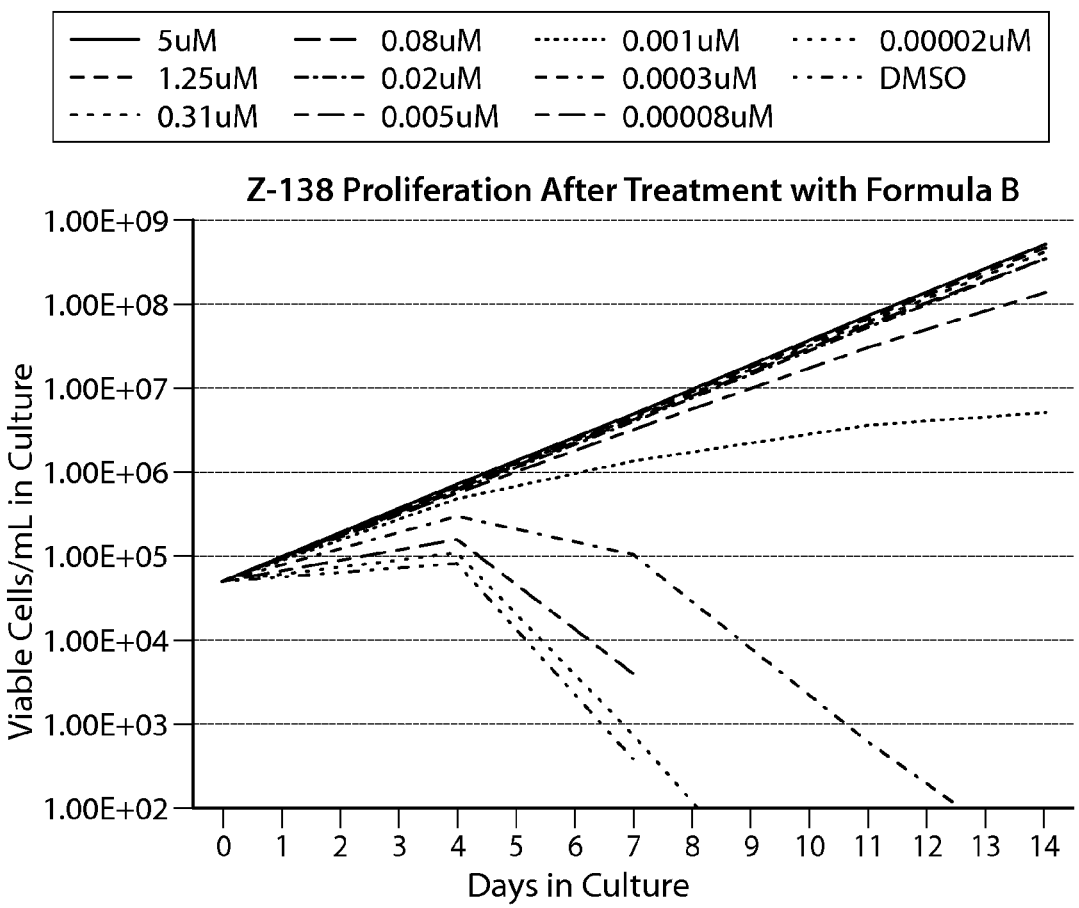
FIG. 4 illustrates a representative sample of a long-term proliferation assay performed in the mantle cell lymphoma cell line Z-138. Assays were performed in technical triplicates, reading cell viability over 14 days. Growth curves (top panel) were calculated in Excel. $IC_{50}$ (bottom panel) and $IC_{90}$ (not shown) values were calculated in GraphPad Prism using a non-linear regression analysis, fixing the top and bottom of the curves to 100 and 0%, respectively. The IC50 values in the Table are indicated in microM.
Figure 4:
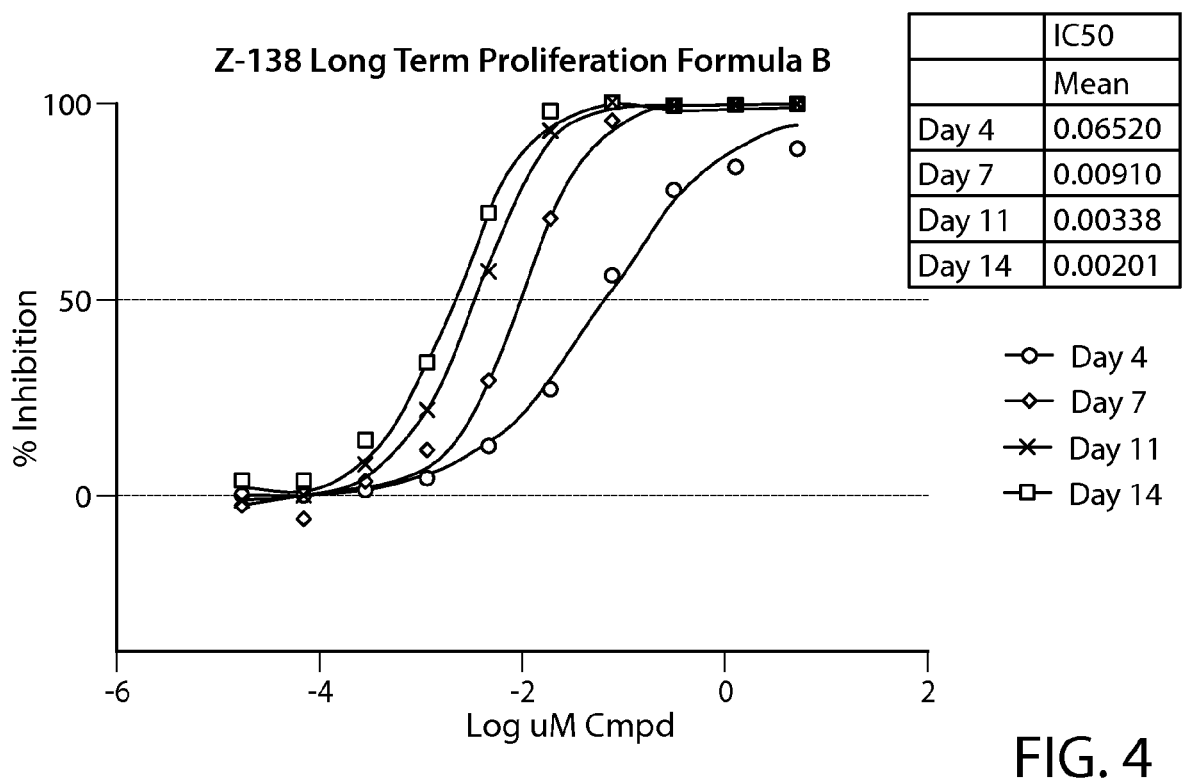
Figure 5:
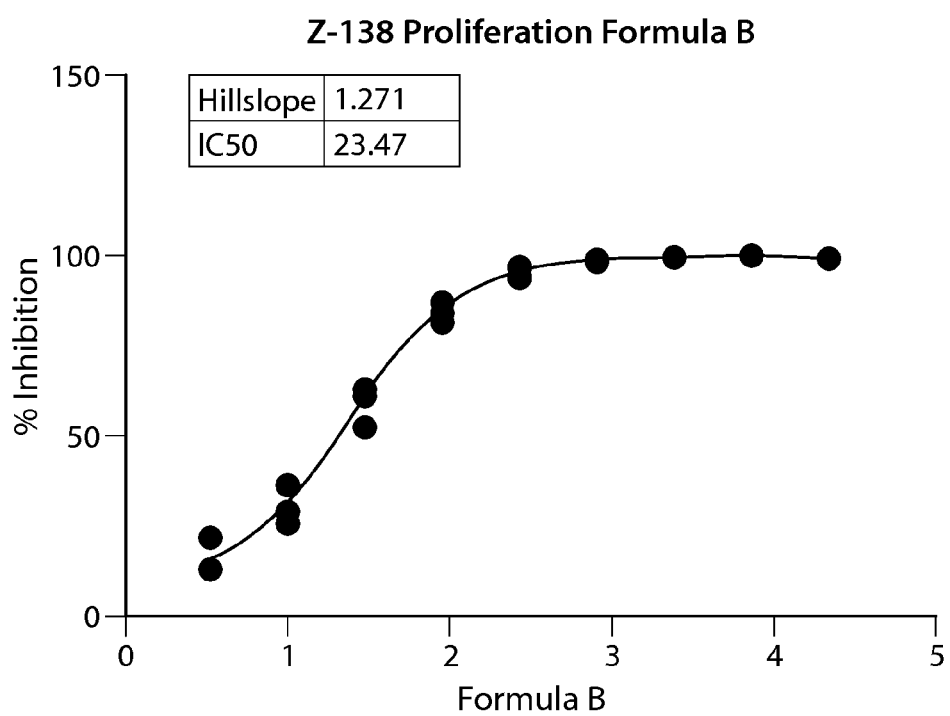
FIG. 5 shows $IC_{50}$ results from the HTP assay performed in Z-138 cells treated with Formula B. N=1. The $IC_{50}$ data are indicated in nM.

Formula B was tested in the ICW assay with Maver-1 cells to determine the IC50 of cellular methylation using the SYM11 antibody. An $IC_{50}$ of 1.9 nM was obtained after 4 days of treatment with compound (FIG. 3, n=1).

Figure 6:
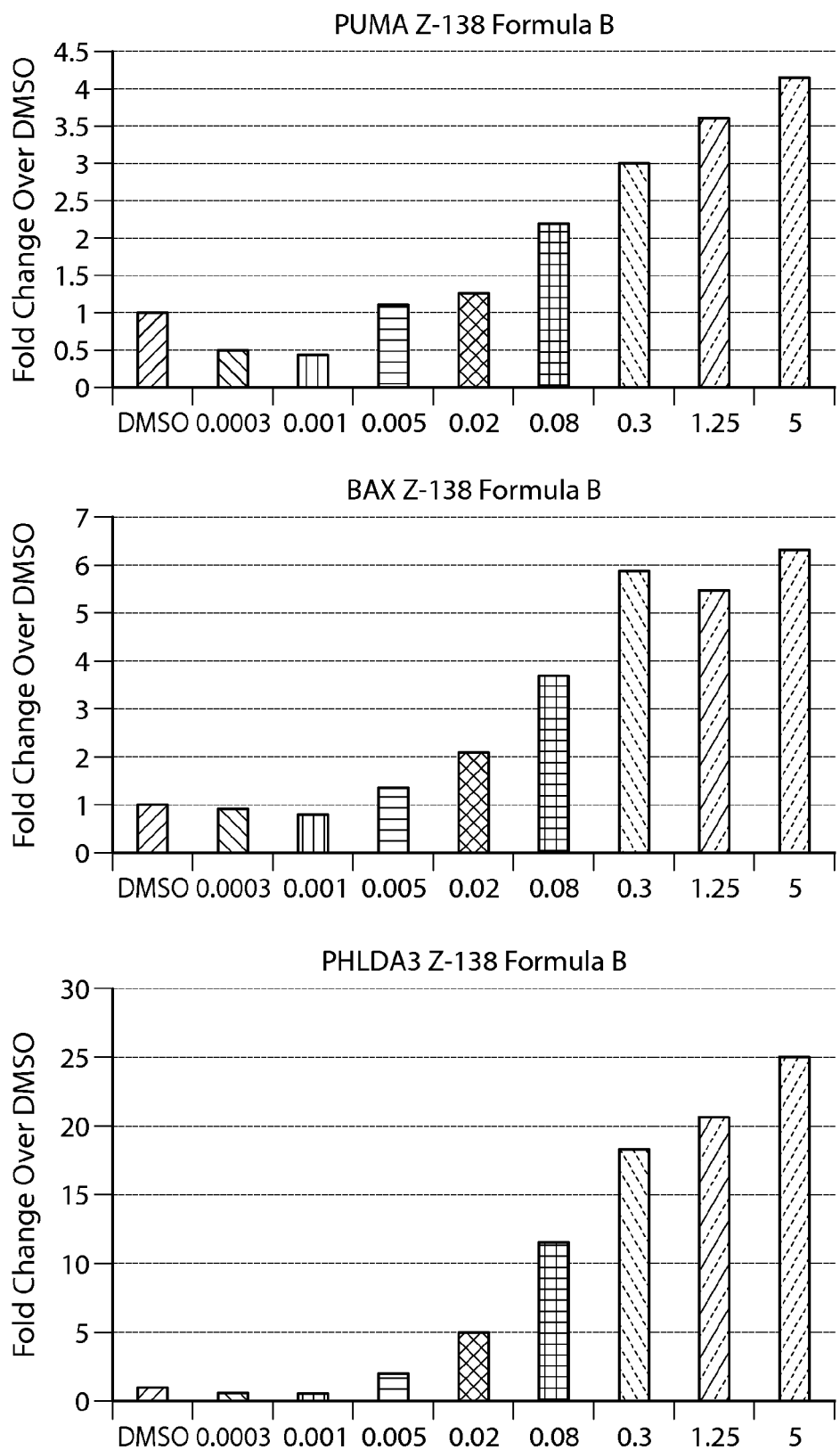
FIG. 6 shows gene expression changes in MCL lines upon treatment with Formula B. Real time PCR for each sample was performed in duplicate. The fold change was calculated using the Comparative Ct method ($-2^{-\Delta\Delta Ct}$). N=1.
Figure 6:
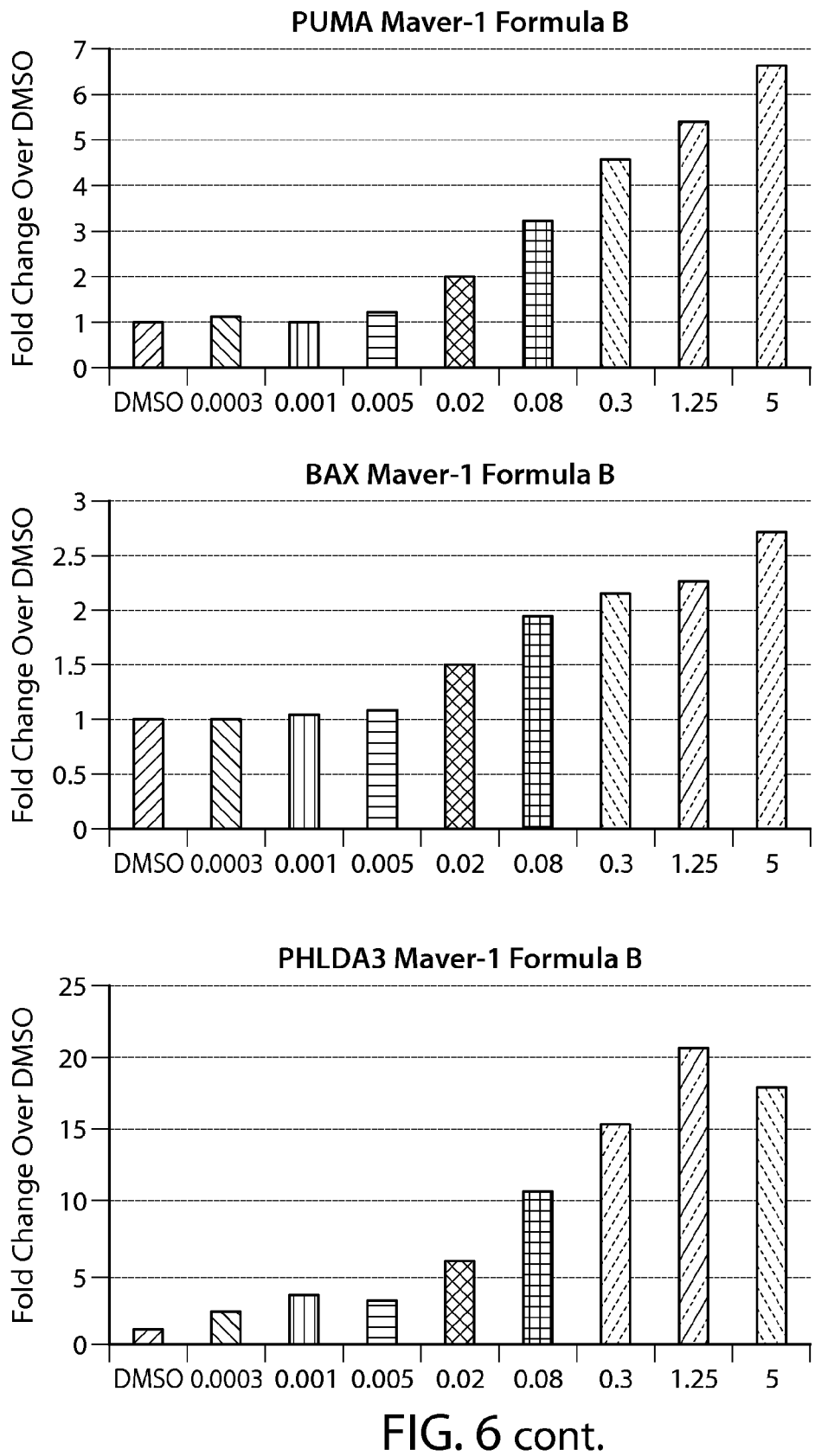
Figure 6:
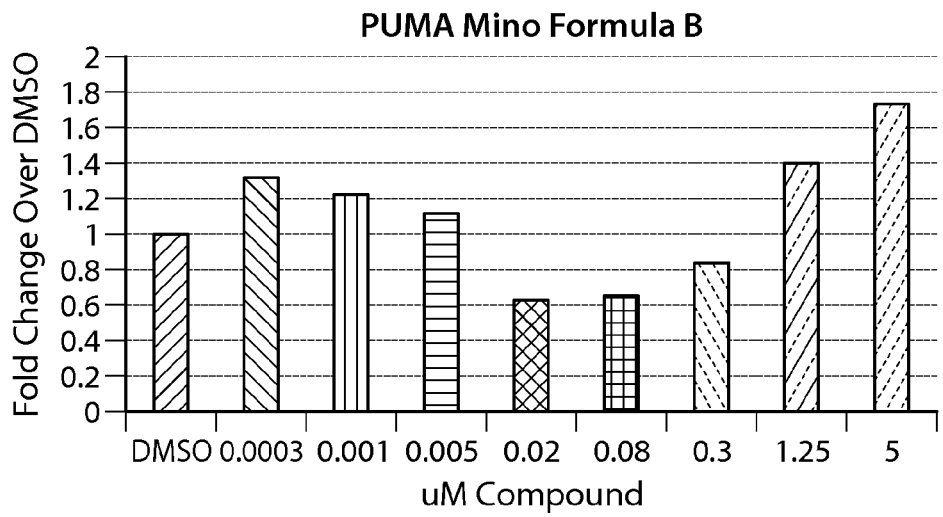
Figure 6:
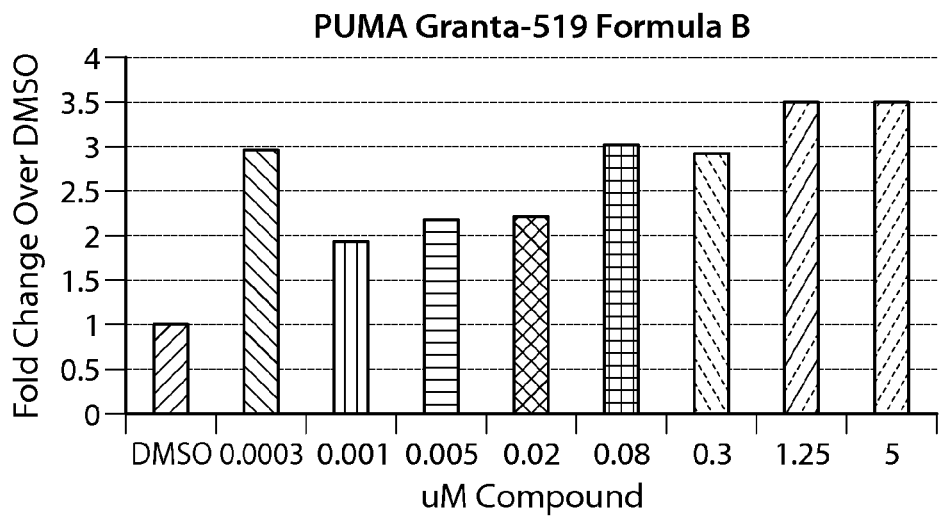
Figure 6:
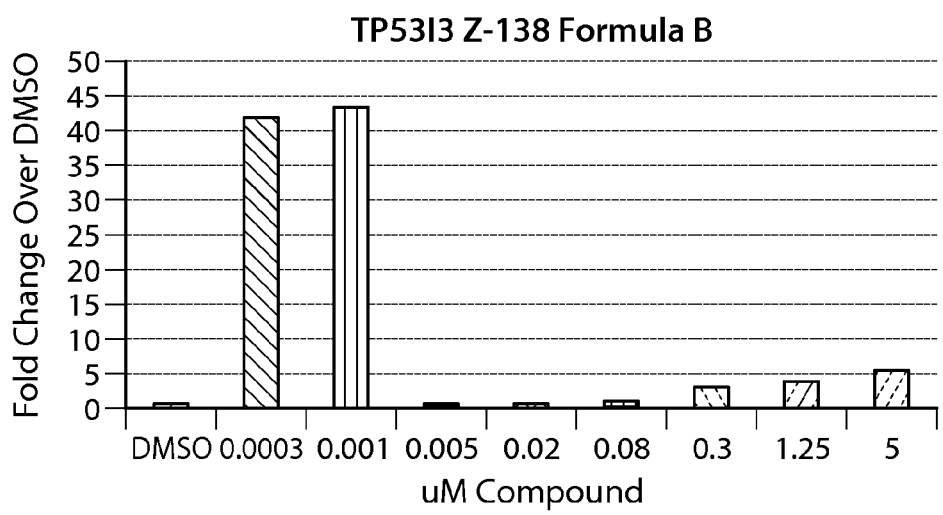
Figure 6:
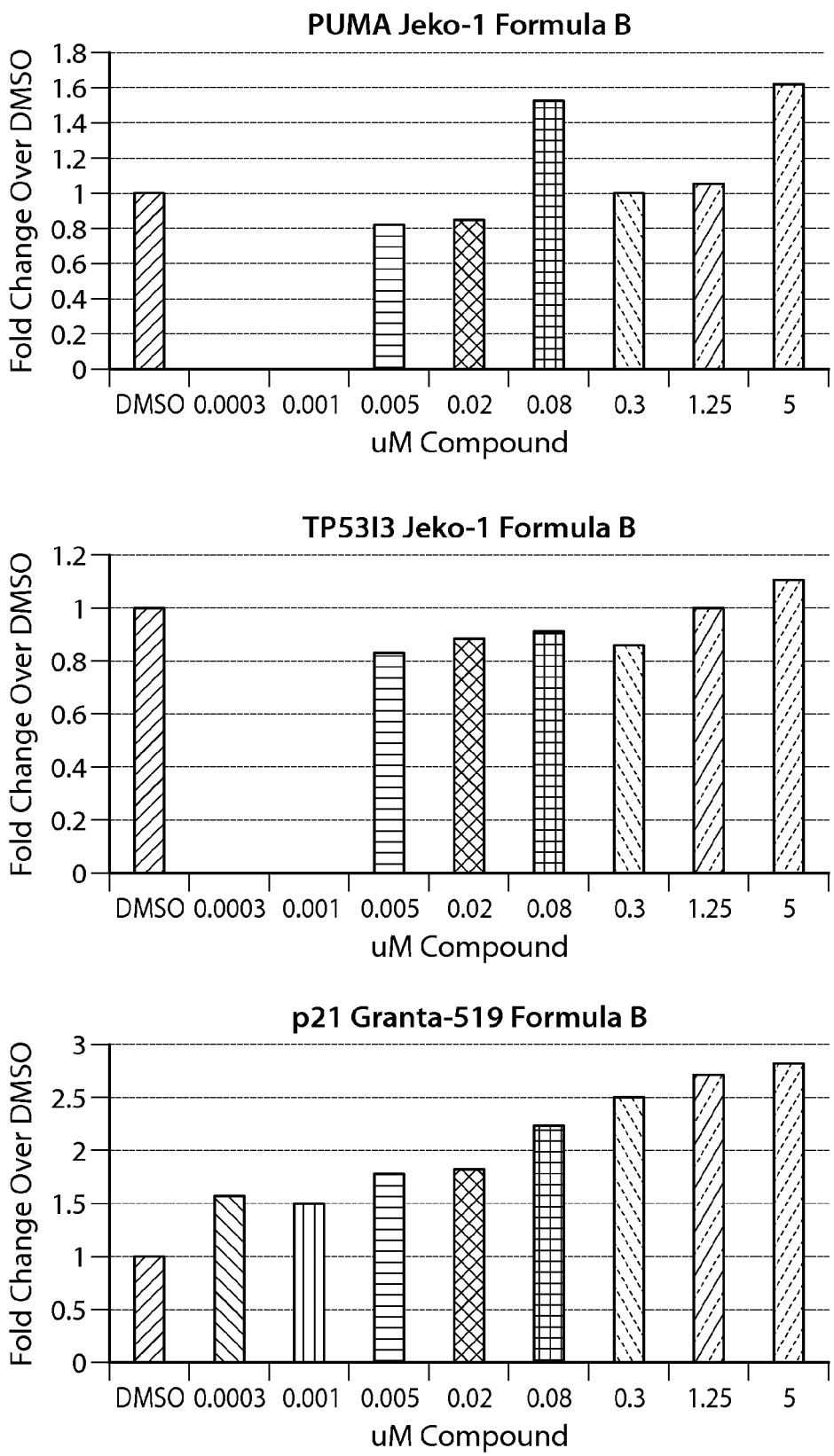
Figure 6:
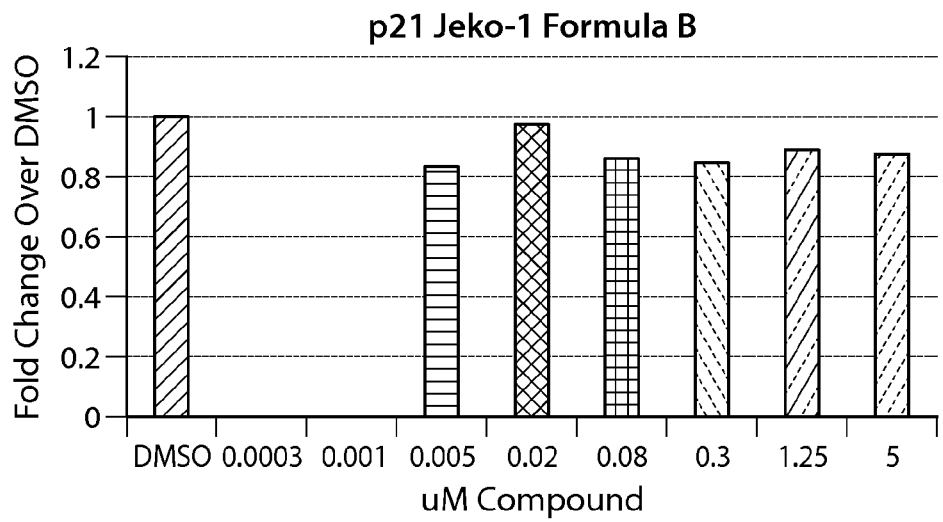
Figure 6:
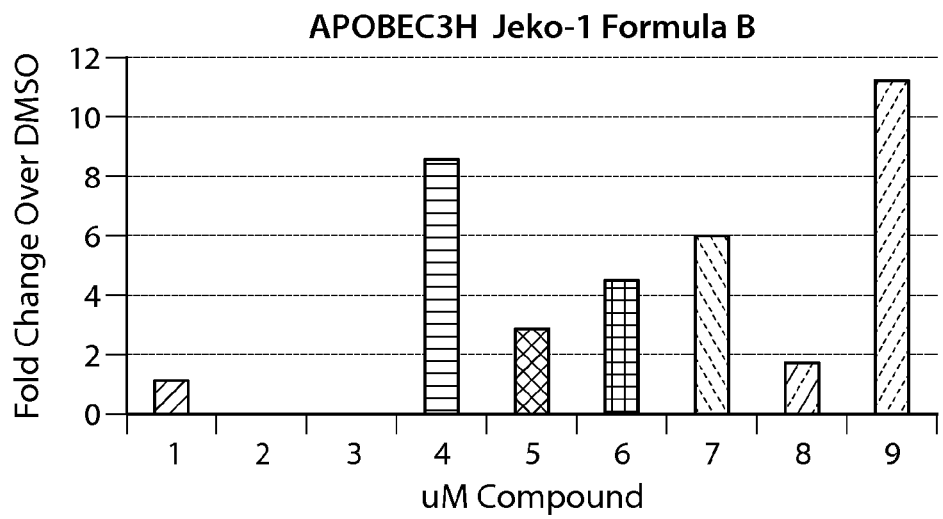
Figure 6:
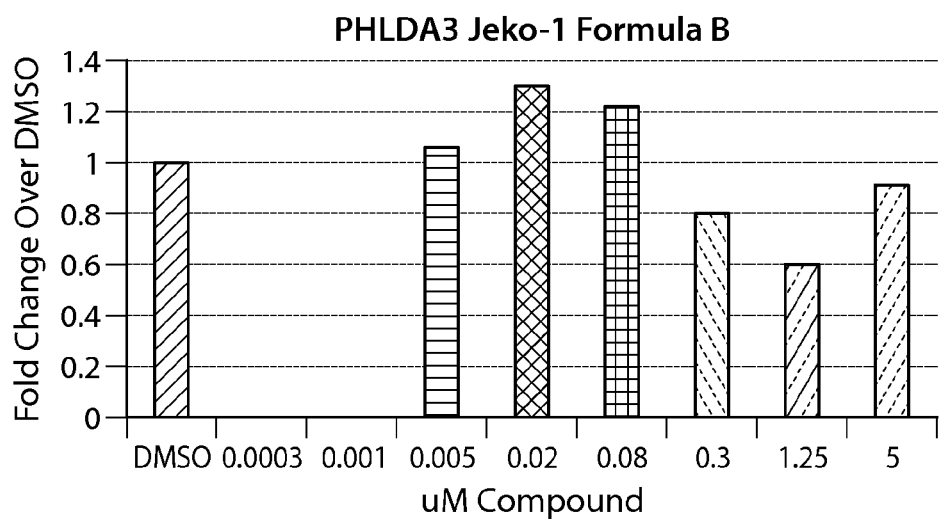
Figure 6:
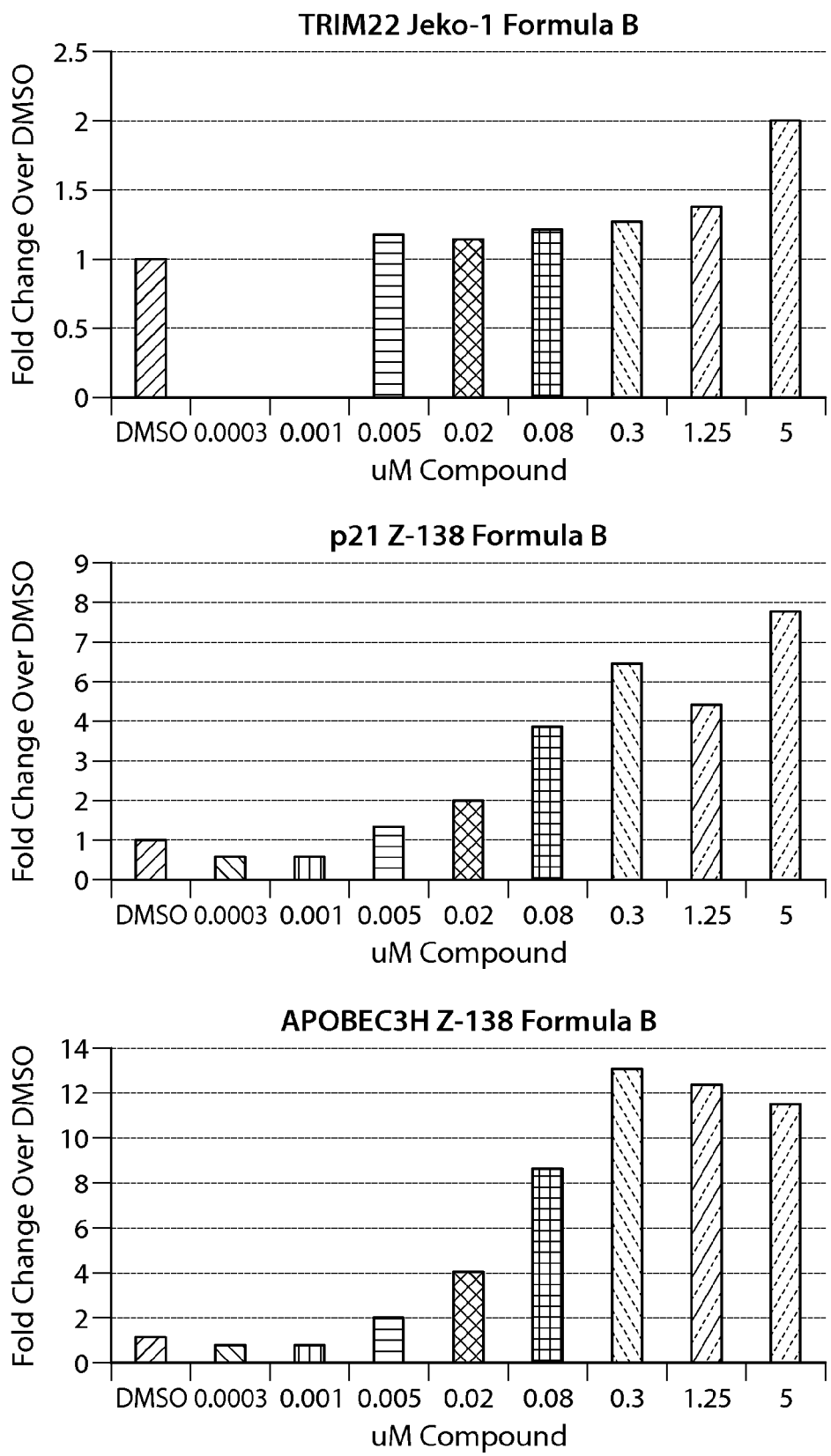
Figure 6:
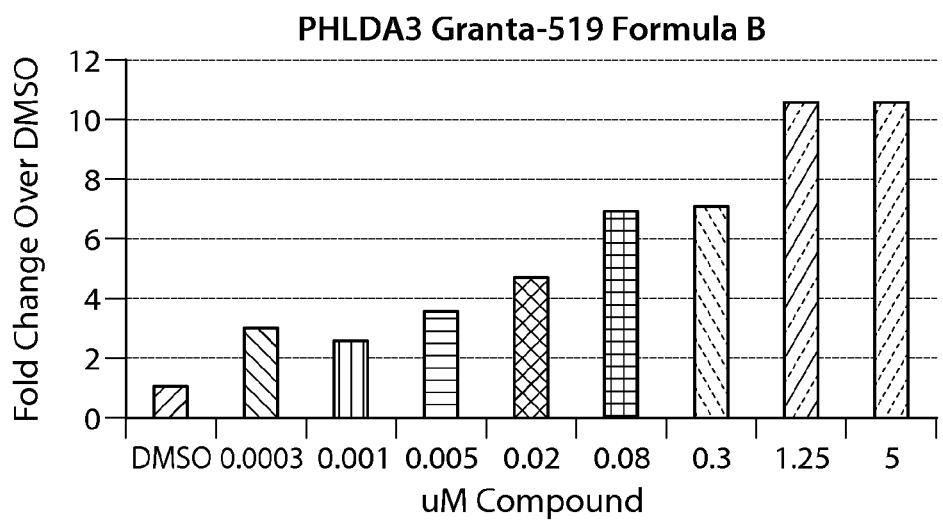
Figure 6:
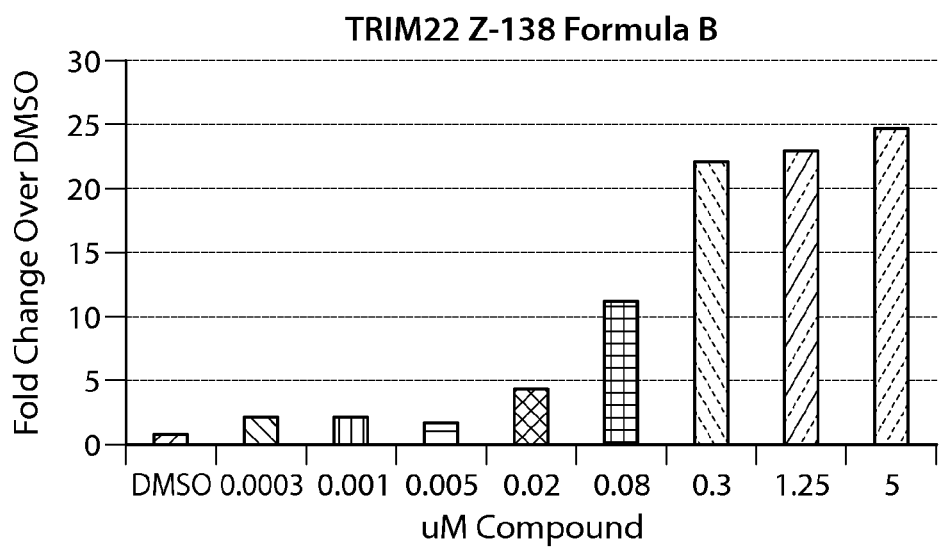
Figure 6:
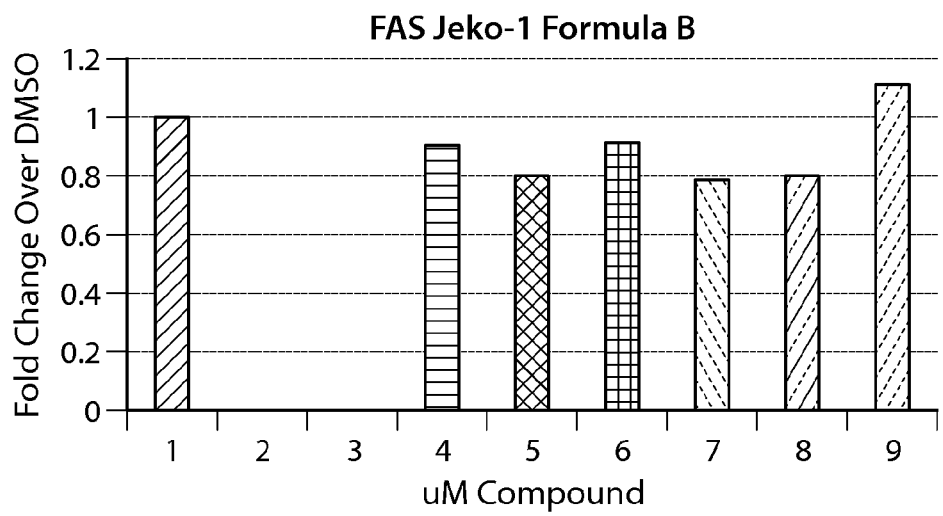
Figure 6:
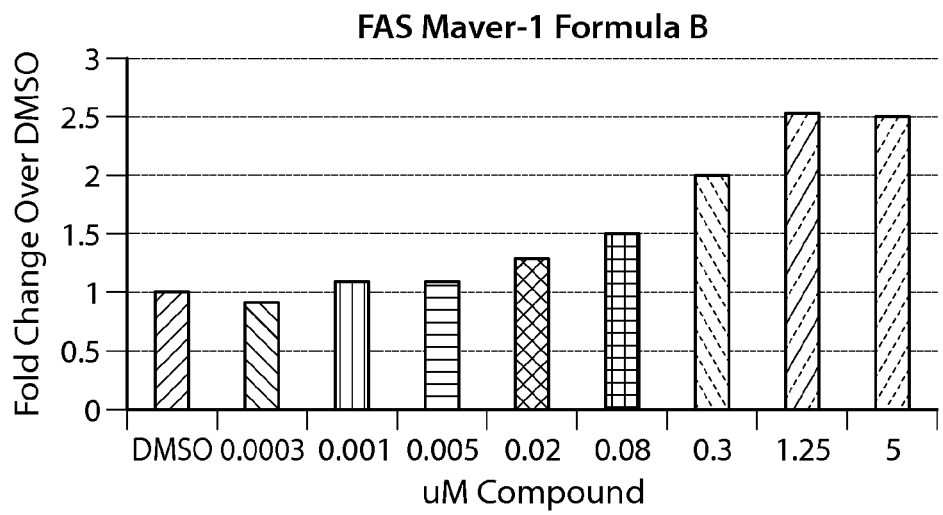
Figure 6:
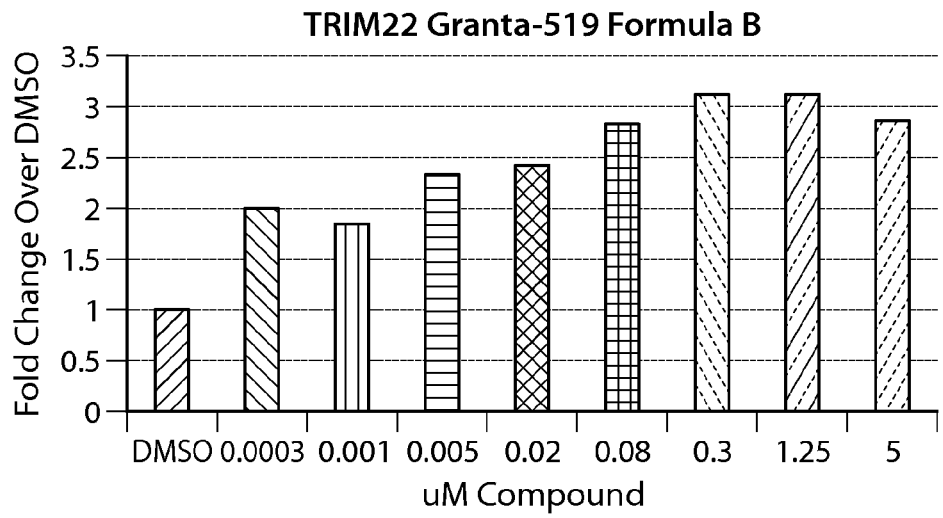
Figure 6:
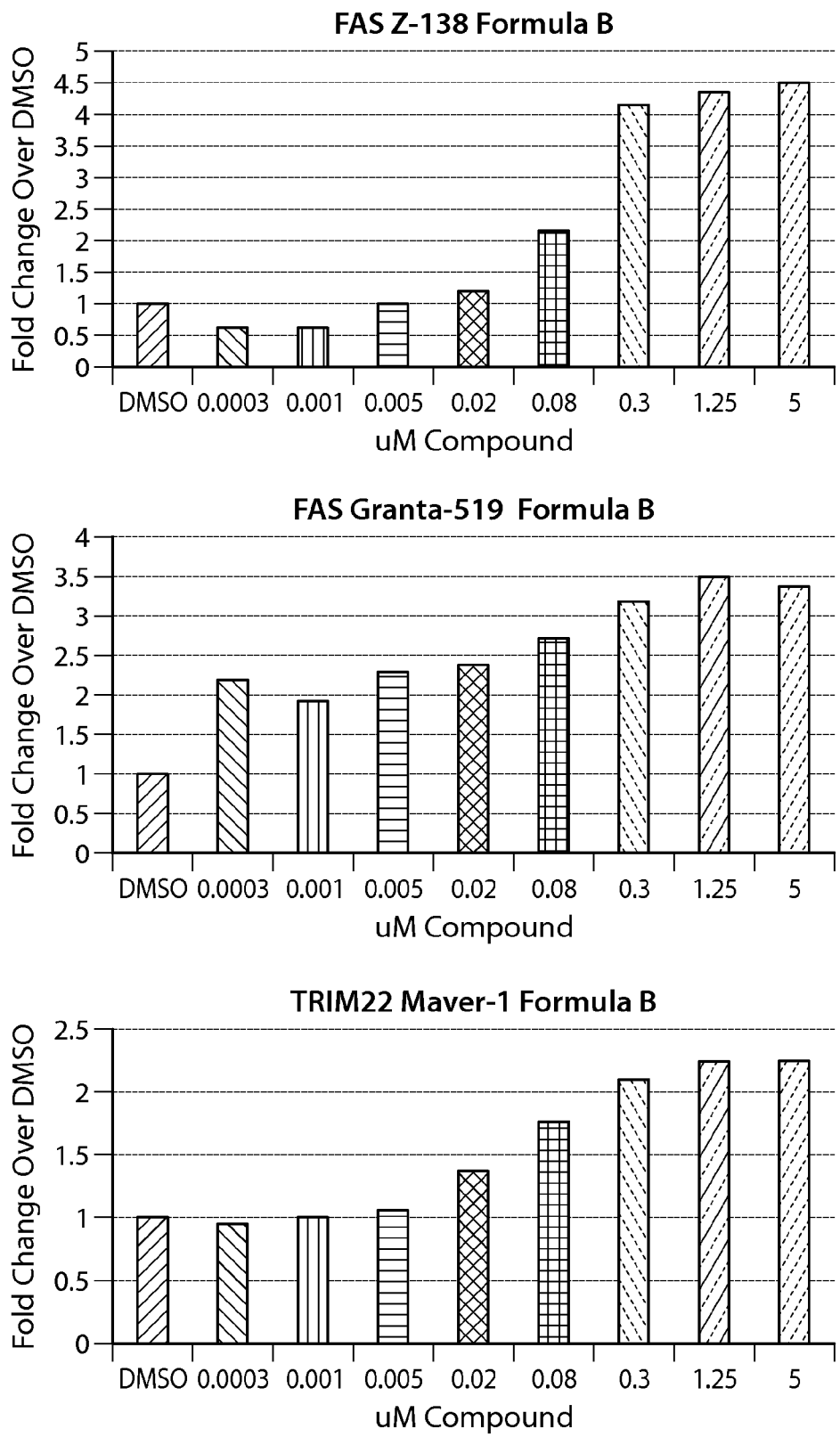

Example 4: Transcriptional Effects of Formula B on a Select Number of Genes Involved in the Apoptotic Response A previous RNA Seq study in MCL cell lines using a tool compound with the same cellular potency as Formula B identified expression changes in a number of genes involved in the apoptotic response (unpublished results). These genes included the Bcl-2 family members PUMA and BAX, well characterized drivers of the apoptotic response. Other genes implicated in the apoptotic response were also identified and include PHLDA3, TP53I3, p21, APOBEC3H, TRIM22, and FAS. Z-138 cells treated with compound showed dose-dependent increases in all genes tested (with the exception of TP53I3) ranging from 4-fold to 25-fold over DMSO. Maver-1 cells also showed gene expression changes in a number of genes tested ranging from 2-fold to 20-fold increases in expression over DMSO. Granta-519 showed up to a 10-fold increase in the gene PHLDA3 however, only modest increases in gene expression for p21, TRIM22, and FAS were observed. Jeko-1 and Mino cells treated with compound did not show any significant effects in any of the genes tested (Table 4 and FIG. 6).

TABLE 4

Gene Expression Results from MCL Cell Lines Treated with Formula B on Day 4.

| Gene | Cell Lines Tested | Cell Lines Showing Dose Dependent Changes |
|---|---|---|
| PUMA | Z-138, Maver-1, Mino, Jeko-1, Granta-519 | Z-138, Maver-1 |
| BAX | Z-138, Maver-1 | Z-138, Maver-1 |
| PHLDA3 | Z-138, Maver-1, Granta-519, Jeko-1 | Z-138, Maver-1, Granta-519 |
| TP53I3 | Z-138, Jeko-1 | No lines identified with effects |
| P21 | Z-138, Granta-519, Jeko-1 | Z-138, Granta-519 |
| APOBEC3H | Z-138, Jeko-1 | Z-138 |
| TRIM22 | Z-138, Maver-1, Granta-519, Jeko-1 | Z-138, Maver-1, Granta-519 (slight) |
| FAS | Z-138, Maver-1, Granta-519, Jeko-1 | Z-138, Maver-1, Granta-519 (slight) |

Example 5: Effect of Formula B on Z-138 and Maver-1 Apoptosis

Figure 7:
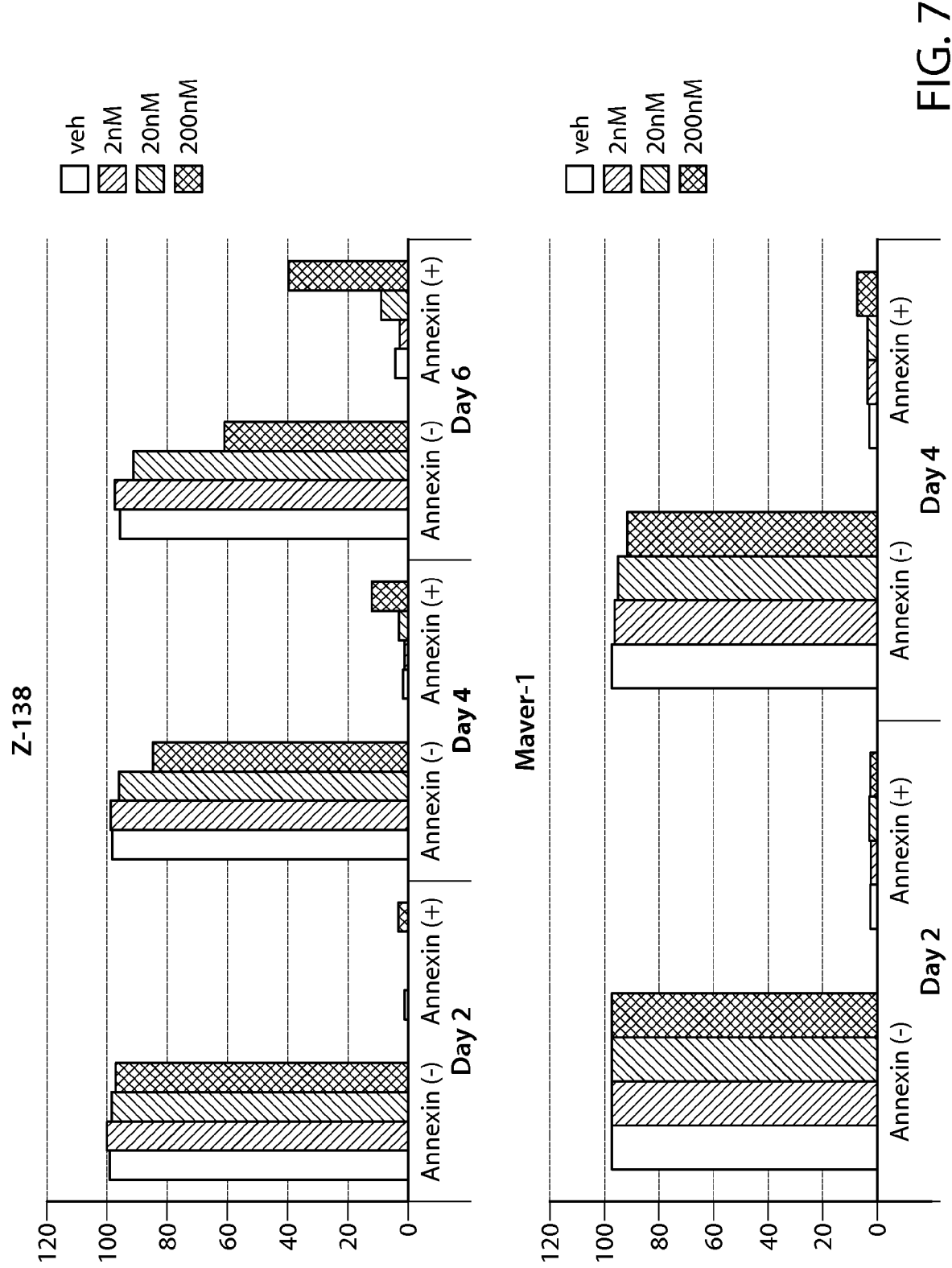
FIG. 7 shows Annexin-V staining of Z-138 and Maver-1 cells treated with Formula B. N=1.

The mechanism of cell killing was evaluated in the MCL cell lines, Z-138 and Mayer-1. Cells were treated at various time points with 2 nM, 20 nM, and 200 nM of Formula B. Apoptosis was assessed by measuring the percentage of Annexin-V positive cells and the assay was performed in triplicate. A 12% and 40% increase in Annexin-V positive cells was observed with treatment of 200 nM Formula A after 4 and 6 days respectively (FIG. 7) in Z-138 cells. A more modest increase was observed in Maver-1 cells. 8% of cells stained positive for Annexin-V after 4 days of treatment with Formula A. A corresponding decrease in Annexin negative cells was observed at those time points in both cell lines.

Figure 8:
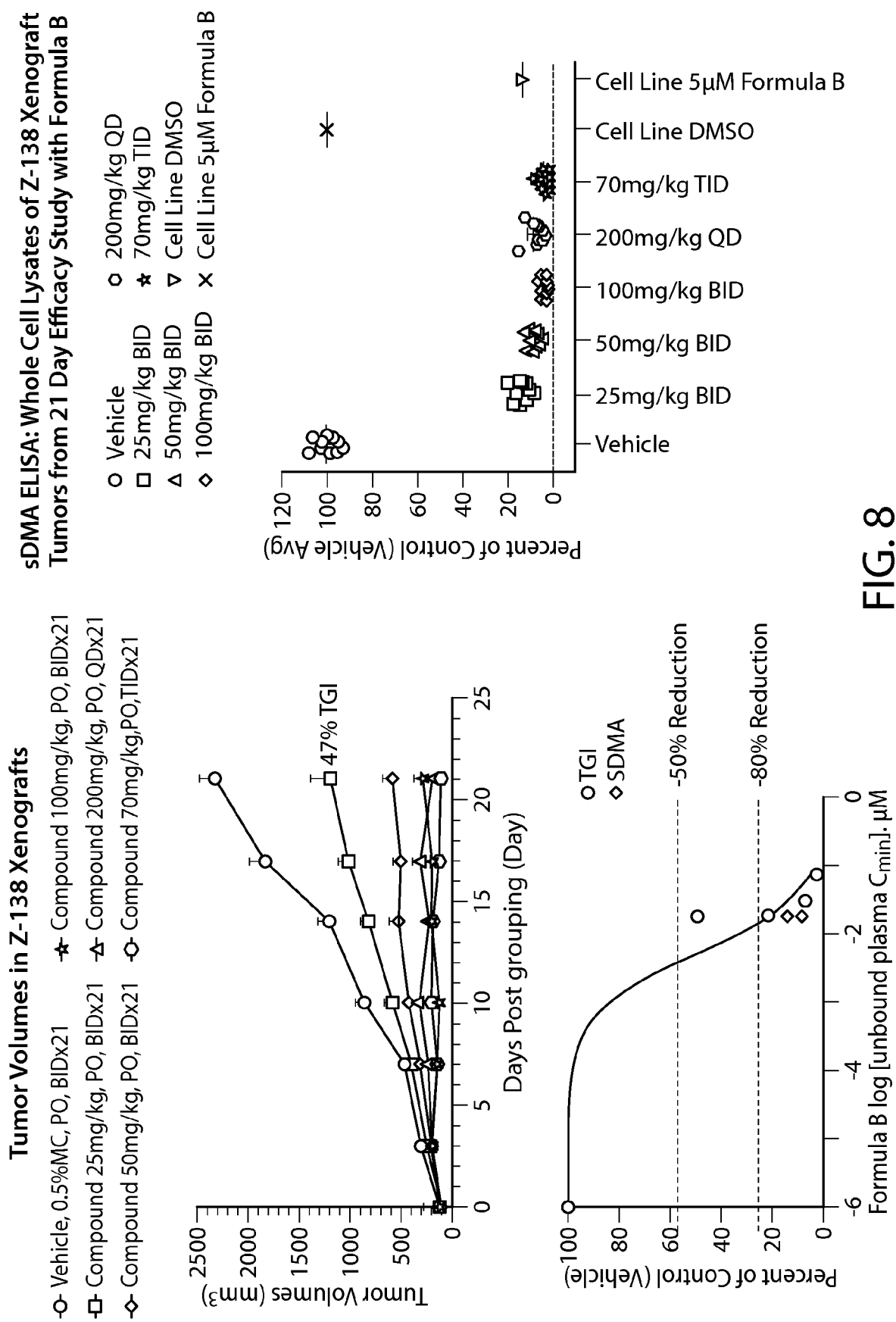
FIG. 8 shows Formula B efficacy in a Z-138 xenograft model—all doses tested show >50% TGI.
Figure 9:
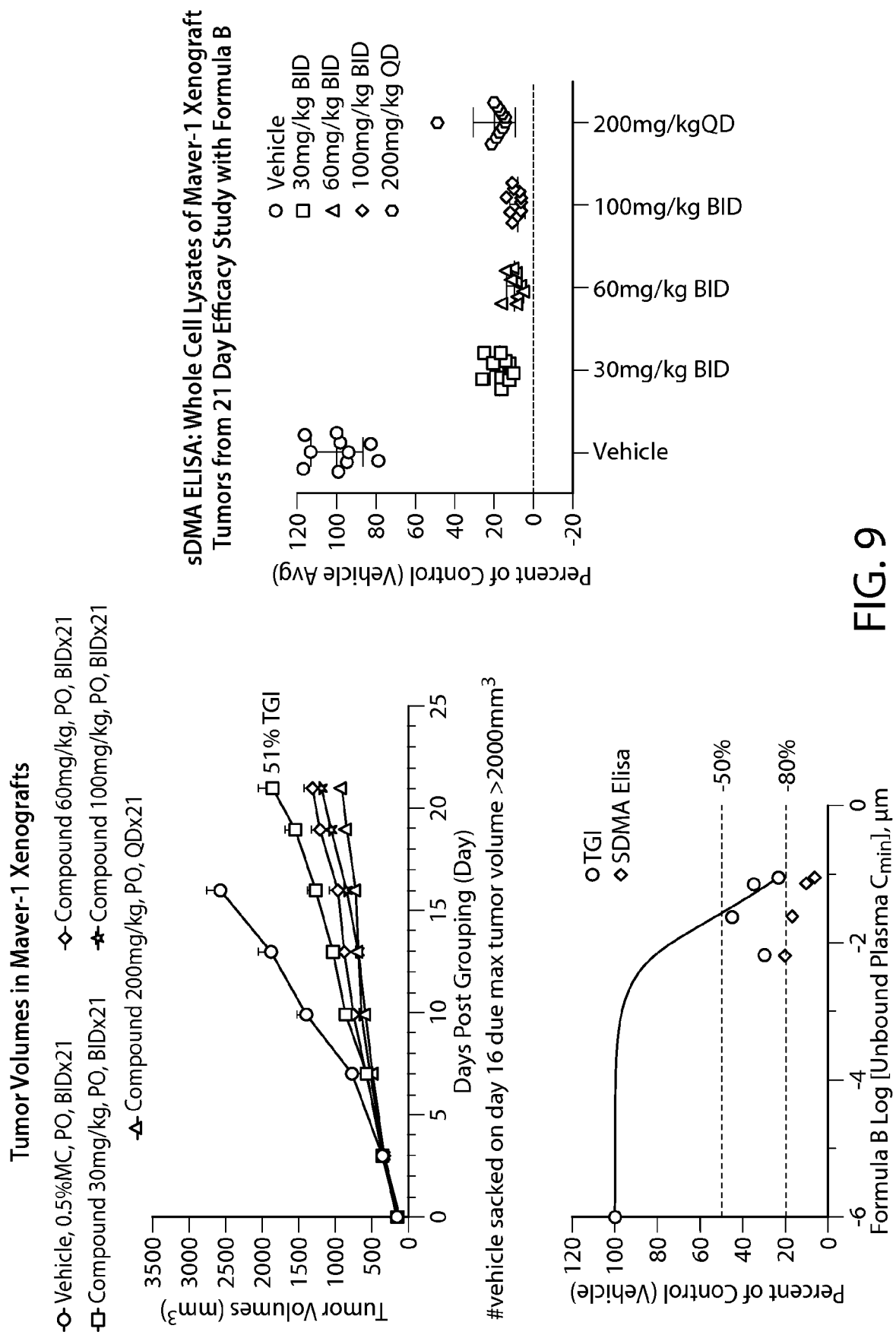
FIG. 9 shows Formula B efficacy in a Maver-1 xenograft model—all doses tested show >50% TGI.
Figure 10:
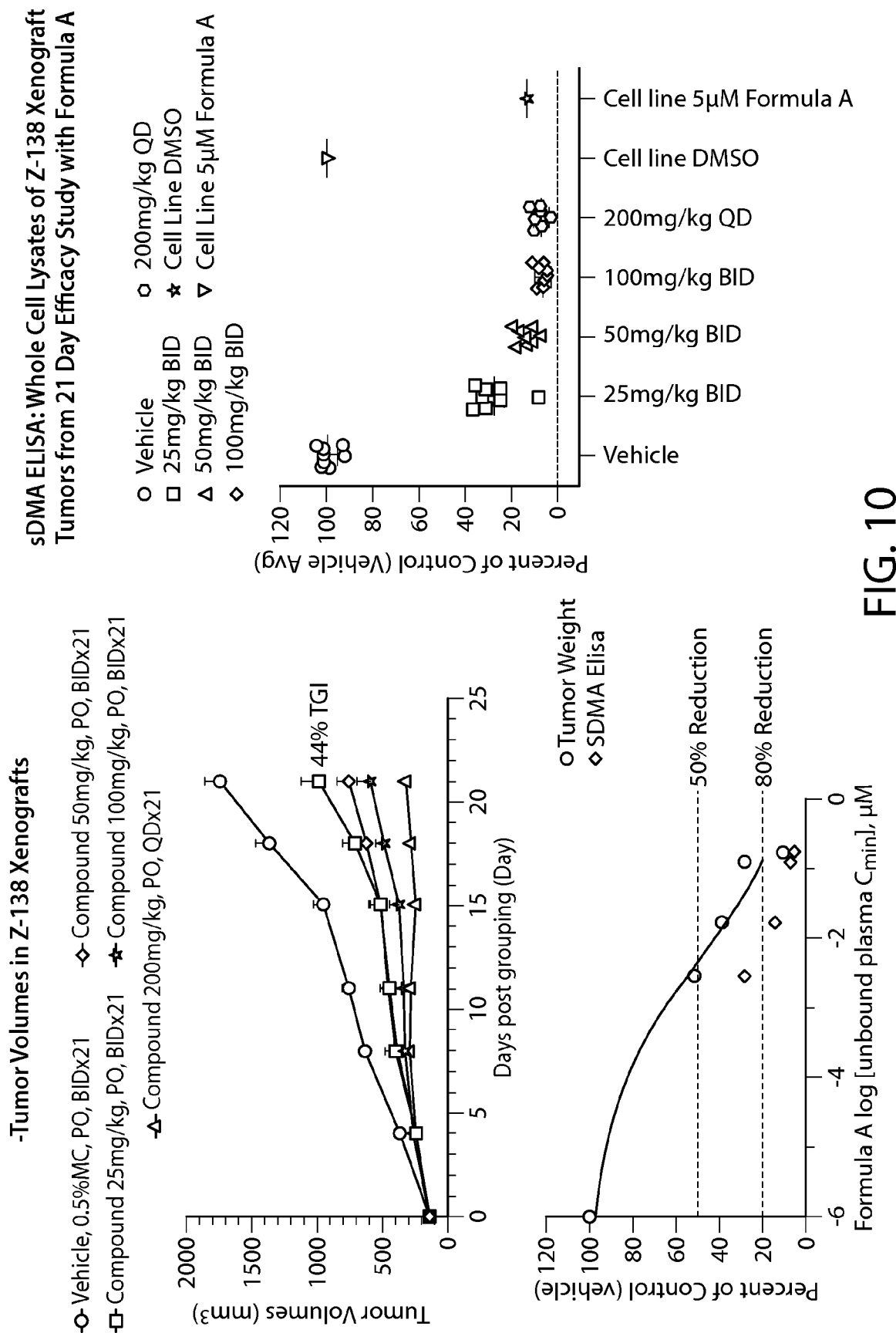
FIG. 10 shows Formula A efficacy in a Z-138 xenograft model—all doses tested show >50% TGI.
Figure 11:
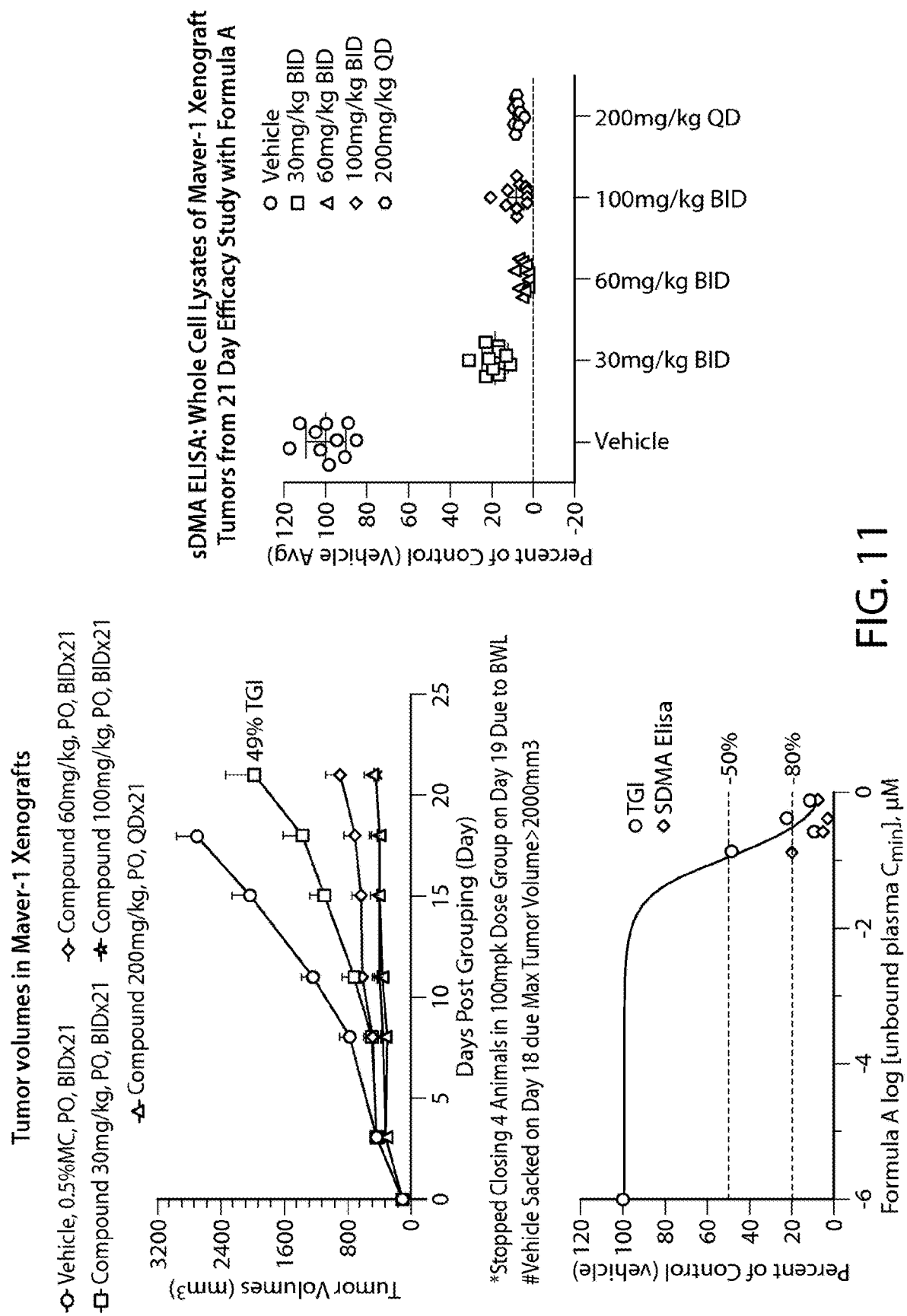
FIG. 11 shows Formula A efficacy in a Maver-1 xenograft model—all doses tested show >50% TGI.

Example 6: PK/PD/Tumor Growth Inhibition (TGI) Analysis of 21 Day Mantle Cell Lymphoma Xenograft Studies Data presented in this example were determined after analysis of 21 day samples of mantle cell lymphoma tumors. $C_{min}$ PK samples were taken prior to the last dose on day 21. Tumors were excised, weighed and processed for methyl mark. Methyl mark reduction was measured in tumor samples and is shown as percent of vehicle control (POC). Both SYM11 and sDMA Elisa were used to measure methyl mark and the data shown is averaged from 10 animals. Tumor growth inhibition was determined using tumor volume reduction at day 21 expressed as a percent of POC. In vivo inhibition curves were also generated and $IC_{50}$ values determined. Plasma levels from each group are averaged from 5 animals. The efficacy of Formula B in Z-138 cells is shown in FIG. 8. All doses tested resulted in ≥50% TGI and tumors that had >50% TGI displayed a methyl mark reduction >80%. The average body weight loss (BWL) in all groups was <6%. The efficacy of Formula B in Maver-1 cells is shown in FIG. 9. All doses tested show >50% TGI. All tumors had that had >50% TGI displayed a methyl mark reduction >80%. The average BWL in all groups was <4%. The efficacy of Formula A in Z-138 cells is shown in FIG. 10. The average BWL in all groups was <8%, except in the 100 mg/kg does group were 4 animals exceeded BWL of 15%. Tumors from animals treated with Formula A which had >50% TGI displayed a methyl mark reduction >80%. The efficacy of Formula A in Maver-1 cells is shown in FIG. 11. All groups tested displayed significant methyl mark reduction (>80%) and TGI>50%.

Figure 12:
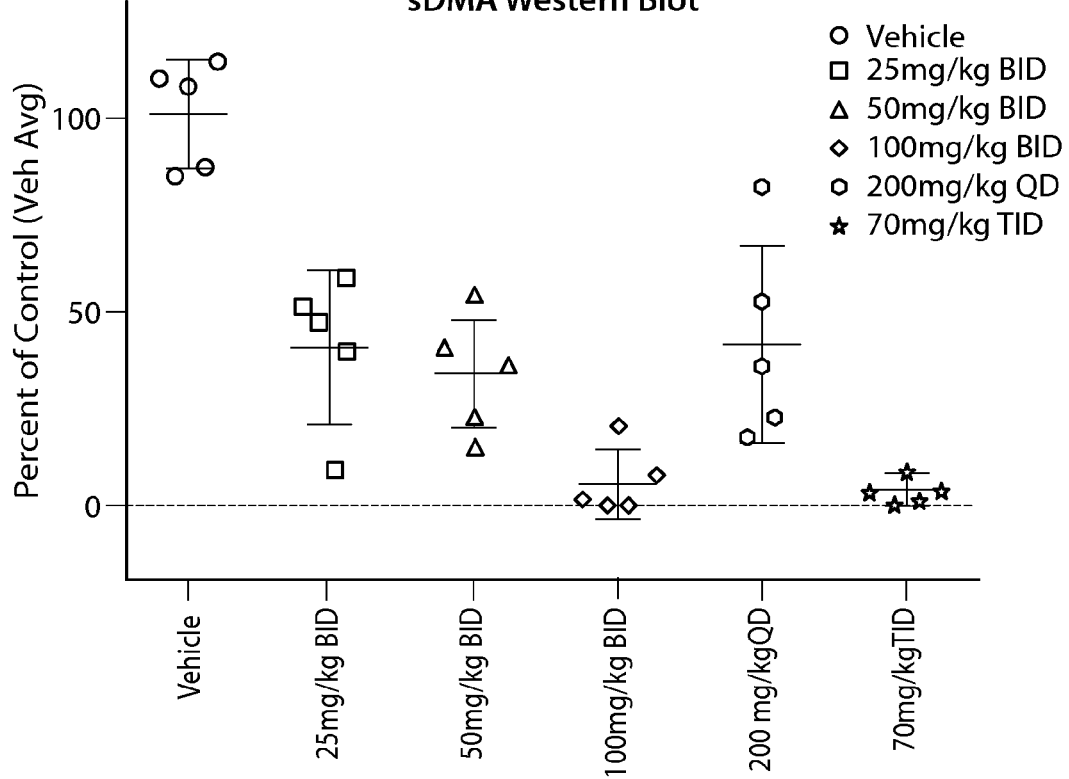
FIG. 12 shows in vivo Methyl Mark inhibition in surrogate tissue. sDMA Western blot analysis of bone marrow samples from a Z-138 cell efficacy study with Formula B.
Figure 12:
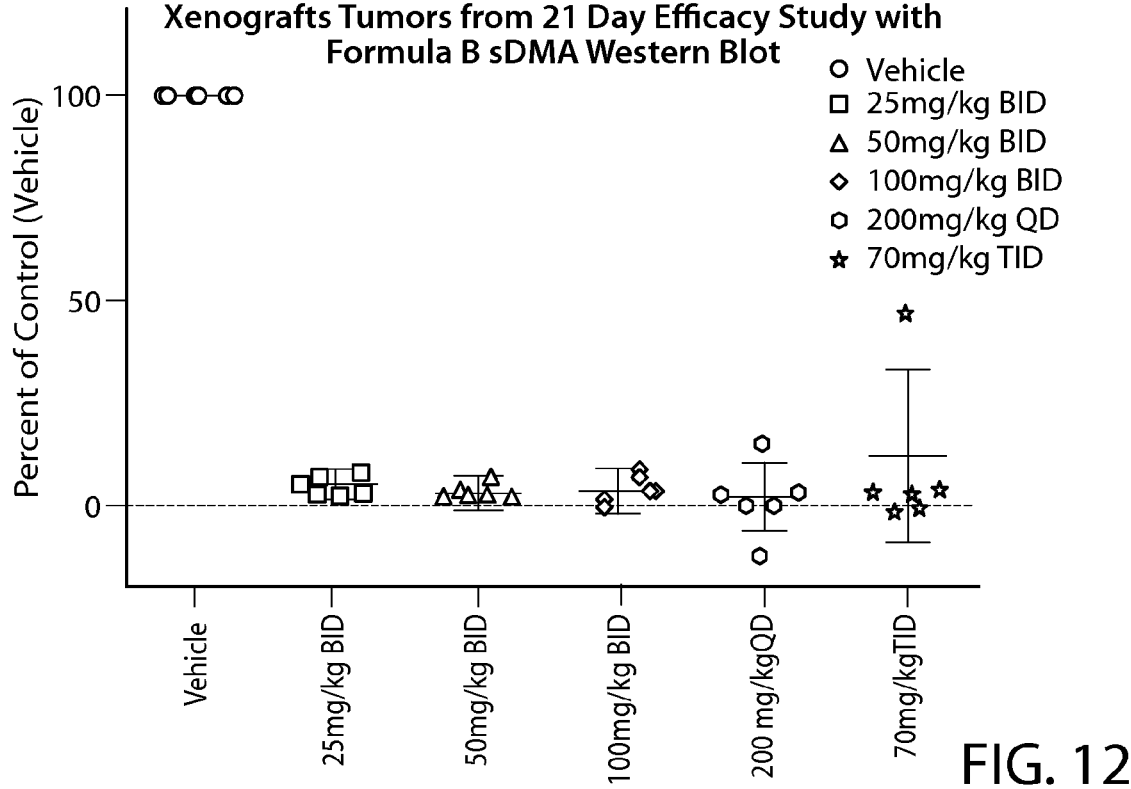

Data presented in this study (FIG. 12) also represents the first evidence of in vivo methyl mark inhibition in surrogate tissue. FIG. 12 shows sDMA Western blot results of bone marrow samples from the Z-138 efficacy study with Formula B. Bone marrow samples were harvested on day 21 at the end of the study and lysates were prepared using the same methods as were used for tumors. More of a dose-dependent response in the levels of sDMA methylation was observed in the bone marrow compared to the tumors where the methyl mark was completely removed at all dose groups tested.

Example 7: Breast Cancer Data

Figure 13:
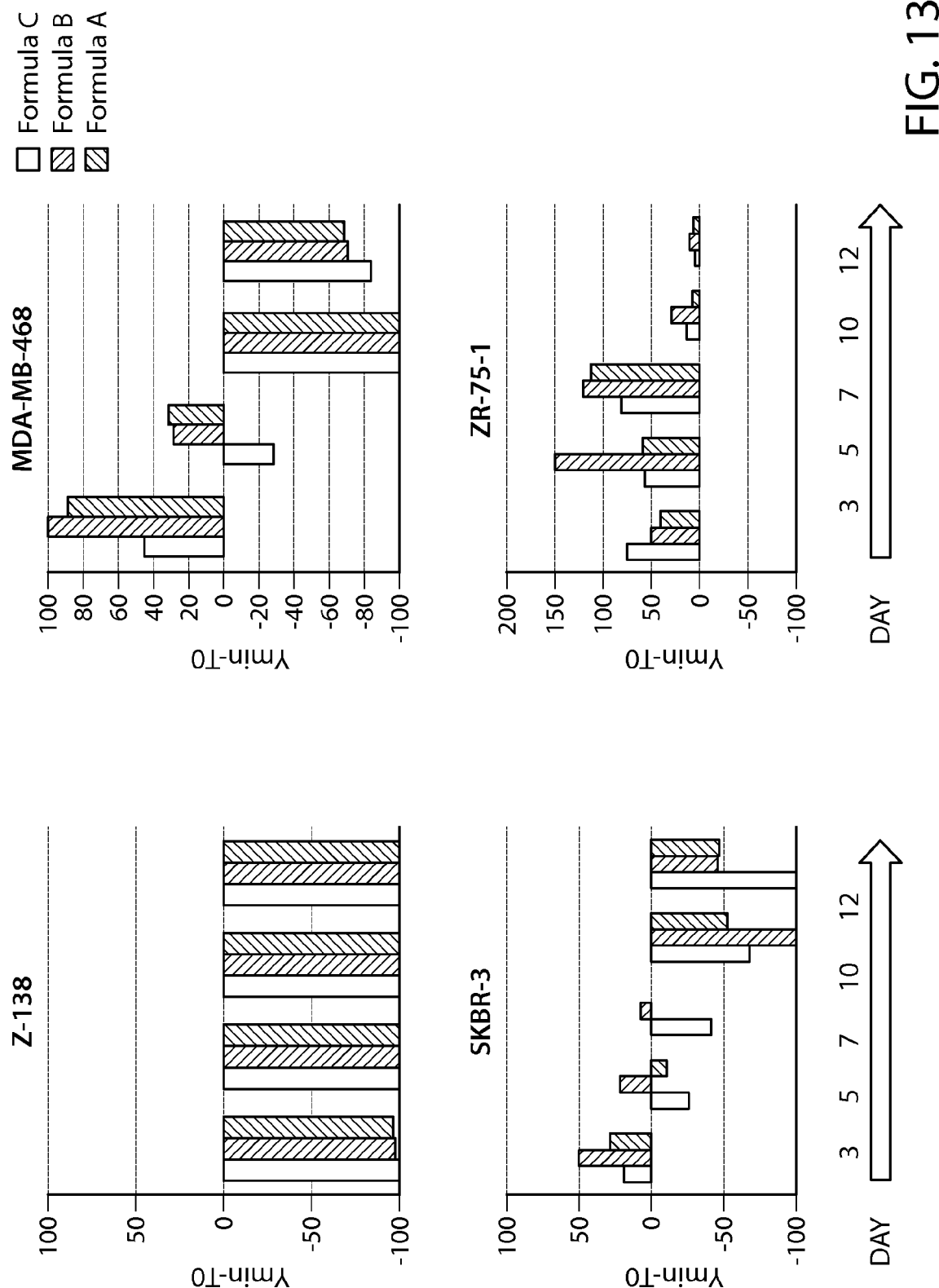
FIG. 13 provides data from a total cell death assay performed on breast cancer cell lines (SKBR-3, ZR-75-1 and MDA-MB-468). MCL cell line (Z-138) was used as a positive control.

In this example, net cell death assays were used to demonstrate the efficacy of PRMT5 inhibitors on breast cancer cell lines. PMRT5 inhibitors Formula A, Formula B and Formula C were used to treat 3 different breast cancer cell lines (SKBR-3, ZR-75-1 and MDA-MB-468). SKBR-3, is a HER2-positive breast cancer cell line. ZR-75-1 is an estrogen receptor/progesterone receptor (ER/PR) positive breast cancer cell line. MDA-MB-468 is a triple-negative (ER−/PG−/HER2−) breast cancer cell line. A mantel cell lymphoma cell line (Z-138) was used as a positive control. The results of the assays are shown in FIG. 13.

Figure 14:
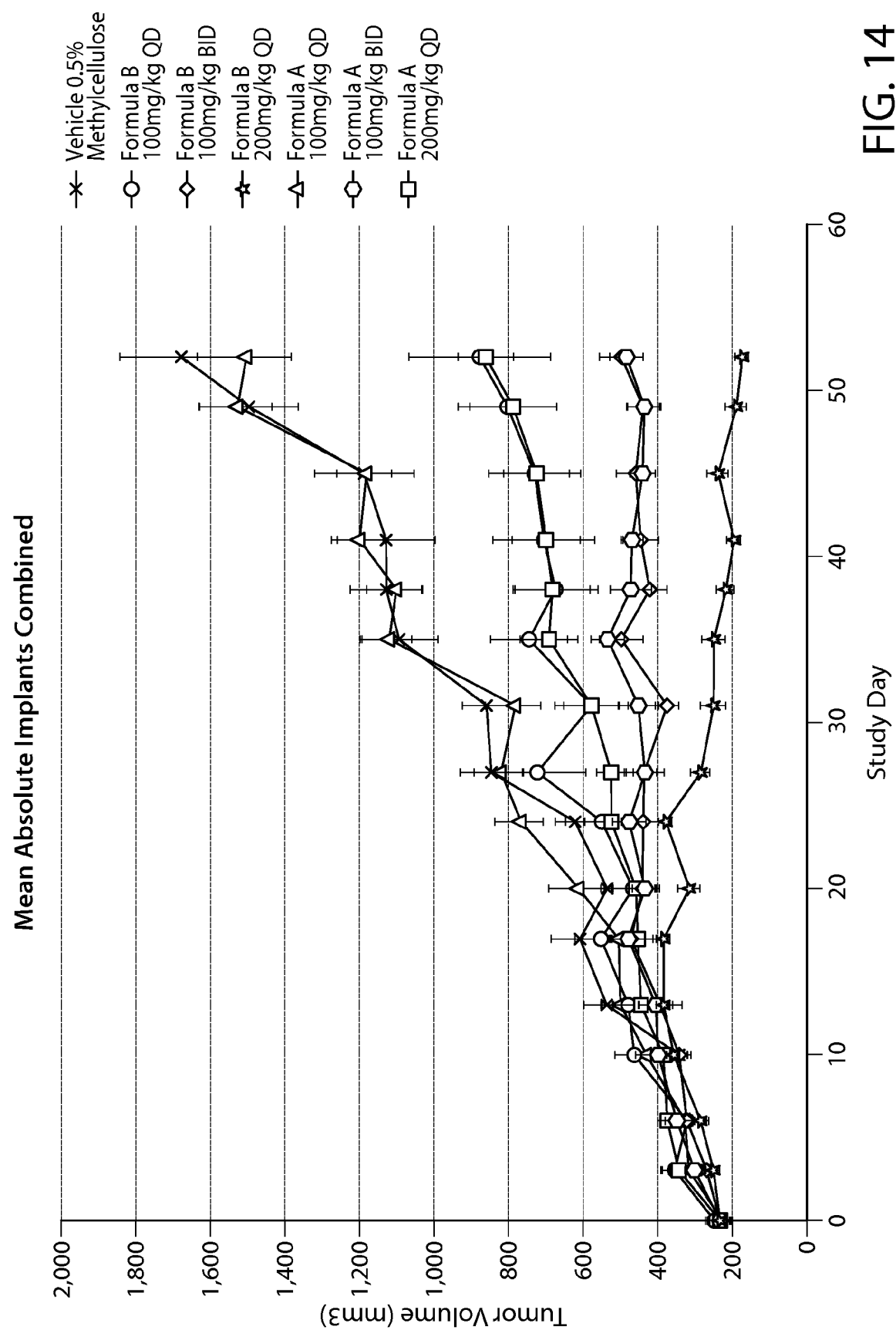
FIG. 14 shows tumor growth inhibition a subQ xenograft model of MDA-MB-468 breast cancer cells treated with PRMT5 inhibitors of Formulae A and B.

Tumor growth inhibition (TGI) was also determined for several dosing regimens for two of the compounds, Formula A and Formula B in a MDA-MB-468 xenograft model. The results of the TGI assays are shown in FIG. 14.

Figure 15:
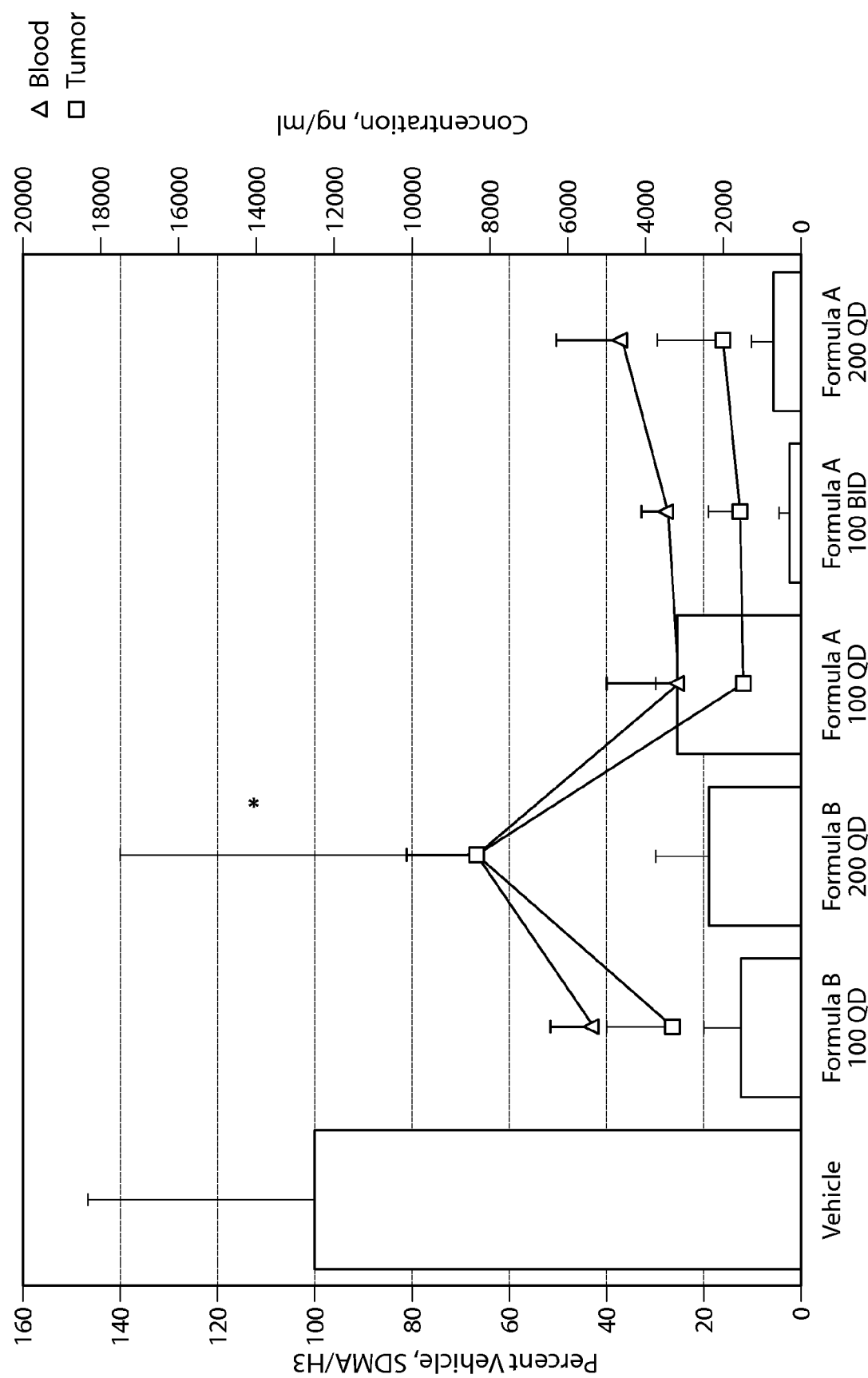
FIG. 15 shows the methyl mark response of a subQ xenograft model of MDA-MB-468 breast cancer cells treated with PRMT5 inhibitors.

The pharmacodynamics methyl mark suppression responses of Formula A and Formula B were also measured in a MDA-MB-468 cell xeonograft model. The responses are shown in FIG. 15.

Example 8: Pancreatic Cancer Data

Figure 16:
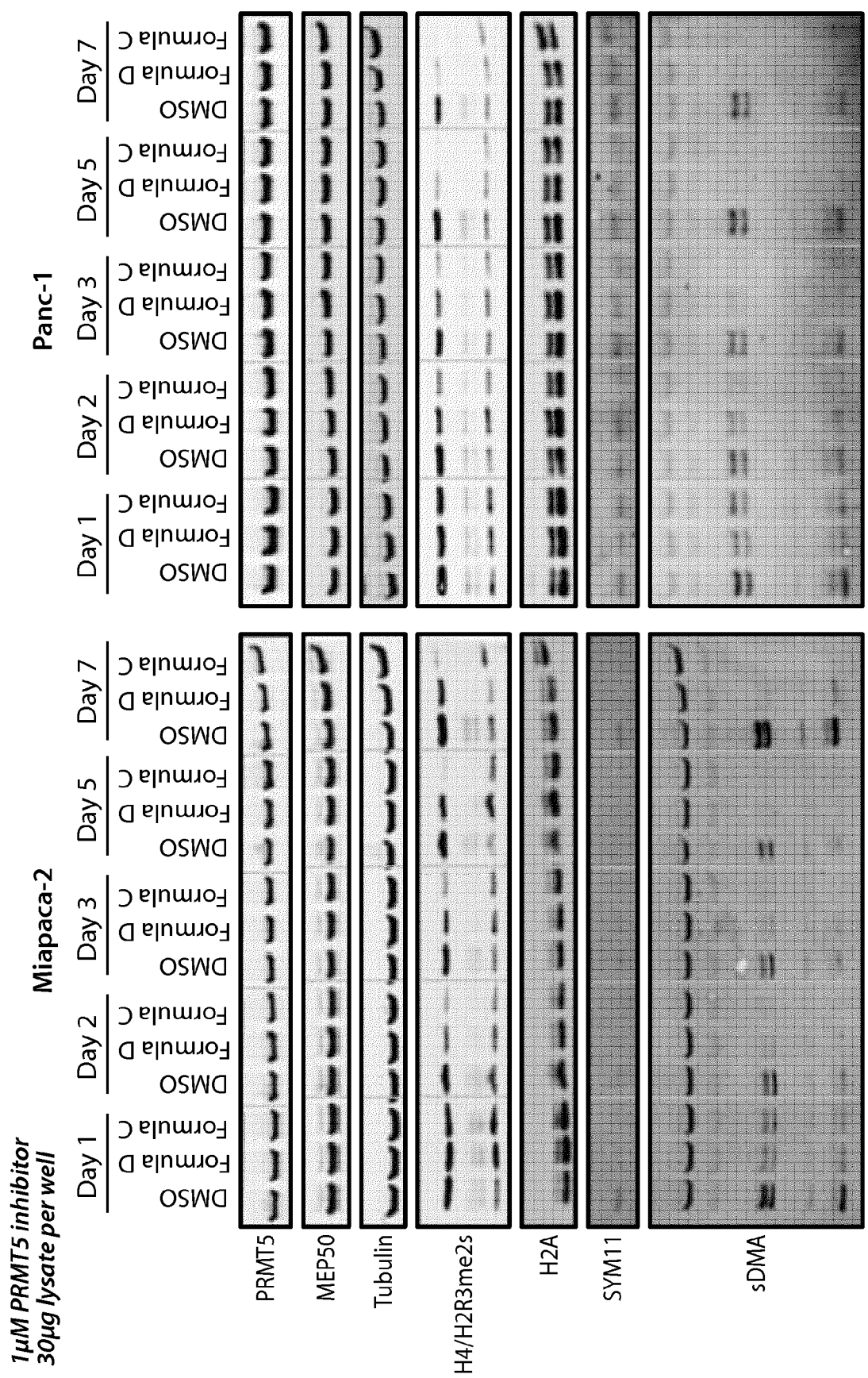
FIG. 16 shows pancreatic cells treated with PRMT5 inhibitors of Formulae C and D.

In this example, the efficacy of PRMT5 inhibitors in treating pancreatic cancer are demonstrated. FIG. 16 shows the results of Western blot analysis of two pancreatic cancer cell lines (Miapaca-2 and Panc-1) treated with Formula C and D.

Figure 17:
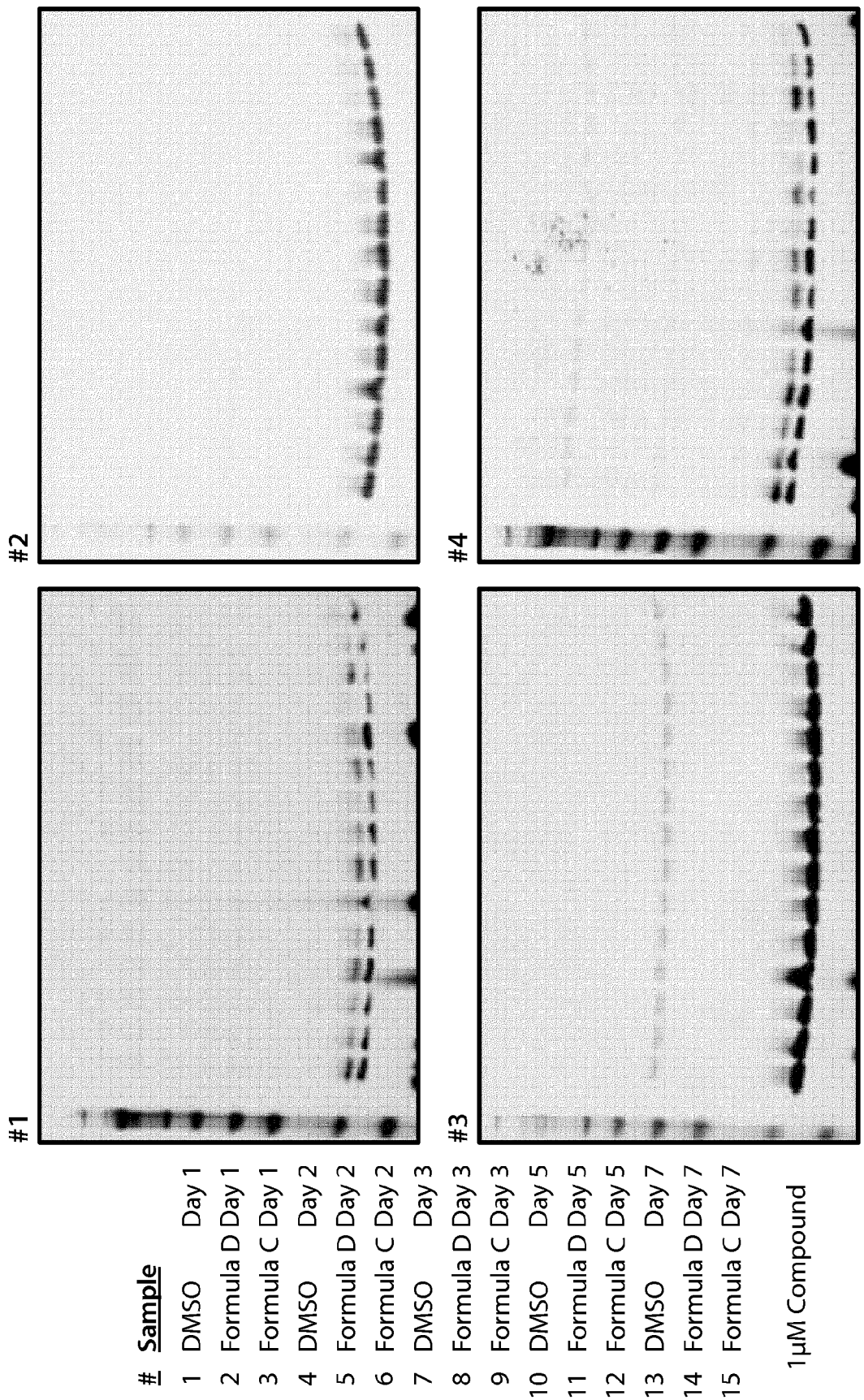
FIG. 17 illustrates a CST-H4R3me2s antibody blot of methyl mark in Miapaca-2 pancreatic cancer cells treated with PRMT5 inhibitors of Formulae C and D.

FIG. 17 shows the results of a Symmetrical dimethylation on arginine-3 of histone H4 (H4R3me2s) test performed on Miapaca-2 cells treated with Formula C and Formula D.

Figure 18:
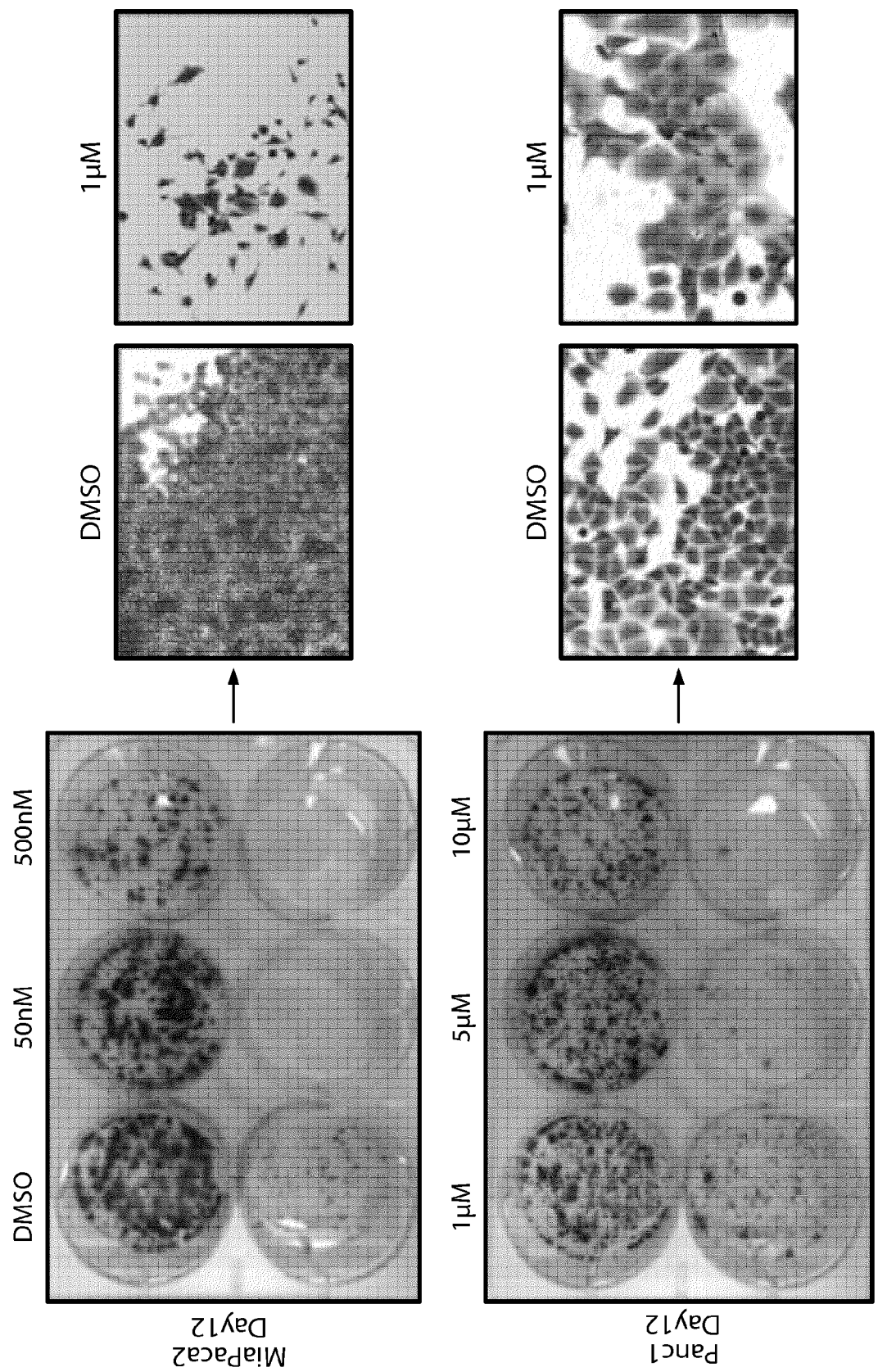
FIG. 18 illustrates the effect of foci formation and cellular morphology in pancreatic cancer cell lines (Miapaca-2, Panc-1).

The effects of treatment with Formula D on pancreatic cancer cell morphology was also tested. Treatment with each compound results in the inhibition of cancer cell growth in both Miapaca-2 and Panc-1 cell lines, as shown in FIG. 18.

Figure 19:
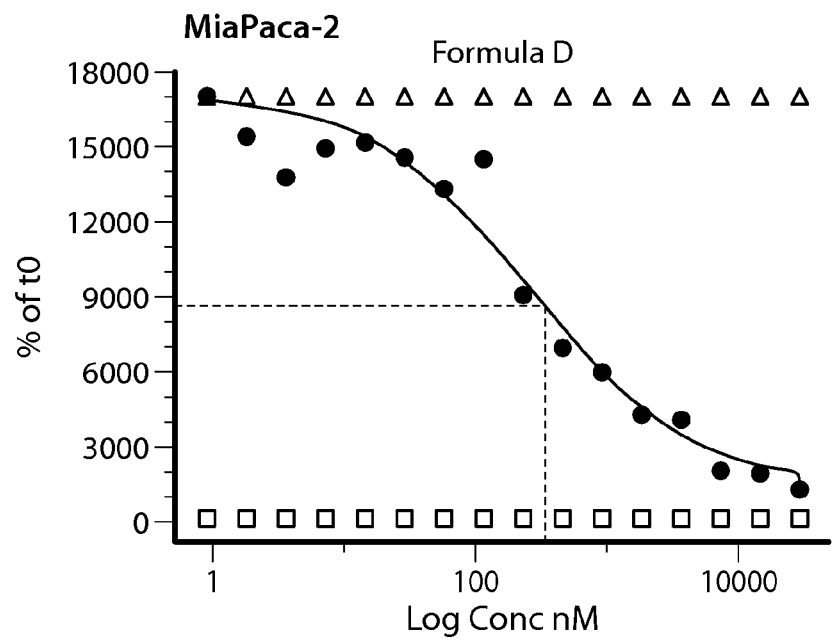
FIG. 19 shows 2D proliferation studies in pancreatic cancer cell lines (Miapaca-2, Panc-1). Calculation of growth inhibitory concentrations (g $IC_{50}$) at Days 4, 6 and 13 treated with Formula D.
Figure 19:
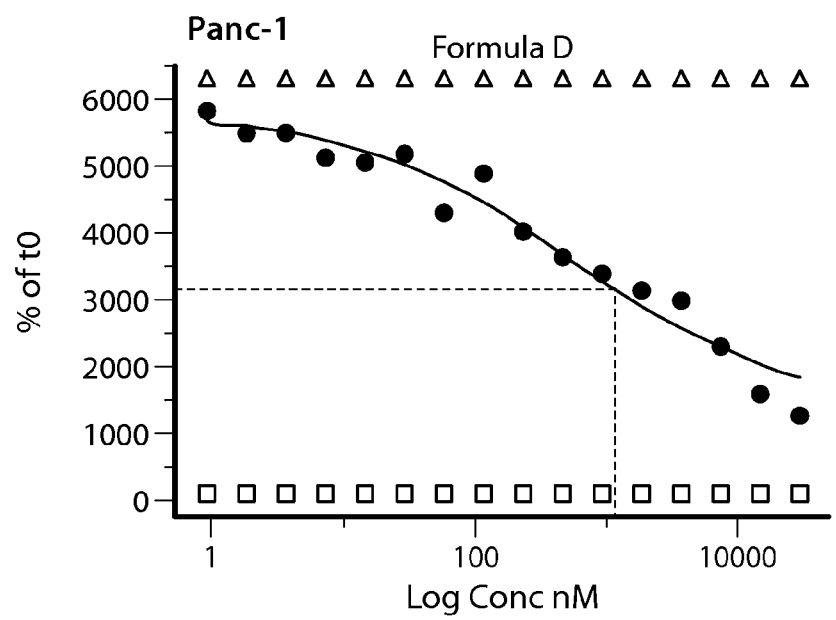

2D-proliferation assays were also performed on pancreatic cell lines treated with Formula D. Treatment of both Miapaca-2 and Panc-1 cells with Formula D results in a decrease in cell proliferation, as shown in FIG. 19. The calculated growth inhibitory concentration ($gIC_{50}$) in MiaPaca-2 cells was 349 nM at Day 4, 269 nM at Day 6 and 929 nM at Day 13. The calculated growth inhibitory concentration ($gIC_{50}$) in Panc-1 cells was 1990 nM at Day 4, 1243 nM at Day 6 and 3904 nM at Day 13.

Example 9: Heme Cancer Data

Figure 20:
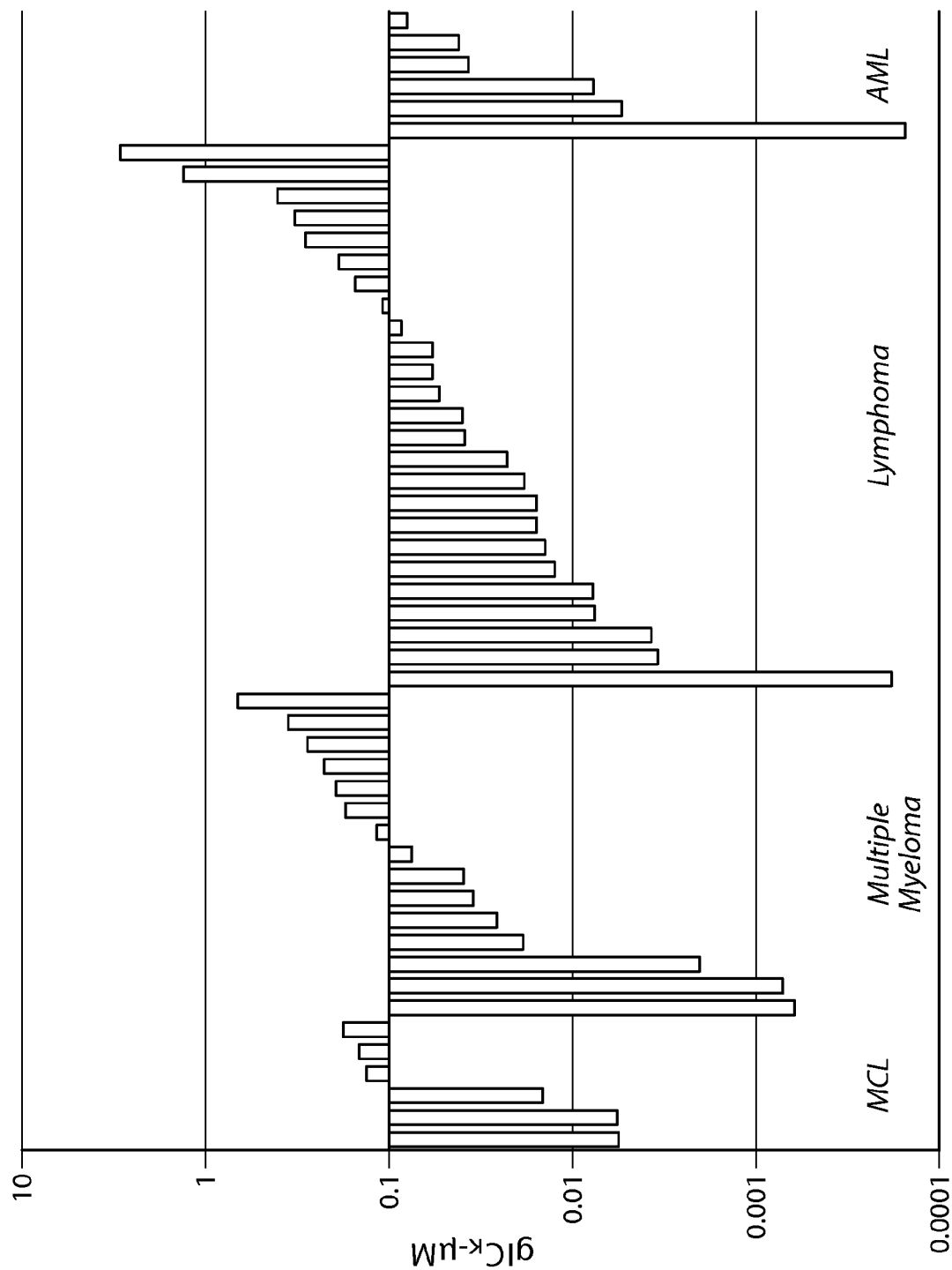
FIG. 20 shows data illustrating the inhibition of proliferation in heme cancer cell lines treated with Formula C.

Heme cancer cells were treated with a PRMT5 inhibitor and a Cell Titer-Glo growth/death assay was performed. As shown in FIG. 20, treatment with a PRMT inhibitor of Formula C inhibits proliferation in several heme cancer cell lines, including mantle cell lymphoma (MCL), acute myeloid lymphoma (AML) cell lines and multiple myeloma (MM), and lymphoma cell lines.

Example 10: p53-Positive Cancer Data

Figure 21:
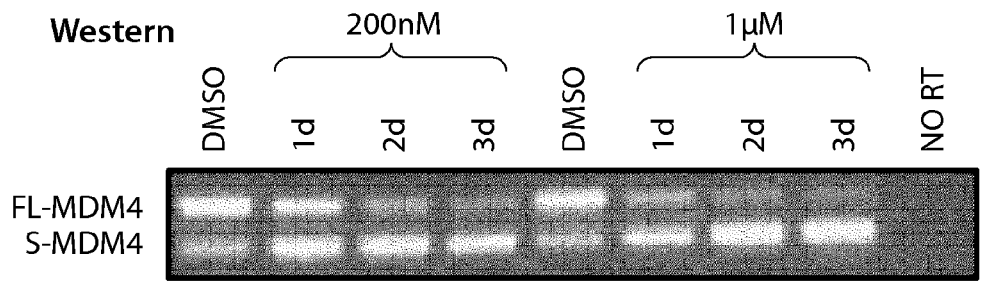
FIG. 21 shows PRMT5 inhibition by treatment with a compound of Formula C attenuates MDM4 splicing and increases p53 expression.
Figure 21:
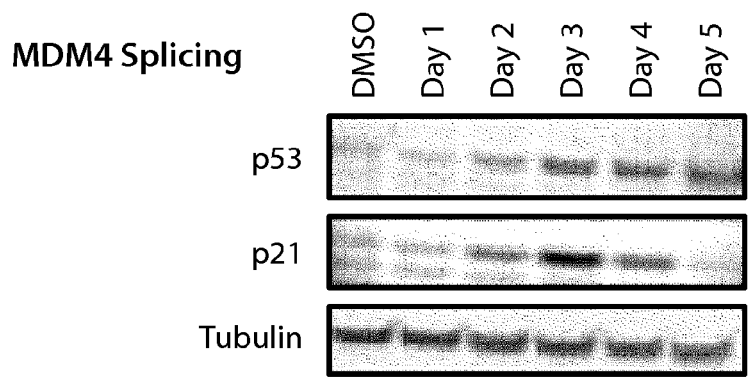
Figure 22:
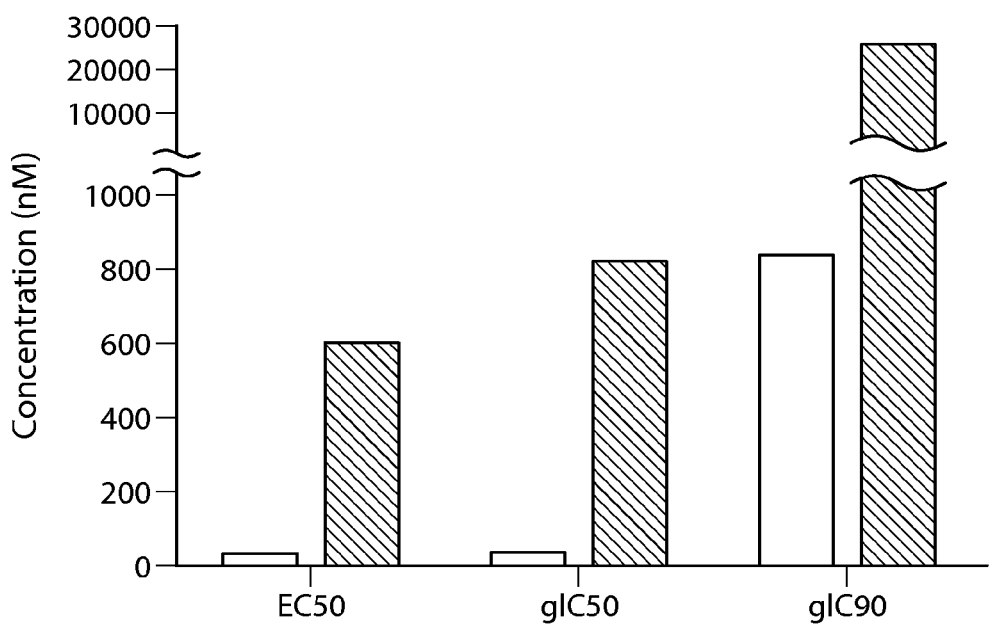
FIG. 22 illustrates that cells lacking p53 are less sensitive to PRMT5 inhibition by treatment with a compound of Formula C than cells having p53.

PRMT5 methylation of non-histone substrates (such as E2F1 and p53) also contributes to cancer cell growth and death. Results of Western blot and PCR experiments indicate PRMT5 inhibition leads to gene expression and splicing changes, ultimately resulting in the induction of p53 in cancer cells. A PRMT5 inhibitor of Formula C was used to generate the data in FIG. 21 and FIG. 22. As shown in FIG. 21, PRMT5 inhibition in Z138 mantle cell lymphoma cells attenuates MDM4 splicing and increases p53 expression. Also, cells (e.g., SW48 colon cancer cells) lacking p53 (i.e., SW48$^{-/-}$) were less sensitive to PRMT5 inhibition compared to their wild-type counterparts (i.e., SW48), for example based on $EC_{50}$, $gIC_{50}$, or $gIC_{90}$ (FIG. 22).

Figure 23:
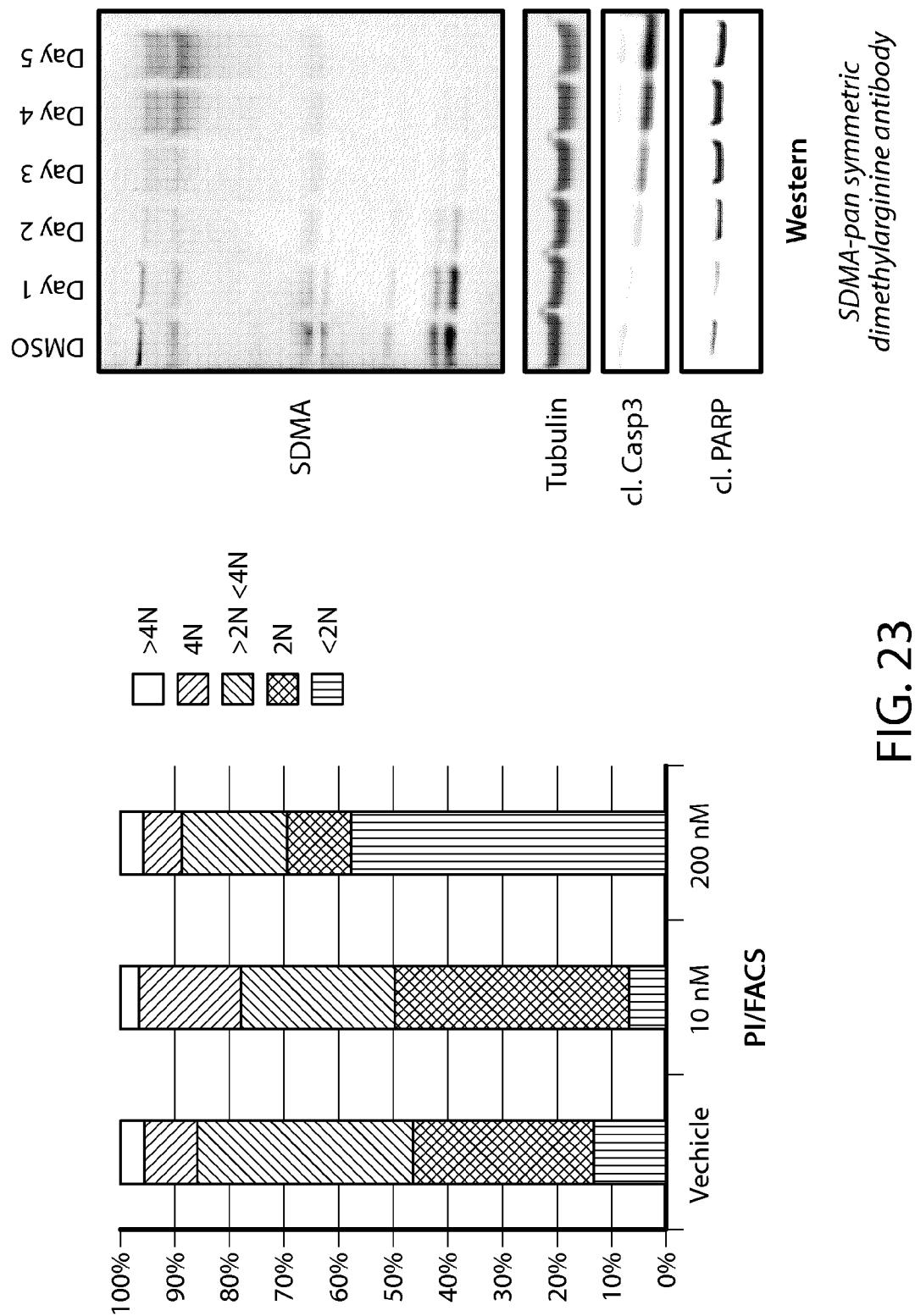
FIG. 23 illustrates G1 arrest and cell death in mantle cell lymphoma cell line Z138 in response to a PMRT5 inhibitor of Formula C.

Example 11: Cell Cycle Analysis (Propidium Iodide Staining, Day 3) (Left Panel) and Western Analysis (1 µM PRMT5 Inhibitor) (Right Panel) of Mantle Cell Lymphoma Line, Z-138, Treated with PRMT5 Inhibitor Formula C As illustrated in FIG. 23, PRMT5 inhibition leads to G1 arrest (bar at 10 nM) and cell death (bar at 200 nM) in mantle cell lymphoma line, Z138. Western analysis demonstrates time-dependent inhibition of PRMT5 (sDMA, symmetric dimethylarginine) and the induction of cell death pathways (cleaved Caspase-3 and cleaved PARP) in response to PRMT5 inhibitor treatment.

Cell Cycle Analysis

Cells were seeded in 6-well tissue culture dishes in a volume of 3 mL IMDM+10% horse serum (supplemented with 0.5 µg/mL puromycin for transduced cell lines). Cells were treated with DMSO, 10 nM Formula C, or 200 nM Formula C for 3 days. Cells were harvested by centrifuging at 2,000 RPM for 5 minutes, washing with PBS, washing with citrate buffer, then aspirating excess citrate buffer to leave approximately 50 μL remaining above pellet. Pellets were frozen at −80° C. until ready to process.

Pellets were propidium iodide-stained for FACS using the Becton Dickinson CycleTEST PLUS kit (cat. #340242). Solutions A, B, and C of the kit were thawed and then kept on ice. Cell pellets were thawed rapidly at 37° C. and pipetted up and down to resuspend in 50 μL of citrate buffer.

Approximately one quarter of the cell pellet volume was transferred to a fresh Eppendorf tube. 250 μL of solution A was added to each sample and then inverted 7 to 10 times. Samples were placed on a shaker at 150 RPM for 10 minutes at room temperature. Samples were on ice when not shaking. 250 μL of solution B and 250 μL of solution C were added to each sample in the same fashion. Samples were covered in foil to minimize light exposure following addition of propidium iodide in solution C. Samples were transferred into FACS tubes (polystyrene, Falcon 352058) and analysis of stained specimens was completed within 3 hours of staining.

Samples were processed by FACS on a Becton Dickinson FACSCalibur machine. The percentage of cells in each cell cycle stage was determined using the cell cycle function on the gated single cell population with FlowJo V10 software.

Western Analysis

Z138 cells were seeded at approximately 6-well tissue culture dishes in IMDM+10% horse serum media. Cells were treated with 1 μM of compound for 1, 2, 3, 4, or 5 days. Cell pellets were collected by centrifuging at 500×g for 5 minutes, washing once with PBS, and freezing at −80° C. until ready to be processed.

Protein lysates were prepared by adding RIPA buffer (Sigma R0278) containing protease inhibitor (about 5× the volume of the cell pellet, or roughly 250 μL) to each cell pellet and pipetting to resuspend. Samples were sonicated with 10×1 second pulses then centrifuged at maximum speed (13,300 RPM) for 6 minutes. Supernatant (200 μL) was transferred to a fresh Eppendorf tube, and pellets were discarded. Protein concentration was determined using a Pierce BCA Protein Assay kit.

Protein gel samples were prepared by combining 20 μg of lysate with appropriate volumes of Life Technologies NuPage Sample Reducing Agent, LDS Sample Buffer, and RIPA buffer. Gel samples were heated for 5-10 minutes at 100° C. in a heat block. A 15-well Invitrogen 4-12% Bis-Tris NuPAGE-SDS gel was loaded with a volume of 19 μL per well, and run in MES SDS buffer at 150V for about 1 hour or until maximal separation of bands was achieved.

Gels were transferred onto nitrocellulose membranes using an Invitrogen iBlot system. Blots were blocked with LiCOR Odyssey buffer (cat. #927-40000) for 30 minutes, rocking at room temperature. Primary antibodies were diluted in Licor Odyssey blocking buffer (with 0.1% TWEEN-20 addition) and applied overnight, rocking at 4° C. Blots were then washed 3×15 minutes in PBST, treated with fluorescent secondary antibodies (1:10,000 diluted in 0.1% Tween-20/Odyssey blocking reagent) for 1 hour rocking at room temperature, washed again 3×15 minutes in PBST, then imaged using a LiCOR Odyssey scanner.

Example 12: PRMT5 Inhibition Attenuates MDM4 Splicing and Increases p53 Expression Generation of Transduced Z138 Cell Lines 1×10⁶ Z138 cells were seeded in a 6-well tissue culture dish in a volume of 3 mL IMDM+10% horse serum per well. Lentiviruses (MDM4 or EGFP in pLEX vector) were prepared as previously described or purchased from Santa Cruz Biotechnology (cat. # sc-29435-V and sc-108080 for p53 shRNA or scrambled shRNA lentiviruses, respectively). Lentiviral particles were added to seeded cells at MOT=20 and supplemented with polybrene at 8 μg/mL. 6-well plates were sealed with Parafilm and spun at 1000×g for 90 minutes at 37° C. for lentiviral treatment. The contents of each well were then collected into separate 15 mL conical tubes and spun at 1000×g for 5 minutes. Supernatant (containing lentivirus and polybrene) was discarded and the cell pellet was resuspended in 3 mL of IMDM+10% horse serum. Cells were replated in a fresh 6-well tissue culture dish and incubated at 37° C. and 5% $CO_2$ for 48 hours.

Transduction efficiency was evaluated for EGFP-transduced cells using fluorescence microscopy. If EGFP expression was observed, transduction was successful and puromycin was added at a concentration of 0.5 μg/mL to select for transduced cells. The transduced population was expanded (under continuous culture with puromycin) until enough cells were present to seed for experiments.

MDM4 Splicing Analysis (PCR)

Z138 cells were seeded in 10 cm tissue culture dishes at a density of approximately 3×10⁶ cells per dish in a volume of 10 mL IMDM+10% horse serum media. Cells were treated with 200 nM or 1 μM of compound at 0.5% DMSO for 1, 2, or 3 days. Cell pellets were harvested by washing once with PBS, trypsinizing for 5 minutes at 37° C., centrifuging at 1000×g for 5 minutes, then storing at −80° C. until ready to process.

RNA was extracted from cell pellets. First, pellets were thawed on ice and then quickly resuspended in 500 μL Trizol reagent. Samples were then incubated 2-3 minutes at room temperature and vortexed for 30 sec to completely homogenize the lysate. 50 μL of water and 50 μL of chloroform were added to each Trizol-cell mixture, then each sample was vortexed for 30 sec to mix completely. Samples were loaded onto MaXtract High Density tubes and spun at 14,000 RPM for 5 minutes. The clear supernatant (aqueous phase) from each tube was transferred to a new 2 mL tube and 2× volume of freshly prepared 70% ethanol was added to each sample. Samples were loaded onto RNeasy spin columns (part of Qiagen RNeasy Mini kit). Columns were centrifuged at 9000×g for 15 sec and flow-through was discarded. 350 μL Buffer RW1 was added to each column and samples were centrifuged at −9000×g for 15 sec and flow-through was discarded. DNase I mixture (Qiagen) was prepared by mixing 10 μL of DNase I with 70 μL Buffer RDD for each sample, then 80 μL of DNase I mixture was added to each sample and incubated at room temperature for 15 minutes. 350 μL of Buffer RW1 was added to each column and samples were centrifuged at −9000×g for 15 sec and flow-through was discarded. Columns were then washed twice with 500 μL of prepared Buffer RPE and samples were centrifuged at 9000×g for 15 sec and flow-through was discarded. RNeasy columns were placed into new 2 mL collection tubes and spun at 14000 RPM for 1 min to dry columns. RNeasy columns were then transferred to 1.5 mL collection tubes and 30 μL of RNase-free water was added to each column. Columns were incubated at room temperature for 1 min and then spun at 14000 RPM for 1 min. This elution step was then repeated with an additional 30 μL RNase-free water for a total volume of 60 μL. RNA concentration was analyzed on a Nanodrop.

Next, RNA was reverse transcribed to generate cDNA. In a 96-well PCR plate, 1 μg of RNA was diluted to a final volume of 25 μL in sterile, nuclease-free water. Master mix was prepared using High Capacity Reverse Transcription Reagents (ABI #4274966). 25 μL of master mix was added to each well containing RNA for a final reaction volume of 50 µL. Reactions were incubated in a thermal cycler programmed as follows: 10 minutes at 25° C., 2 hours at 37° C., and 5 minutes at 85° C. cDNA was diluted by combining 25 µL of the reverse transcription reaction product with 200 µL of nuclease free water in a 96-well polypropylene plate.

Short and full-length HDMX splice variants were PCR amplified from diluted cDNA. First, PCR master mix was prepared by combining Thermo DreamTaq Green PCR Master Mix (2×) (cat. #K1082), HDMX forward primer (final concentration of 1 µM, Biosearch Technologies SS294168-01, TGTGGTGGAGATCTTTTGGG (SEQ ID NO: 1)), and HDMX reverse primer (final concentration of 1 µM, Biosearch Technologies, SS294169-01, GCAGTGTGGGGATATCGT (SEQ ID NO: 2)). In a 96-well PCR plate, 10 µL of diluted cDNA and 40 µL of PCR master mix were combined to generate a 50 µL reaction. The PCR reaction was conducted in a thermal cycler: 1 cycle of 5 minutes at 95° C.; 26 cycles of 40 sec at 95° C., 30 sec at 58° C., and 40 sec at 72° C.; then 1 cycle of 4 minutes at 72° C.

PCR products were visualized by running 15 µL per lane on a 2% agarose ethidium bromide gel and imaging on a BioRad VersaDoc system.

p53 and p21 Expression Analysis (Western)

Z138 cells were seeded at approximately 3×10$^6$ cells/dish in 10 cm tissue culture dishes in a volume of 10 mL IMDM+10% horse serum media. Cells were treated with 1 µM of Formula C for 1, 2, 3, 4, or 5 days. Cell pellets were collected by centrifuging at 500×g for 5 minutes, washing once with PBS, and freezing at −80° C. until ready to be processed.

Protein lysates were prepared by adding RIPA buffer (Sigma R0278) containing protease inhibitor (about 5× the volume of the cell pellet, or roughly 250 µL) to each cell pellet and pipetting to resuspend. Samples were sonicated with 10×1 second pulses then centrifuged at maximum speed (13,300 RPM) for 6 minutes. 200 µL of supernatant was transferred to a fresh Eppendorf tube, and pellets were discarded. Protein concentration was determined using a Pierce BCA Protein Assay kit.

Protein gel samples were prepared by combining 20 µg of lysate with appropriate volumes of Life Technologies NuPage Sample Reducing Agent, LDS Sample Buffer, and RIPA buffer. Gel samples were heated for 5-10 minutes at 100° C. in a heat block. A 15-well Invitrogen 4-12% Bis-Tris NuPAGE-SDS gel was loaded with a volume of 19 µL per well, and run in MES SDS buffer at 150V for about 1 hour or until maximal separation of bands was achieved.

Gels were transferred onto nitrocellulose membranes using an Invitrogen iBlot system. Blots were blocked with LiCOR Odyssey buffer (cat. #927-40000) for 30 minutes, rocking at room temperature. Primary antibodies (p53, Santa Cruz Biotech sc-126 at 1:200; p21, Cell Signaling #2946 at 1:1,000; tubulin, Sigma T9026 at 1:5,000) were diluted in Licor Odyssey blocking buffer (with 0.1% TWEEN-20 addition) and applied overnight, rocking at 4° C. Blots were then washed 3×15 minutes in PBST, treated with fluorescent secondary antibodies (1:10,000 diluted in 0.1% Tween-20/Odyssey blocking reagent) for 1 hour rocking at room temperature, washed again 3×15 minutes in PBST, then imaged using a LiCOR Odyssey scanner.

Figure 24:
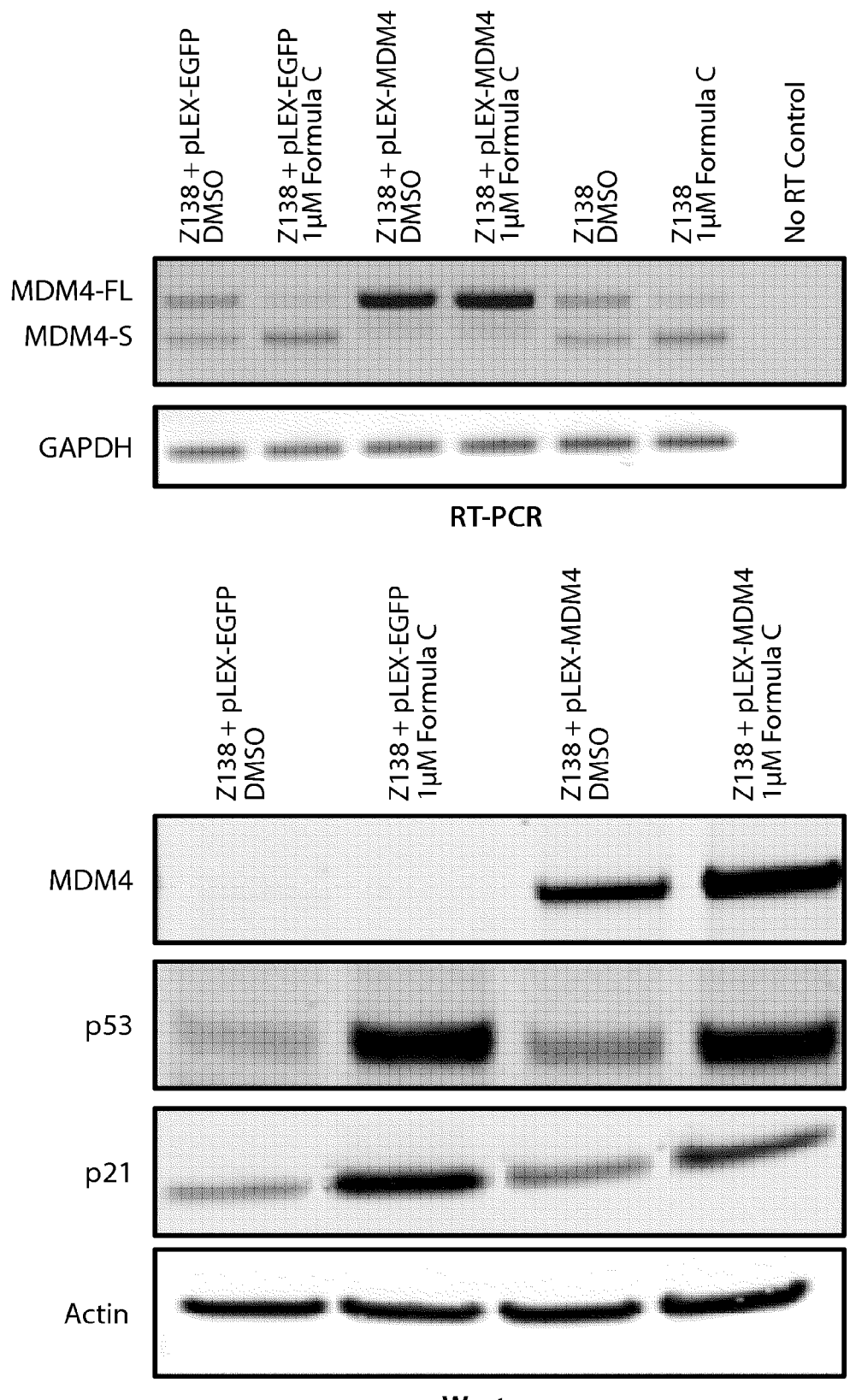
FIG. 24 illustrates the role of MDM4 splicing in the induction of the p53 pathway activity in response to a PRMT5 inhibitor of Formula C.

The experimental results in FIG. 24 illustrate that PRMT5 inhibition attenuates MDM4 splicing and increases p53 expression in Z138 cells.

Example 13: Z-138 Cells Overexpressing Full Length (FL) MDM4 are Less Sensitive to PRMT5 Inhibition Generation of Transduced Z138 Cell Lines Transduced Z138 cell lines were prepared as described above.

Cell Cycle Analysis

Cells were seeded at 250,000 cells/well in 6-well tissue culture dishes in a volume of 3 mL IMDM+10% horse serum (supplemented with 0.5 µg/mL puromycin for transduced cell lines). Cells were treated with DMSO, 50 nM Formula C, or 500 nM Formula C for 2, 3, or 4 days. Cells were harvested by centrifuging at 2,000 RPM for 5 minutes, washing with PBS, washing with citrate buffer, then aspirating excess citrate buffer to leave approximately 50 µL remaining above pellet. Pellets were frozen at −80° C. until ready to process.

Pellets were propidium iodide-stained for FACS using the Becton Dickinson CycleTEST PLUS kit (cat. #340242). Solutions A, B, and C of the kit were thawed and then kept on ice. Cell pellets were thawed rapidly at 37° C. and pipetted up and down to resuspend in 50 µL of citrate buffer. Approximately one quarter of the cell pellet volume was transferred to a fresh Eppendorf tube. 250 µL of solution A was added to each sample and then inverted 7 to 10 times. Samples were placed on a shaker at 150 RPM for 10 minutes at room temperature. Samples were on ice when not shaking. 250 µL of solution B and 250 µL of solution C were added to each sample in the same fashion. Samples were covered in foil to minimize light exposure following addition of propidium iodide in solution C. Samples were transferred into FACS tubes (polystyrene, Falcon 352058) and analysis of stained specimens was completed within 3 hours of staining.

Samples were processed by FACS on a Becton Dickinson FACSCalibur machine. The percentage of cells in each cell cycle stage was determined using the cell cycle function on the gated single cell population with FlowJo V10 software.

Figure 25:
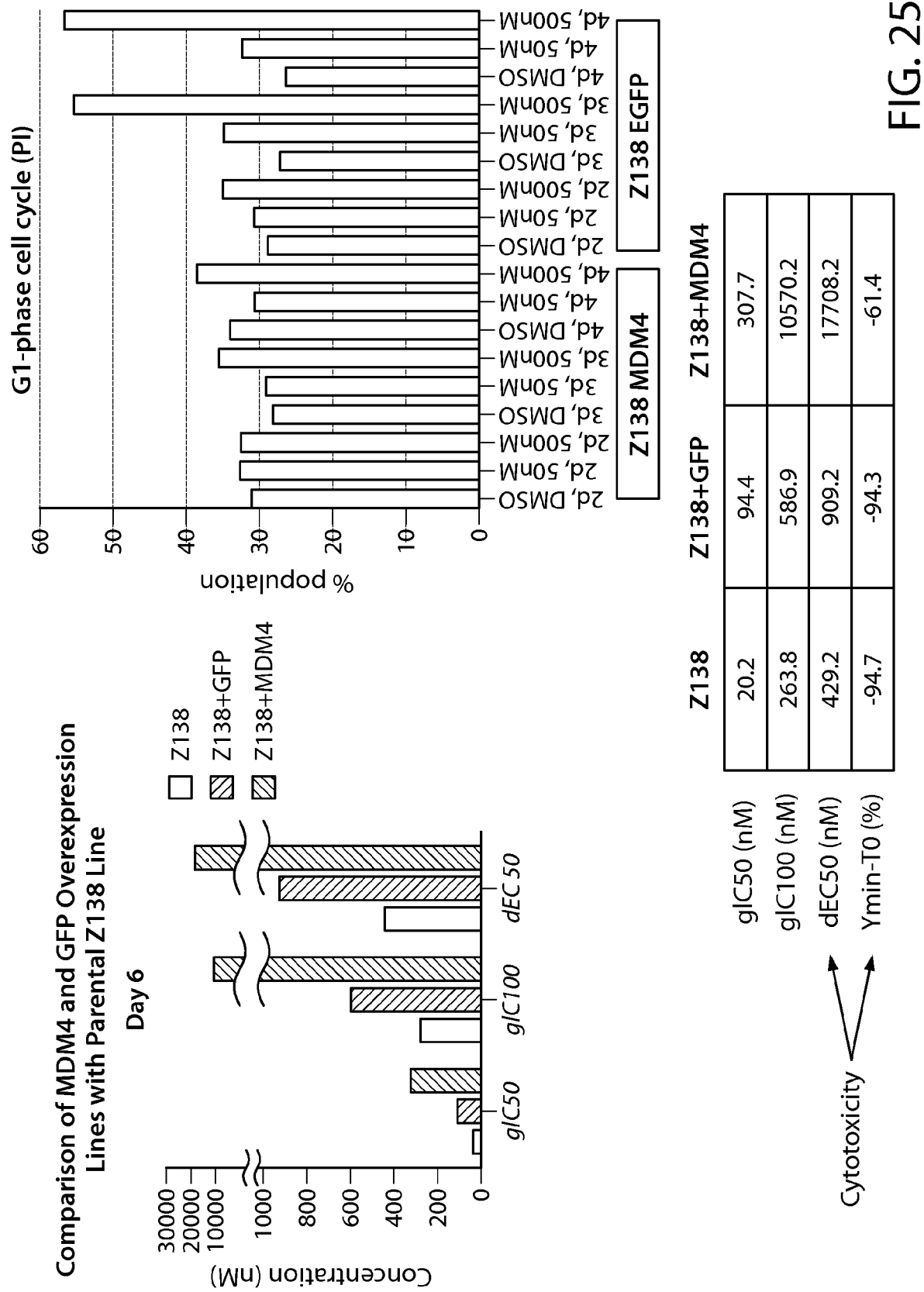
FIG. 25 illustrates that Z-138 cells overexpressing full length (FL) MDM4 are less sensitive to PRMT5 inhibition.

The experimental results in FIG. 25 illustrate that Z-138 cells overexpressing full length (FL) MDM4 are less sensitive to PRMT5 inhibition.

Other Embodiments

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of treating colon cancer, the method comprising administering a PRMT5 inhibitor to a subject having colon cancer, wherein the colon cancer is p53-positive.

2. The method of claim 1, wherein tumor growth of the cancer is inhibited more than about 50%.

3. The method of claim 1, wherein methyl mark of the cancer is reduced more than about 80%.

4. The method of claim 1, wherein the PMRT5 inhibitor is a compound of Formula 2:

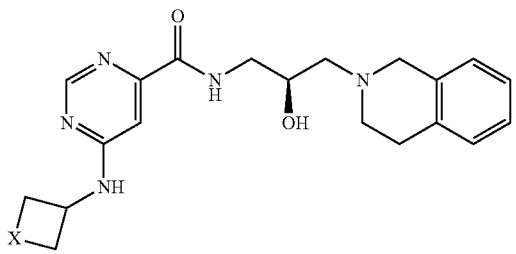

Formula 2 or a pharmaceutically acceptable salt thereof, wherein X is —C(R$^{XC}$)$_2$—, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl; or, wherein the PMRT5 inhibitor is a compound of Formula 3:

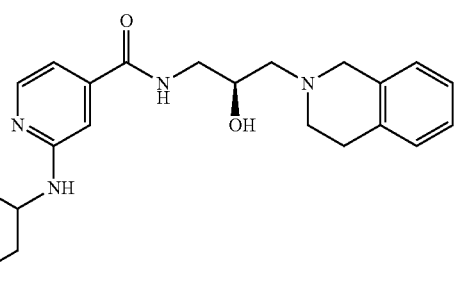

Formula 3 or a pharmaceutically acceptable salt thereof, wherein R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl; or, wherein the PMRT5 inhibitor is a compound of Formula 4:

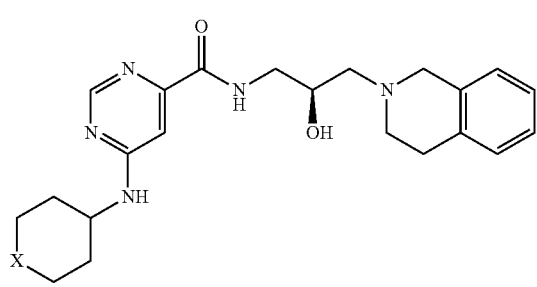

Formula 4

Formula 4 or a pharmaceutically acceptable salt thereof, wherein X is —C(R$^{XC}$)$_2$—, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; $R^{XN}$ is independently hydrogen, optionally substituted alkyl, optionally substituted carbocyclyl, optionally substituted heterocyclyl, optionally substituted aryl, optionally substituted heteroaryl, —C(=O)$R^{XA}$, or a nitrogen protecting group; $R^{XA}$ is optionally substituted alkyl, optionally substituted carbocyclyl, optionally substituted heterocyclyl, optionally substituted aryl, or optionally substituted heteroaryl; or, wherein the PMRT5 inhibitor is a compound of Formula 5:

Formula 5

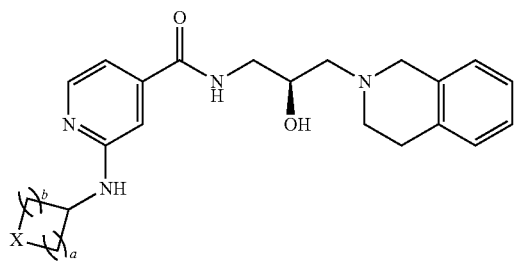

or a pharmaceutically acceptable salt thereof, wherein each instance of a and b is independently 1 or 2, and X is —C($R^{XC}$)$_2$—, —O—, —S—, or —NR$^{XN}$—, wherein each instance of $R^{XC}$ is independently hydrogen, optionally substituted alkyl, optionally substituted carbocyclyl, optionally substituted heterocyclyl, optionally substituted aryl, or optionally substituted heteroaryl; $R^{XN}$ is independently hydrogen, optionally substituted alkyl, optionally substituted carbocyclyl, optionally substituted heterocyclyl, optionally substituted aryl, optionally substituted heteroaryl, —C(=O)$R^{XA}$, or a nitrogen protecting group; $R^{XA}$ is optionally substituted alkyl, optionally substituted carbocyclyl, optionally substituted heterocyclyl, optionally substituted aryl, or optionally substituted heteroaryl.

5. The method of claim 1, wherein the PMRT5 inhibitor is a compound of Formula A:

Formula A

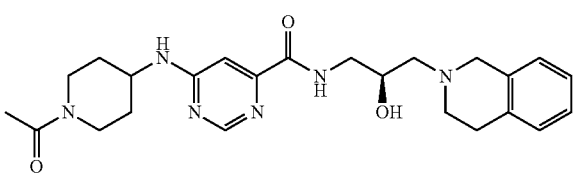

or a pharmaceutically acceptable salt thereof.

6. The method of claim 1, wherein the PMRT5 inhibitor is a compound of Formula B:

Formula B

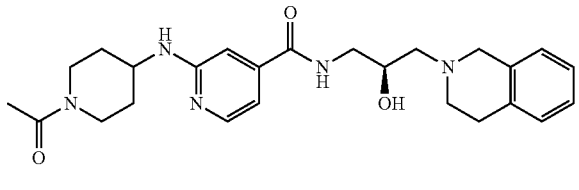

or a pharmaceutically acceptable salt thereof.

7. The method of claim 1, wherein the PMRT5 inhibitor is a compound of Formula C:

Formula C

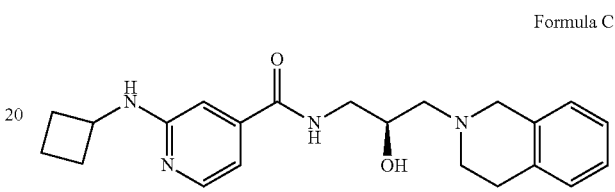

or a pharmaceutically acceptable salt thereof.

8. The method of claim 1, wherein the PMRT5 inhibitor is a compound of Formula E:

Formula E

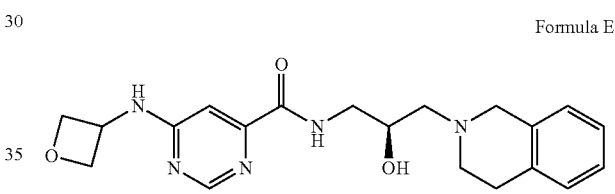

or a pharmaceutically acceptable salt thereof.

9. The method of claim 1, wherein the PMRT5 inhibitor is a compound of Formula F:

Formula F

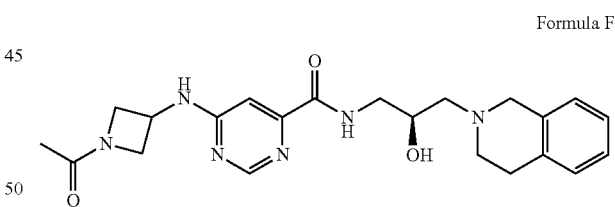

or a pharmaceutically acceptable salt thereof.

10. The method of claim 1 further comprising diagnosing the subject as having colon cancer.

11. A method for treating colon cancer that is sensitive to treatment with a PRMT5 inhibitor, the method comprising administering to a subject a composition comprising a PRMT5 inhibitor wherein:
   (a) the presence or absence of p53 has been detected in a biological sample obtained from the subject; and,
   (b) the subject has been identified as having colon cancer that is sensitive to treatment with a PRMT5 inhibitor based upon the presence of p53 in the sample.

12. The method of claim 11, wherein the PMRT5 inhibitor is a compound of Formula 2:

Formula 2

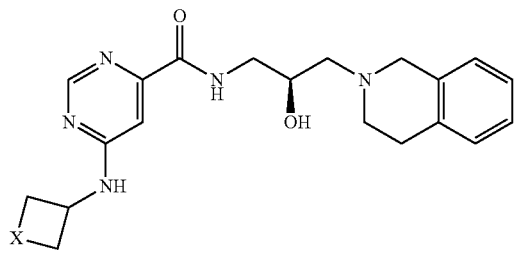

or a pharmaceutically acceptable salt thereof, wherein X is —C(R$^{XC}$)$_2$—, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl; or, wherein the PMRT5 inhibitor is a compound of Formula 3:

Formula 3 or a pharmaceutically acceptable salt thereof, wherein R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl; or, wherein the PMRT5 inhibitor is a compound of Formula 4:

Formula 4 or a pharmaceutically acceptable salt thereof, wherein X is —C(R$^{XC}$)$_2$—, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl; or, wherein the PMRT5 inhibitor is a compound of Formula 5:

Formula 5 or a pharmaceutically acceptable salt thereof, wherein each instance of a and b is independently 1 or 2, and X is —C(R$^{XC}$)$_2$—, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl.

13. The method of claim 11, wherein the PMRT5 inhibitor is a compound of Formula A:

Formula A

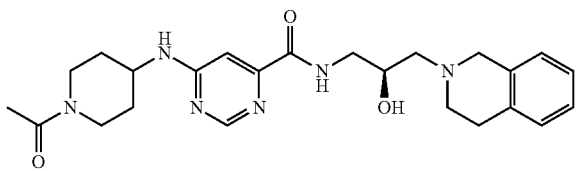 [SMILES: CC(=O)N1CCC(Nc2cc(C(=O)NC[C@H](O)CN3CCc4ccccc4C3)ncn2)CC1]

or a pharmaceutically acceptable salt thereof.

14. The method of claim 11, wherein the PMRT5 inhibitor is a compound of Formula B:

Formula B

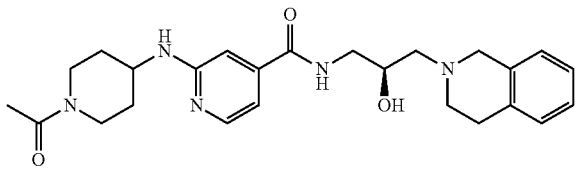 [SMILES: CC(=O)N1CCC(Nc2cc(C(=O)NC[C@H](O)CN3CCc4ccccc4C3)ccn2)CC1]

or a pharmaceutically acceptable salt thereof.

15. The method of claim 11, wherein the PMRT5 inhibitor is a compound of Formula C:

Formula C

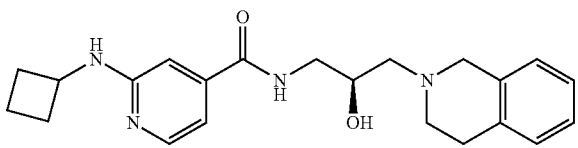 [SMILES: O=C(NC[C@H](O)CN1CCc2ccccc2C1)c1ccnc(NC2CCC2)c1]

or a pharmaceutically acceptable salt thereof.

16. The method of claim 11, wherein the PMRT5 inhibitor is a compound of Formula E:

Formula E

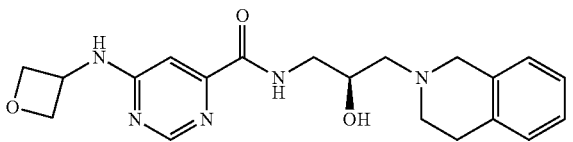 [SMILES: O=C(NC[C@H](O)CN1CCc2ccccc2C1)c1cc(NC2COC2)ncn1]

or a pharmaceutically acceptable salt thereof.

17. The method of claim 11, wherein the PMRT5 inhibitor is a compound of Formula F:

Formula F

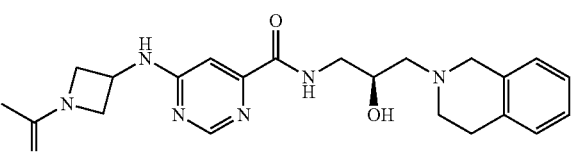

or a pharmaceutically acceptable salt thereof.

* * * * *